(12) United States Patent
Fischell et al.

(10) Patent No.: US 7,991,460 B2
(45) Date of Patent: Aug. 2, 2011

(54) METHODS AND APPARATUS FOR DETECTING CARDIAC EVENTS BASED ON HEART RATE SENSITIVE PARAMETERS

(75) Inventors: David R. Fischell, Fair Haven, NJ (US); Jonathan Harwood, Rumson, NJ (US); Steven R. Johnson, Fair Haven, NJ (US); Bruce Hopenfeld, Oceanport, NJ (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 360 days.

(21) Appl. No.: 12/232,281

(22) Filed: Sep. 15, 2008

(65) Prior Publication Data
US 2009/0082682 A1 Mar. 26, 2009

Related U.S. Application Data

(63) Continuation-in-part of application No. 11/594,806, filed on Nov. 9, 2006, which is a continuation-in-part of application No. 10/853,058, filed on May 26, 2004, now Pat. No. 7,558,623, which is a continuation-in-part of application No. 10/642,245, filed on Aug. 18, 2003, which is a continuation-in-part of application No. 10/251,505, filed on Sep. 20, 2002, now Pat. No. 6,609,023.

(51) Int. Cl.
*A61B 5/0402* (2006.01)
(52) U.S. Cl. ........................................ 600/519; 600/509
(58) Field of Classification Search .............. 607/4–28; 600/508–521
See application file for complete search history.

(56) References Cited

U.S. PATENT DOCUMENTS

| | | | |
|---|---|---|---|
| 5,113,869 A | 5/1992 | Nappholz et al. | |
| 5,135,004 A | 8/1992 | Adams et al. | |
| 5,199,428 A | 4/1993 | Obel et al. | |
| 5,313,953 A | 5/1994 | Yomtov et al. | |
| 5,342,404 A * | 8/1994 | Alt et al. | 607/6 |
| 5,497,780 A | 3/1996 | Zehender | |
| 5,792,066 A | 8/1998 | Kwong | |
| 6,112,116 A | 8/2000 | Fischell et al. | |
| 6,128,526 A | 10/2000 | Stadler et al. | |
| 6,272,379 B1 | 8/2001 | Fischell et al. | |
| 6,368,284 B1 | 4/2002 | Bardy | |
| 6,442,432 B2 | 8/2002 | Lee | |
| 6,501,983 B1 | 12/2002 | Natarajan et al. | |
| 7,066,891 B2 | 6/2006 | Stadler et al. | |

OTHER PUBLICATIONS

Zimmerman, M., et al.; "On Improving the Classification of Myocardial Ischemia Using Holter ECG Data"; Computers in Cardiology; 2004, 31, pp. 377-380.
Kligfield, et al.; "Heart rate adjustment of ST segment depression for improved detection of coronary artery disease"; Circulation; 1989, vol. 79, No. 2, pp. 245-255.
Okin, et al.; "Recovery-Phase Patterns of ST Segment Depression in the Heart Rate Domain"; Circulation; 1989, vol. 80, No. 3, pp. 533-541.

* cited by examiner

*Primary Examiner* — Scott M Getzow
(74) *Attorney, Agent, or Firm* — Rosenberg, Klein & Lee

(57) ABSTRACT

A system for the detection of cardiac events occurring in a human patient is provided. At least two electrodes are included in the system for obtaining an electrical signal from a patient's heart. An electrical signal processor is electrically coupled to the electrodes for processing the electrical signal and applying tests to determine whether a cardiac event has occurred. When the processor detects some types of changes in heart rate, event detection is altered or suspended for a period of time.

13 Claims, 21 Drawing Sheets

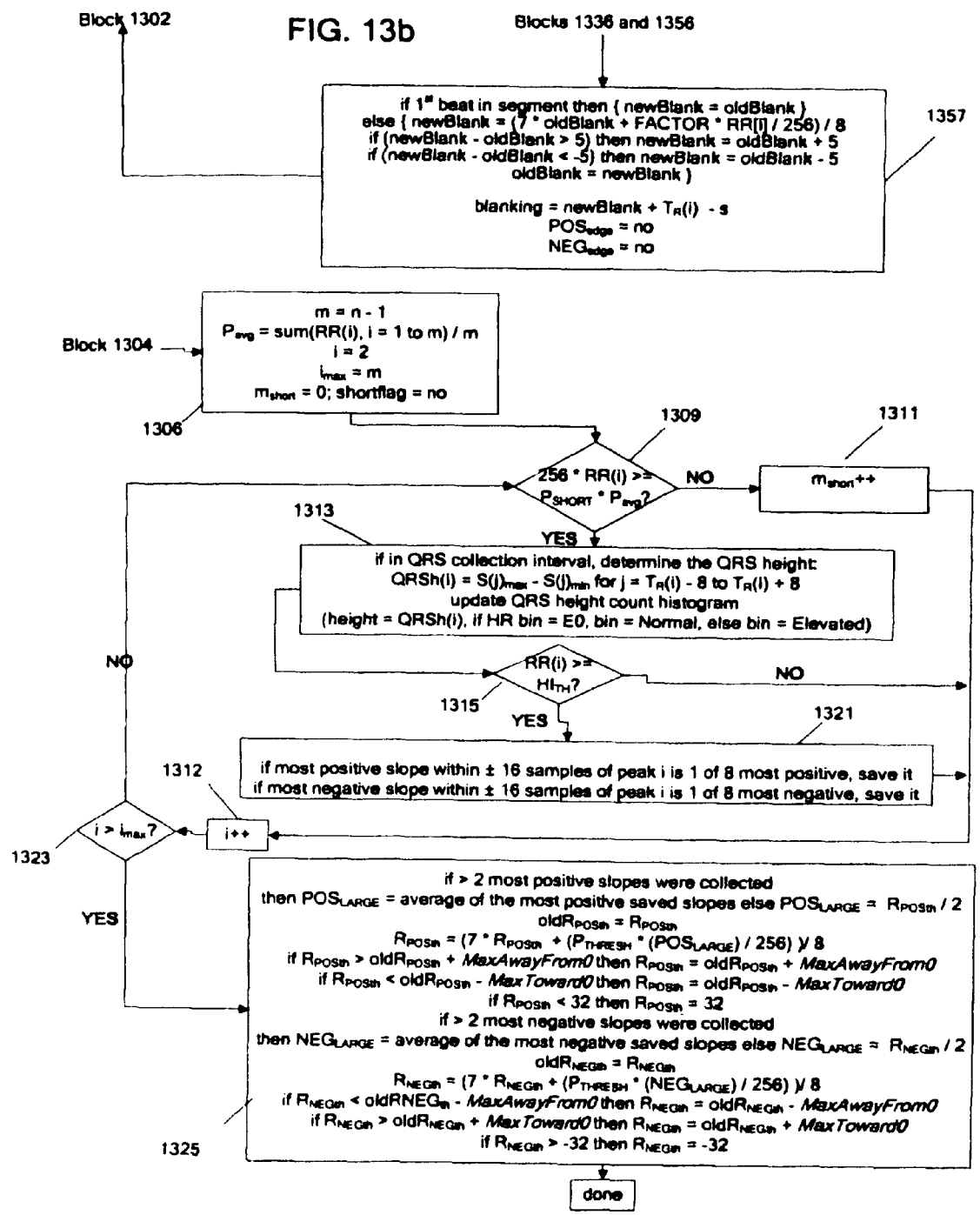

METHODS AND APPARATUS FOR DETECTING CARDIAC EVENTS BASED ON HEART RATE SENSITIVE PARAMETERS

CROSS REFERENCE TO RELATED APPLICATIONS

This application is a Continuation-In-Part of U.S. patent application Ser. No. 11/594,806, filed Nov. 9, 2006, entitled "System for Detection of Different Types of Cardiac Events," which is a Continuation-In-Part of U.S. patent application Ser. No. 10/853,058, filed May 26, 2004, now U.S. Pat. No. 7,558,623 entitled "Means and Method for the Detection of Cardiac Events," which is a Continuation-In-Part of U.S. patent application Ser. No. 10/642,245, filed Aug. 18, 2003, entitled "System for the Detection of Cardiac Events," which is a Continuation-In-Part of U.S. patent application Ser. No. 10/251,505, filed Sep. 20, 2002, now U.S. Pat. No. 6,609,023.

FIELD OF USE

This invention is in the field of systems, including devices implanted within a human patient, for the purpose of automatically detecting the onset of a cardiac event.

BACKGROUND OF THE INVENTION

Heart disease is the leading cause of death in the United States. A heart attack (also known as an Acute Myocardial Infarction (AMI)) typically results from a thrombus that obstructs blood flow in one or more coronary arteries. AMI is a common and life-threatening complication of coronary heart disease. The sooner that perfusion of the myocardium is restored (e.g., with injection of a thrombolytic medication such as tissue plasminogen activator (tPA)), the better the prognosis and survival of the patient from the heart attack. The extent of damage to the myocardium is strongly dependent upon the length of time prior to restoration of blood flow to the heart muscle.

Fischell et al in U.S. Pat. Nos. 6,112,116, 6,272,379, and 6,609,023 describe implantable systems for detecting the onset of acute myocardial infarction and providing both treatment and alarming to the patient. While Fischell et al discuss the detection of a shift in the S-T segment of the patient's electrogram from an electrode within the heart as the trigger for alarms; it may be desirable to provide more sophisticated detection algorithms to reduce the probability of false positive and false negative detection. In addition while these patents describe some desirable aspects of programming such systems, it may be desirable to provide additional programmability and alarm control features.

In particular, it may be desirable to differentiate the possibly more life threatening occlusion of the Left Anterior Descending (LAD) coronary artery from occlusions of the Circumflex (LCX) or Right Coronary Artery (RCA).

Event detection in the context of a recovery from higher heart rates presents various difficulties. One possibility for handling this problem is described in U.S. patent application Ser. No. 11/710,902 to John et al., filed Feb. 27, 2007, entitled "Systems and methods of medical monitoring according to patient state." Alternatives to the techniques described in the above mentioned application may prove more suitable for implementation in particular types of cardiac event detection devices.

In the context of body surface electrocardiograms, it is known that ST changes persist after recovery from exercise (i.e. high heart rate). Indeed, the trajectory of the ST vs. heart rate curve after exercise has been proposed as a marker for coronary artery disease. (Okin P M, Ameisen O, Kligfield P. Recovery-phase patterns of ST segment depression in the heart rate domain: identification of coronary artery disease by the rate-recovery loop. *Circulation.* 1989; 80: 533-541.)

For the purpose of this invention, the term "electrocardiogram" is defined to be the heart electrical signals from one or more skin surface electrode(s) that are placed in a position to indicate the heart's electrical activity (depolarization and repolarization). An electrocardiogram segment refers to the recording of electrocardiogram data for either a specific length of time, such as 10 seconds, or a specific number of heart beats, such as 10 beats. For the purposes of this specification the PQ segment of a patient's electrocardiogram is the typically flat segment of a beat of an electrocardiogram that occurs just before the R wave.

For the purpose of this invention, the term "electrogram" is defined to be the heart electrical signals from one or more implanted electrode(s) that are placed in a position to indicate the heart's electrical activity (depolarization and repolarization). An electrogram segment refers to the recording of electrogram data for either a specific length of time, such as 10 seconds, or a specific number of heart beats, such as 10 beats. For the purposes of this specification the PQ segment of a patient's electrogram is the typically flat segment of an electrogram that occurs just before the R wave. For the purposes of this specification, the terms "detection" and "identification" of a cardiac event have the same meaning. A beat is defined as a sub-segment of an electrogram or electrocardiogram segment containing exactly one R wave.

Heart signal parameters include PQ segment average value, ST segment average voltage value, R wave peak value, ST deviation, ST shift, average signal strength, T wave peak height, T wave average value, T wave deviation, heart rate, R-R interval and peak-to-peak voltage amplitude.

SUMMARY OF THE INVENTION

The present invention is a system for the detection of cardiac events that includes a device called a cardiosaver, and external equipment including a physician's programmer and an external alarm system. The present invention envisions a system for early detection of an acute myocardial infarction or exercise induced myocardial ischemia caused by an increased heart rate or exertion.

In the preferred embodiment of the present invention, the cardiosaver is implanted along with the electrodes. In an alternate embodiment, the cardiosaver and the electrodes could be external but attached to the patient's body. Although the following descriptions of the present invention in most cases refer to the preferred embodiment of an implanted cardiosaver processing electrogram data from implanted electrodes, the techniques described are equally applicable to the alternate embodiment where the external cardiosaver processes electrocardiogram data from skin surface electrodes.

Using one or more detection algorithms, the cardiosaver can detect a change in the patient's electrogram that is indicative of a cardiac event, such as an acute myocardial infarction, within five minutes after it occurs and then automatically warn the patient that the event is occurring. To provide this warning, the system includes an internal alarm sub-system (internal alarm means) within the cardiosaver and/or an external alarm system (external alarm means). In the preferred, implanted embodiment, the cardiosaver communicates with the external alarm system using a wireless radio-frequency (RF) signal.

The present invention includes the capability to differentiate between excessive ST shifts that occur during a lengthy period of heart rate in the "normal" range for the patient and elevated heart rate induced ischemic events that occur in the presence of heart rate in the "normal" range in a short period of time following the patient's heart rate returning to normal from an elevated state. This is done by one of several described techniques: for example 1. by having a "wait" period where detection is disabled following the return to normal heart rate from elevated heart rate, followed by a restart of detection once the heart rate has been normal for a specified period of time;
2. reclassification of an ischemic event detected in the period of time following the return to normal heart rate from elevated heart rate,
3. a persistence requirement that the abnormality in the heart signal parameter being used for ischemia detection must persist for a longer time if the patient's heart rate has been elevated in the recent past.

One aspect of the present invention that involves an intracardiac electrode, includes the capability to differentiate the possibly more life threatening occlusion of the Left Anterior Descending (LAD) coronary artery from occlusions of the Circumflex (LCX) or Right Coronary Artery (RCA). Specifically, if excessive negative ST shift (in a can-to-tip) vector with an RV apical lead tip electrode is detected for more than a predetermined period of time without an associated change in heart rate either at the time of detection or in the period before the detection, then there is very high probability that the LAD has become blocked. This differentiation for this more life threatening occlusion could be used to differentiate triage or treatments for the patient upon arrival at a medical facility. For example, a detected LAD occlusion could be used to prioritize the patient for catheterization and also direct the interventional cardiologist performing the catheterization procedure to look first at the patient's LAD and also to use appropriate technology to be able to quickly open the blocked LAD when angiographic confirmation is obtained.

Excessive positive ST segment elevation (in a can-to-tip orientation) is most likely an LCX occlusion or an RCA occlusion; the location of the occlusion may be determined with skin surface electrodes.

Thus the combination of intracardiac electrogram and 12 lead ECG data can also be used within the present invention to suggest the first place to look for the culprit ruptured plaque obstruction during cardiac catheterization. This is important because RCA catheterization often uses a different shape guiding catheter than LCX/LAD procedures and with an obstructed coronary artery anything that saves time can have significant benefit.

These and other objects and advantages of this invention will become obvious to a person of ordinary skill in this art upon reading of the detailed description of this invention including the associated drawings as presented herein.

BRIEF DESCRIPTION OF THE DRAWINGS

FIGS. 13a and 13b are a block diagram of the R wave peak detection subroutine of the cardiosaver event detection program.

DETAILED DESCRIPTION OF THE INVENTION

Figure 1:
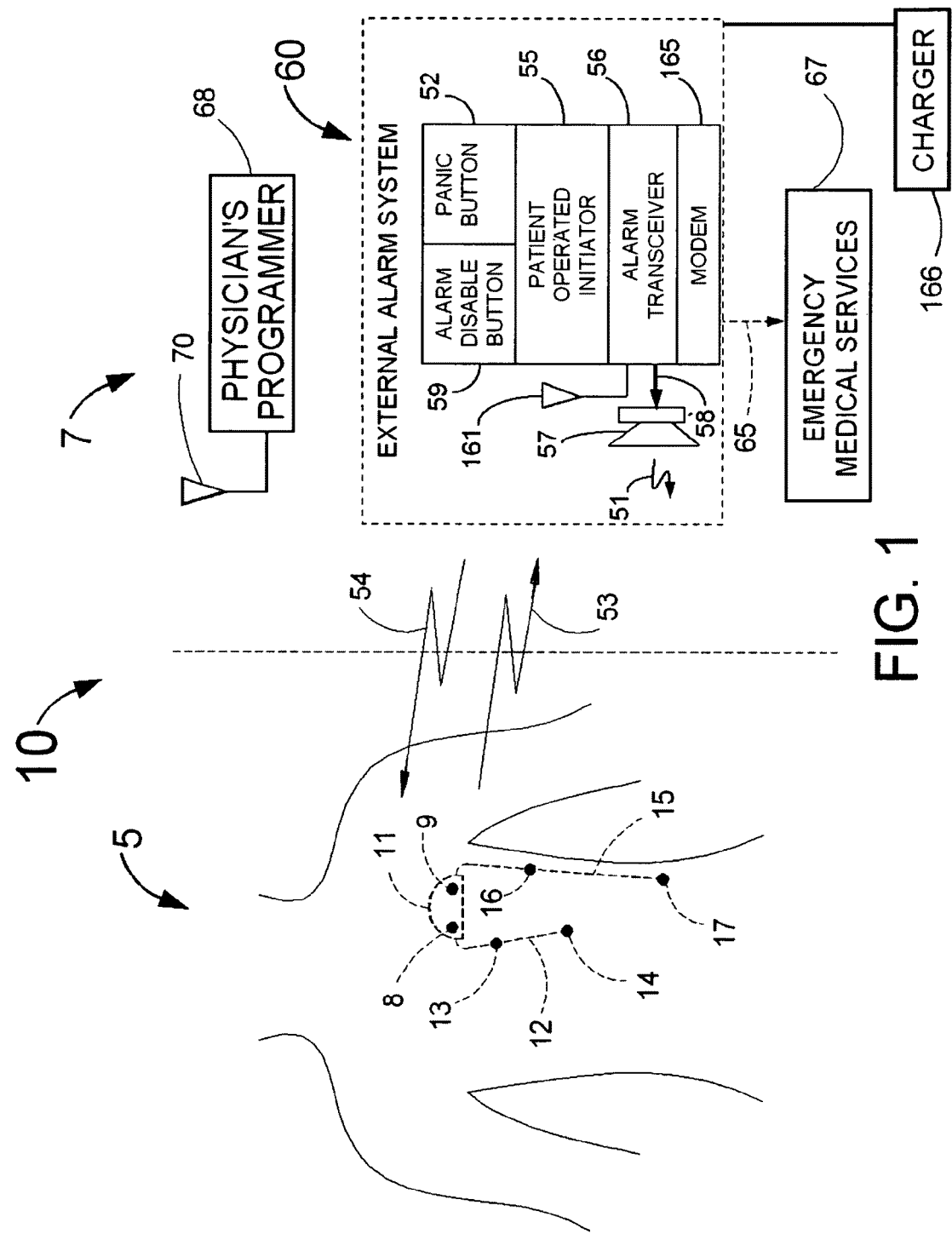
FIG. 1 illustrates a system for the detection of a cardiac event and for warning the patient that a cardiac event is occurring.

FIG. 1 illustrates one embodiment of the guardian system 10 consisting of an implanted cardiosaver 5 and external equipment 7. The battery powered cardiosaver 5 contains electronic circuitry that can detect a cardiac event such as an acute myocardial infarction or arrhythmia and warn the patient when the event occurs. The cardiosaver 5 can store the patient's electrogram for later readout and can send wireless signals 53 to and receive wireless signals 54 from the external equipment 7. The functioning of the cardiosaver 5 will be explained in greater detail with the assistance of FIG. 4.

The cardiosaver 5 has two leads 12 and 15 that have multi-wire electrical conductors with surrounding insulation. The lead 12 is shown with two electrodes 13 and 14. The lead 15 has subcutaneous electrodes 16 and 17. In fact, the cardiosaver 5 could utilize as few as one lead or as many as three and each lead could have as few as one electrode or as many as eight electrodes. Furthermore, electrodes 8 and 9 could be placed on the outer surface of the cardiosaver 5 without any wires being placed externally to the cardiosaver 5.

The lead 12 in FIG. 1 could advantageously be placed through the patient's vascular system with the electrode 14 being placed into the apex of the right ventricle. The lead 12 with electrode 13 could be placed in the right ventricle or right atrium or the superior vena cava similar to the placement of leads for pacemakers and Implantable Coronary Defibrillators (ICDs). The metal case 11 of the cardiosaver 5 could serve as an indifferent electrode with either or both electrodes 13 and/or 14 being active electrodes. It is also conceived that the electrodes 13 and 14 could be used as bipolar electrodes. Alternately, the lead 12 in FIG. 1 could advantageously be placed through the patient's vascular system with the electrode 14 being placed into the apex of the left ventricle. The electrode 13 could be placed in the left atrium.

The lead 15 could advantageously be placed subcutaneously at any location where the electrodes 16 and/or 17 would provide a good electrogram signal indicative of the electrical activity of the heart. Again for this lead 15, the case 11 of the cardiosaver 5 could be an indifferent electrode and the electrodes 16 and/or 17 could be active electrodes or electrodes 16 and 17 could function together as bipolar electrodes. The cardiosaver 5 could operate with only one lead and as few as one active electrode with the case of the cardiosaver 5 being an indifferent electrode. The system 10 described herein can readily operate with only two electrodes.

One embodiment of the cardiosaver device 5 using subcutaneous lead 15 would have the electrode 17 located under the skin on the patient's left side. This could be best located between 2 and 20 inches below the patient's left arm pit. The cardiosaver case 11 could act as the indifferent electrode and would typically be implanted under the skin on the left side of the patient's chest.

FIG. 1 also shows the external equipment 7 that consists of a physician's programmer 68 having an antenna 70, an external alarm system 60 including a charger 166. The external equipment 7 provides means to interact with the cardiosaver 5. These interactions include programming the cardiosaver 5, retrieving data collected by the cardiosaver 5 and handling alarms generated by the cardiosaver 5.

The purpose of the physician's programmer 68 shown in FIG. 1 is to set and/or change the operating parameters of the implantable cardiosaver 5 and to read out data stored in the memory of the cardiosaver 5 such as stored electrogram segments. This would be accomplished by transmission of a wireless signal 54 from the programmer 68 to the cardiosaver 5 and receiving of telemetry by the wireless signal 53 from the cardiosaver 5 to the programmer 68. When a laptop computer is used as the physician's programmer 68, it would require connection to a wireless transceiver for communicating with the cardiosaver 5. Such a transceiver could be connected via a standard interface such as a USB, serial or parallel port or it could be inserted into the laptop's PCMCIA card slot. The screen on the laptop would be used to provide guidance to the physician in communicating with the cardiosaver 5. Also, the screen could be used to display both real time and stored electrograms that are read out from the cardiosaver 5.

In FIG. 1, the external alarm system 60 has a patient operated initiator 55, an alarm disable button 59, a panic button 52, an alarm transceiver 56, an alarm speaker 57 and an antenna 161 and can communicate with emergency medical services 67 with the modem 165 via the communication link 65.

If a cardiac event is detected by the cardiosaver 5, an alarm message is sent by a wireless signal 53 to the alarm transceiver 56 via the antenna 161. When the alarm is received by the alarm transceiver 56 a signal 58 is sent to the loudspeaker 57. The signal 58 will cause the loudspeaker to emit an external alarm signal 51 to warn the patient that an event has occurred. Examples of external alarm signals 51 include a periodic buzzing, a sequence of tones and/or a speech message that instructs the patient as to what actions should be taken. Furthermore, the alarm transceiver 56 can, depending upon the nature of the signal 53, send an outgoing signal over the link 65 to contact emergency medical services 67. When the detection of an acute myocardial infarction is the cause of the alarm, the alarm transceiver 56 could automatically notify emergency medical services 67 that a heart attack has occurred and an ambulance could be sent to treat the patient and to bring him to a hospital emergency room.

If the remote communication with emergency medical services 67 is enabled and a cardiac event alarm is sent within the signal 53, the modem 165 will establish the data communications link 65 over which a message will be transmitted to the emergency medical services 67. The message sent over the link 65 may include any or all of the following information: (1) a specific patient is having an acute myocardial infarction or other cardiac event, (2) the patient's name, address and a brief medical history, (3) a map and/or directions to where the patient is located, (4) the patient's stored electrogram including baseline electrogram data and the specific electrogram segment that generated the alarm (5) continuous real time electrogram data, and (6) a prescription written by the patient's personal physician as to the type and amount of drug to be administered to the patient in the event of a heart attack. If the emergency medical services 67 includes an emergency room at a hospital, information can be transmitted that the patient has had a cardiac event and should be on his way to the emergency room. In this manner the medical practitioners at the emergency room could be prepared for the patient's arrival.

The communications link 65 can be either a wired or wireless telephone connection that allows the alarm transceiver 56 to call out to emergency medical services 67. The typical external alarm system 60 might be built into a Pocket PC or Palm Pilot PDA where the alarm transceiver 56 and modem 165 are built into insertable cards having a standardized interface such as compact flash cards, PCMCIA cards, multimedia, memory stick or secure digital (SD) cards. The modem 165 can be a wireless modem such as the Sierra AirCard 300 or the modem 165 may be a wired modem that connects to a standard telephone line. The modem 165 can also be integrated into the alarm transceiver 56.

The purpose of the patient operated initiator 55 is to give the patient the capability for initiating transmission of the most recently captured electrogram segment from the cardiosaver 5 to the external alarm system 60. This will enable the electrogram segment to be displayed for a medical practitioner.

Once an internal and/or external alarm signal has been initiated, depressing the alarm disable button 59 will acknowledge the patient's awareness of the alarm and turn off the internal alarm signal generated within the cardiosaver 5 and/or the external alarm signal 51 played through the speaker 57. If the alarm disable button 59 is not used by the patient to indicate acknowledgement of awareness of a SEE DOCTOR alert or an EMERGENCY alarm, it is envisioned that the internal and/or external alarm signals would stop after a first time period (an initial alarm-on period) that would be programmable through the programmer 68.

For EMERGENCY alarms, to help prevent a patient ignoring or sleeping through the alarm signals generated during the initial alarm-on period, a reminder alarm signal might be turned on periodically during a follow-on periodic reminder time period. This periodic reminder time is typically much longer than the initial alarm-on period. The periodic reminder time period would typically be 3 to 5 hours because after 3 to 5 hours the patient's advantage in being alerted to seek medical attention for a severe cardiac event like an AMI is mostly lost. It is also envisioned that the periodic reminder time period could also be programmable through the programmer 68 to be as short as 5 minutes or even continue indefinitely until the patient acknowledges the alarm signal with the button 59 or the programmer 68 is used to interact with the cardiosaver 5.

Following the initial alarm on-period there would be an alarm off-period followed by a reminder alarm on-period followed by an alarm off-period followed by another reminder alarm on-period and so on periodically repeating until the end of the periodic reminder time period.

The alarm off-period time interval between the periodic reminders might also increase over the reminder alarm on-period. For example, the initial alarm-on period might be 5 minutes and for the first hour following the initial alarm-on period, a reminder signal might be activated for 30 seconds every 5 minutes. For the second hour the reminder alarm signal might be activated for 20 seconds every 10 minutes and for the remaining hours of the periodic reminder on-period the reminder alarm signal might be activated for 30 seconds every 15 minutes.

The patient might press the panic button 52 in the event that the patient feels that he is experiencing a cardiac event. The panic button 52 will initiate the transmission from the cardiosaver 5 to the external alarm system 60 via the wireless signal 53 of both recent and baseline electrogram segments. The external alarm system 60 will then retransmit these data via the link 65 to emergency medical services 67 where a medical practitioner will view the electrogram data. The remote medical practitioner could then analyze the electrogram data and call the patient back to offer advice as to whether this is an emergency situation or the situation could be routinely handled by the patient's personal physician at some later time.

It is envisioned that there may be preset limits within the external alarm system 60 that prevent the patient operated initiator 55 and/or panic button from being used more than a certain number of times a day to prevent the patient from running down the batteries in the cardiosaver 5 and external alarm system 60 as wireless transmission takes a relatively large amount of power as compared with other functional operation of these devices.

Figure 2:
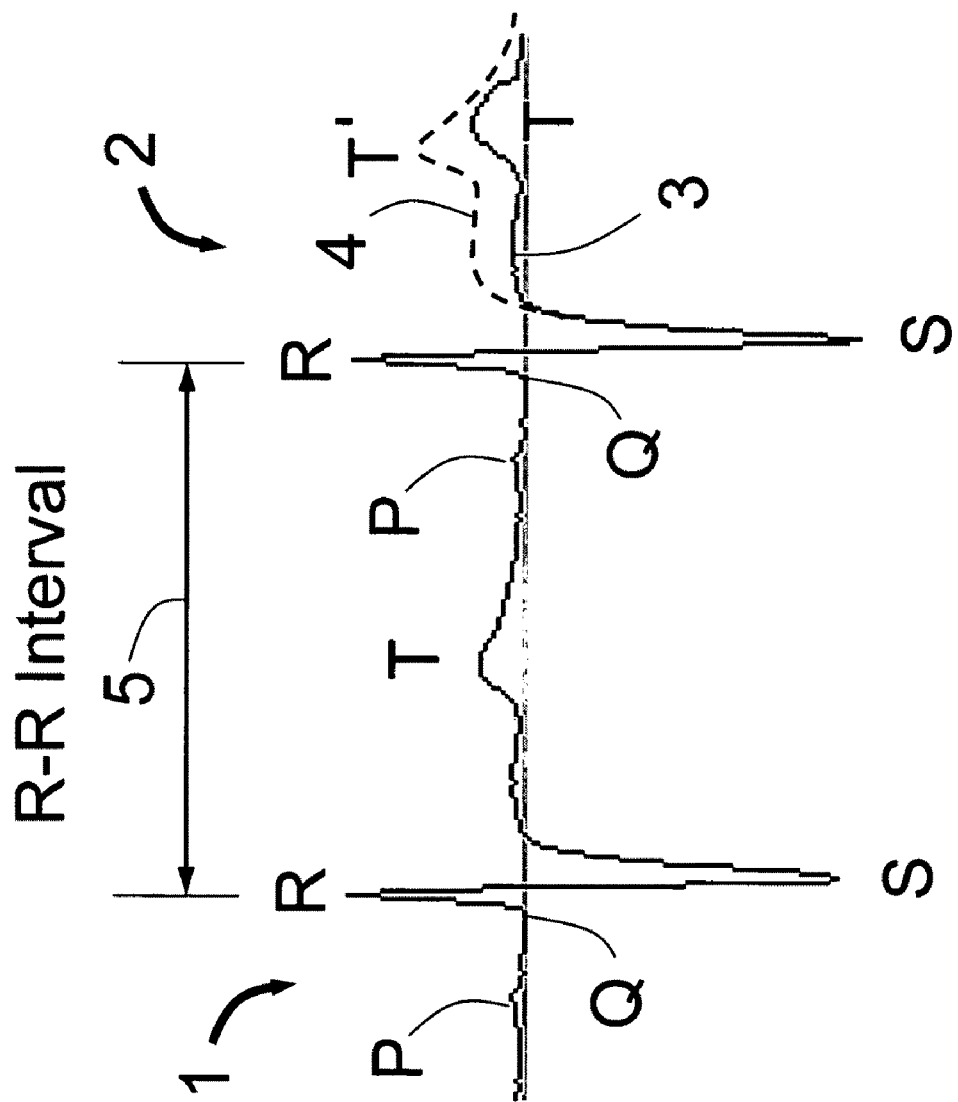
FIG. 2 illustrates a normal electrogram pattern and also shows a superimposed elevated ST segment that would be indicative of an acute myocardial infarction.
Figure 3:
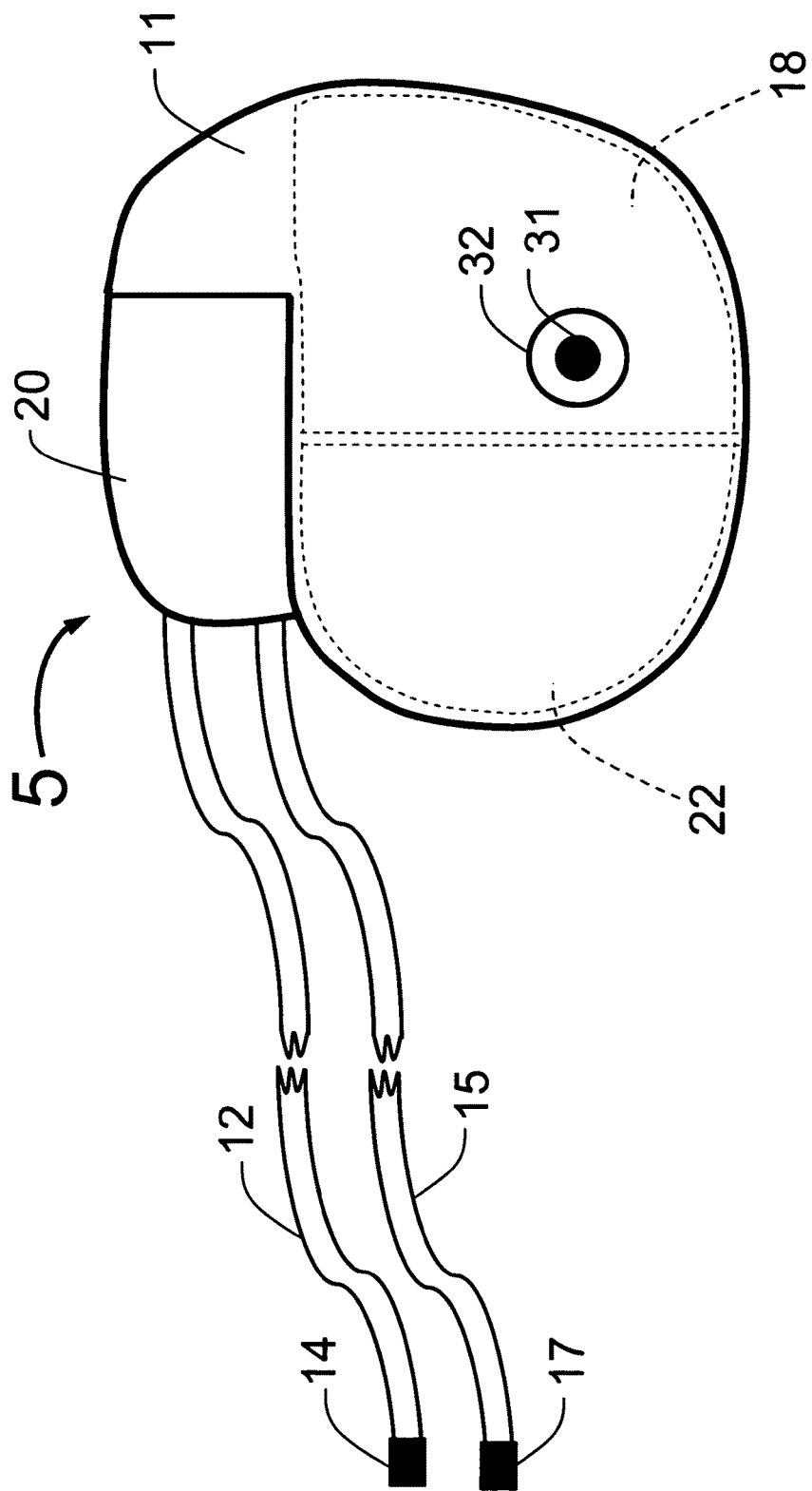
FIG. 3 is a plan view of the cardiosaver showing the cardiosaver electronics module and two electrical leads each having one electrode.

FIG. 2 illustrates a typical electrogram signal having beats 1 and 2 from some pair of implanted electrodes such as the electrode 14 and the case 11 of FIG. 3 overlaid with an electrogram having an elevated ST segment 4 (dashed line). The various portions of the electrogram are shown as the P, Q, R, S, and T waves. These are all shown as portions of a solid line in FIG. 2. The normal ST segment 3 of beat 2 is also shown in FIG. 2. The R-R interval 5 for beat 2 is shown as the time between the R waves of beat 2 and the beat before it (beat 1).

When an acute myocardial infarction occurs, there is typically an elevation (or depression) of the ST segment 4 as shown by the dashed line in FIG. 2. It is this shift of the ST segment 4 as compared to the baseline ST segment 3 that is a clear indicator that an acute myocardial infarction has occurred in a significant portion of the patient's myocardium.

Although an elevated ST segment 4 can be a good indicator of an acute myocardial infarction, other indicators such as a sudden change of heart rate or heart wall motion, intra-coronary blood pressure or a sudden decrease in blood $pO_2$ could also be used as independent sensing means or those signals could be used in addition to the voltage shift of the ST segment 4.

It is important to note that the electrogram from implanted electrodes may provide a faster detection of an ST segment shift as compared to an electrocardiogram signal obtained from skin surface electrodes. Thus the electrogram from implanted electrodes as described herein is the preferred embodiment of the present invention.

It is also well known that the T wave can shift very quickly when a heart attack occurs. It is envisioned that the present invention might detect this T wave shift as compared to a time of 1 to 5 minutes in the past.

It is anticipated that when a patient who has a stenosis in a coronary artery is performing a comparatively strenuous exercise his heart rate increases and he can develop exercise induced ischemia that will also result in a shift of the ST segment of his electrogram. This is particularly true for patients who have undergone balloon angioplasty with or without stent implantation. Such patients will be informed by their own physician that, if their cardiosaver 5 of FIG. 1 activates an alarm during exercise, that it may be indicative of the progression of an arterial stenosis in one of the heart's arteries. Such a patient would be advised to stop all exertion immediately and if the alarm signal goes away as his heart rate slows, the patient should see his doctor as soon as convenient. If the alarm signal does not go away as the patient's heart late slows down into the normal range then the cardiosaver will change the alarm signal to indicate that the patient should immediately seek medical care. As previously described, the cardiosaver 5 could emit a different signal if there is a heart attack as compared to the signal that would be produced if there were ischemia resulting from exercise.

It is also envisioned that heart rate and the rate of change of heart rate experienced during an ST segment voltage shift can be used to indicate which alarm should be produced by the cardiosaver 5. Specifically, an ST segment shift at a near normal heart rate would indicate an acute myocardial infarction. An ST segment shift when there is an elevated heart rate (e.g., greater than 100 bpm) would generally be indicative of a progressing stenosis in a coronary artery. In any case, if a sufficient ST segment shift occurs that results in an alarm from the cardiosaver 5, the patient should promptly seek medical care to determine the cause of the alarm.

It should be understood that, depending on a patient's medical condition, a vigorous exercise might be as energetic as running a long distance or merely going up a flight of stairs. After the cardiosaver 5 is implanted in a patient who has undergone a stent implant, he should have a stress test to determine his level of ST segment shift that is associated with the highest level of exercise that he can attain. The patient's heart rate should then be noted and the cardiosaver thresholds for detection, described with FIGS. 5 through 9, should be programmed so as to not alarm at ST segment shifts observed during exercise. Then if at a later time the patient experiences an increased shift of his ST segment at that pre-determined heart rate or within a heart rate range, then an alarm indicating ischemia can be programmed to occur. The occurrence of such an alarm can indicate that there is a progression in the narrowing of some coronary artery that may require angiography to determine if angioplasty, possibly including stent implantation, is required.

The alarm signal associated with an excessive ST shift caused by an acute myocardial infarction can be quite different from the "SEE DOCTOR" alarm means associated with progressing ischemia during exercise. For example, the SEE DOCTOR alert signal might be an audio signal that occurs once every 5 to 10 seconds. A different alarm signal, for example an audio signal that is three buzzes every 3 to 5 seconds, may be used to indicate a major cardiac event such as an acute myocardial infarction. Similar alarm signal timing would typically be used for both internal alarm signals generated by the alarm sub-system 48 of FIG. 4 and external alarm signals generated by the external alarm system 60.

In any case, a patient can be taught to recognize which signal occurs for these different circumstances so that he can take immediate response if an acute myocardial infarction is indicated but can take a non-emergency response if progression of the narrowing of a stenosis or some other less critical condition is indicated. It should be understood that other distinctly different audio alarm patterns could be used for different arrhythmias such as atrial fibrillation, atrial flutter, PVC's, PAC's, etc. A capability of the physician's programmer 68 of FIG. 1 would be to program different alarm signal patterns, enable or disable detection and/or generation of associated alarm signals in the cardiosaver for any one or more of these various cardiac events. Also, the intensity of the audio alarm, vibration or electrical tickle alarm could be adjusted to suit the needs of different patients. In order to familiarize the patient with the different alarm signals, the programmer 68 of the present invention would have the capability to turn each of the different alarm signals on and off.

FIG. 3 is a plan view of the cardiosaver 5 having a case 11 and a plastic header 20. The case 11 contains the primary battery 22 and the electronics module 18. This type of package is well known for pacemakers, implantable defibrillators and implantable tissue stimulators. Electrical conductors placed through the plastic header 20 connect the electronics module 18 to the electrical leads 12 and 15, which have respectively electrodes 14 and 17. The on-case electrodes 8 and 9 of FIG. 1 are not shown in FIG. 3. It should also be understood that the cardiosaver 5 can function with only two electrodes, one of which could be the case 11. All the different configurations for electrodes shown in FIGS. 1 and 3, such as the electrodes 8, 9, 13, 14, 16 or the metal case 11 are shown only to indicate that there are a variety of possible electrode arrangements that can be used with the cardiosaver 5.

On the metal case 11, a conducting disc 31 mounted onto an insulating disc 32 can be used to provide a subcutaneous electrical tickle to warn the patient that an acute myocardial infarction is occurring or to act as an independent electrode.

Figure 4:
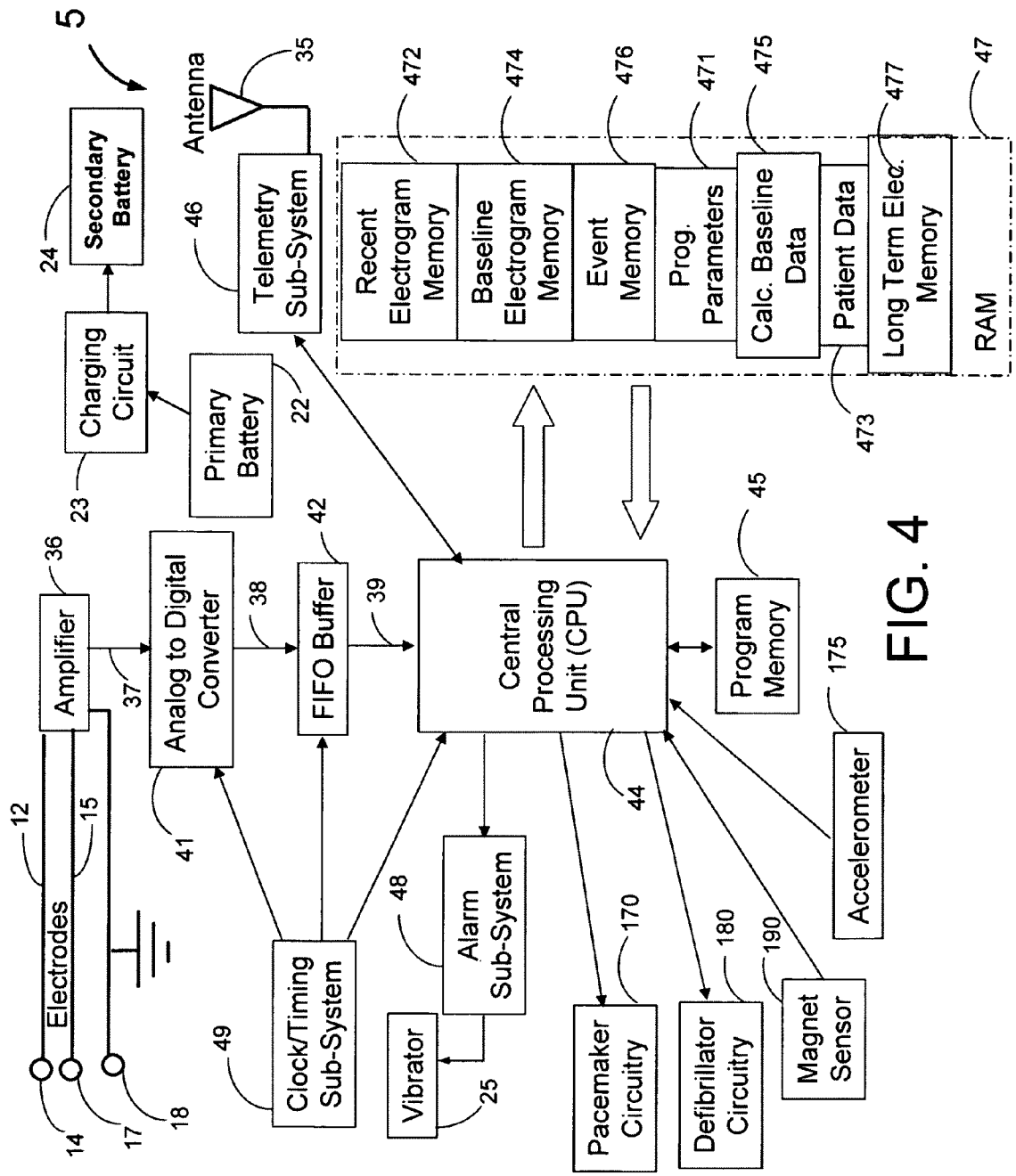
FIG. 4 is a block diagram of the cardiosaver.

FIG. 4 is a block diagram of the cardiosaver 5 with primary battery 22 and a secondary battery 24. The secondary battery 24 is typically a rechargeable battery of smaller capacity but higher current or voltage output than the primary battery 22 and is used for short term high output components of the cardiosaver 5 like the RF chipset in the telemetry sub-system 46 or the vibrator 25 attached to the alarm sub-system 48. An important feature of the present invention cardiosaver is the dual battery configuration where the primary battery 22 will charge the secondary battery 24 through the charging circuit 23. The primary battery 22 is typically a larger capacity battery than the secondary battery 24. The primary battery also typically has a lower self discharge rate as a percentage of its capacity than the secondary battery 24. It is also envisioned that the secondary battery could be charged from an external induction coil by the patient or by the doctor during a periodic check-up.

The electrodes 14 and 17 connect with wires 12 and 15 respectively to the amplifier 36 that is also connected to the case 11 acting as an indifferent electrode. As two or more electrodes 12 and 15 are shown here, the amplifier 36 would be a multi-channel amplifier. The amplified electrogram signals 37 from the amplifier 36 are then converted to digital signals 38 by the analog-to-digital converter 41. The digital electrogram signals 38 are buffered in the First-In-First-Out (FIFO) memory 42. Processor means shown in FIG. 4 as the central processing unit (CPU) 44 coupled to memory means shown in FIG. 4 as the Random Access Memory (RAM) 47 can process the digital electrogram data 38 stored the FIFO 42 according to the programming instructions stored in the program memory 45. This programming (i.e. software) enables the cardiosaver 5 to detect the occurrence of a cardiac event such as an acute myocardial infarction.

A clock/timing sub-system 49 provides the means for timing specific activities of the cardiosaver 5 including the absolute or relative time stamping of detected cardiac events. The clock/timing sub-system 49 can also facilitate power savings by causing components of the cardiosaver 5 to go into a low power standby mode in between times for electrogram signal collection and processing. Such cycled power savings techniques are often used in implantable pacemakers and defibrillators. In an alternate embodiment, the clock/timing sub-system can be provided by a program subroutine run by the central processing unit 44. In an advanced embodiment of the present invention, the clock/timing circuitry 49 would count for a first period (e.g. 20 seconds) then it would enable the analog-to-digital converter 41 and FIFO 42 to begin storing data, after a second period (e.g. 10 seconds) the timing circuitry 49 would wake up the CPU 44 from its low power standby mode. The CPU 44 would then process the 10 seconds of data in a very short time (typically less than a second) and go back to low power mode. This would allow an on off duty cycle of the CPU 44 which often draws the most power of less than 2 seconds per minute while actually collecting electrogram data for 20 seconds per minute.

In a preferred embodiment of the present invention the RAM 47 includes specific memory locations for 4 sets of electrogram segment storage. These are the recent electrogram storage 472 that would store the last 2 to 10 minutes of recently recorded electrogram segments so that the electrogram data leading in the period just before the onset of a cardiac event can be reviewed at a later time by the patient's physician using the physician's programmer 68 of FIG. 1. For example, the recent electrogram storage 472 might contain eight 10 second long electrogram segments that were captured every 30 seconds over the last 4 minutes.

The baseline electrogram memory 474 would provide storage for baseline electrogram segments collected at preset times over one or more days. For example, the baseline electrogram memory 474 might contain 24 baseline electrogram segments of 10 seconds duration, one from each hour for the last day, and information abstracted from these baselines.

A long term electrogram memory 477 would provide storage for electrograms collected over a relatively long period of time. In the preferred embodiment, every ninth electrogram segment that is acquired is stored in a circular buffer, so that the oldest electrogram segments are overwritten by the newest one. In an alternate embodiment, an externally programmable flag may be set to allow a continuous storage mode to be invoked according to which every electrogram segment is stored.

The event memory 476 occupies the largest part of the RAM 47. The event memory 476 is not overwritten on a regular schedule as are the recent electrogram memory 472 and baseline electrogram memory 474 but is typically maintained until read out by the patient's physician with the programmer 68 of FIG. 1. At the time a cardiac event like excessive ST shift indicating an acute myocardial infarction is detected by the CPU 44, all (or part) of the entire contents of the baseline and recent electrogram memories 472 and 474 would typically be copied into the event memory 476 so as to save the pre-event data for later physician review.

In the absence of events, the event memory 476 could be used temporarily to extend the recent electrogram memory 472 so that more data (e.g. every 10 minutes for the last 12 hours) could be held by the cardiosaver 5 of FIG. 1 to be examined by a medical practitioner at the time a patient visits. This would typically be overwritten with pre- and post-event electrogram segments following a detected event.

An example of use of the event memory 476 would have a SEE DOCTOR alert saving the last segment that triggered the alarm and the baseline used by the detection algorithm in detecting the abnormality. An EMERGENCY ALARM would save the sequential segments that triggered the alarm, a selection of other pre-event electrogram segments, or a selection of the 24 baseline electrogram segments and post-event electrogram segments. For example, the pre-event memory would have baselines from −24 hrs, −18, −12, −6, −5, −4, −3, −2 and −1 hours, recent electrogram segments (other than the triggering segments) from −5 minutes, −10, −20, −35, and −50 minutes, and post-event electrogram segments for every 5 minutes for the 2 hours following the event and for every 15 minutes after 2 hours post-event. These settings could be pre-set or programmable.

The RAM 47 also contains memory sections for programmable parameters 471 and calculated baseline data 475. The programmable parameters 471 include the upper and lower limits for the normal and elevated heart rate ranges, and physician programmed parameters related to the cardiac event detection processes stored in the program memory 45. The calculated baseline data 475 contain detection parameters extracted from the baseline electrogram segments stored in the baseline electrogram memory 474. Calculated baseline data 475 and programmable parameters 471 would typically be saved to the event memory 476 following the detection of a cardiac event. The RAM 47 also includes patient data 473 that may include the patient's name, address, telephone number, medical history, insurance information, doctor's name, and specific prescriptions for different medications to be administered by medical practitioners in the event of different cardiac events.

It is envisioned that the cardiosaver 5 could also contain pacemaker circuitry 170 and/or defibrillator circuitry 180 similar to the cardiosaver systems described by Fischell in U.S. Pat. No. 6,240,049.

The alarm sub-system 48 contains the circuitry and transducers to produce the internal alarm signals for the cardiosaver 5. The internal alarm signal can be a mechanical vibration, a sound or a subcutaneous electrical tickle or shock.

The telemetry sub-system 46 with antenna 35 provides the cardiosaver 5 the means for two-way wireless communication to and from the external equipment 7 of FIG. 1. Existing radiofrequency transceiver chip sets such as the Ash transceiver hybrids produced by RF Microdevices, Inc. can readily provide such two-way wireless communication over a range of up to 10 meters from the patient. It is also envisioned that short range telemetry such as that typically used in pacemakers and defibrillators could also be applied to the cardiosaver 5. It is also envisioned that standard wireless protocols such as Bluetooth and 802.11a or 802.11b might be used to allow communication with a wider group of peripheral devices.

A magnet sensor 190 may be incorporated into the cardiosaver 5. An important use of the magnet sensor 190 is to turn on the cardiosaver 5 on just before programming and implantation. This would reduce wasted battery life in the period between the times that the cardiosaver 5 is packaged at the factory until the day it is implanted.

The cardiosaver 5 might also include an accelerometer 175. The accelerometer 174 together with the processor 44 is designed to monitor the level of patient activity and identify when the patient is active. The activity measurements are sent to the processor 44. In this embodiment the processor 44 can compare the data from the accelerometer 175 to a preset threshold to discriminate between elevated heart rate resulting from patient activity as compared to other causes.

Figure 5:
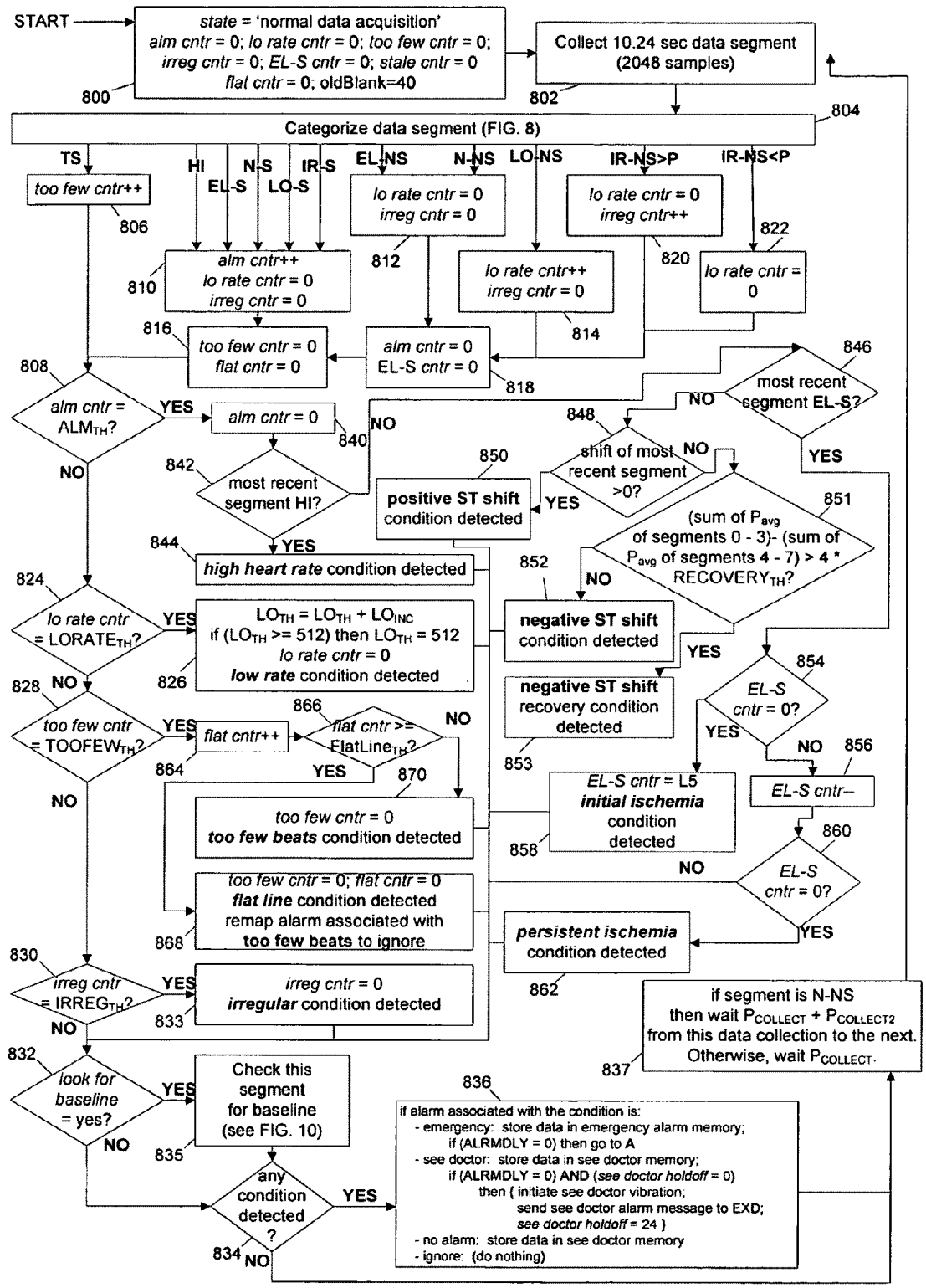
FIG. 5 is a block diagram of the cardiosaver event detection program.

FIG. 5 illustrates in the form of a block diagram the operation of the heart signal processing program 450 for cardiac event detection by the cardiosaver 5 of FIGS. 1-4. The heart signal processing program 450 is an example of one of many such detection programs whose instructions could reside in the program memory 45 for use by the CPU 44 of the cardiosaver 5 as shown in FIG. 4. The program shown in FIG. 5 is preferably run continuously. There is another routine, shown in FIG. 7, that preferably is run once per hour. The hourly routine stores various histogram data (see U.S. patent application Ser. No. 10/950,401, filed Sep. 28, 2004, entitled "Implantable system for monitoring the condition of the heart") and also operates in conjunction with the program shown in FIG. 5 to enable collection of baselines for each hourly period.

Turning to the program shown in FIG. 5, in block 800, various flags and counters, whose roles will be described further below, are initialized. In block 802, a data segment is captured into the FIFO buffer 42 of FIG. 4 and then transferred to the recent electrogram memory 472 of FIG. 4. The data segment is Y seconds long, where Y is preferably 10.24 sec., which corresponds to 2048 samples at a sampling rate of 200 Hz. Next, in block 804, which is described in detail with reference to FIG. 9, the acquired data segment is categorized as one of the following:

| Abbreviation | Description |
| --- | --- |
| HI | High Heart Rate |
| EL-S | Elevated Heart Rate with an ST Shift |
| EL-NS | Elevated Heart Rate with no ST Shift |
| N-S | Normal Heart Rate with an ST Shift |
| N-NS | Normal Heart Rate with no ST Shift |
| LO-S | Low Heart Rate with an ST Shift |
| LO-NS | Low Heart Rate with no ST Shift |
| IR-S | Irregular Heart Rate with an ST Shift |
| IR-NS>P | Irregular Heart Rate with no ST Shift with lots of short beats |
| IR-NS<P | Irregular Heart Rate with no ST Shift with few short beats |
| TS | Too Short (not enough "good" beats) |

If the segment has been categorized as "too short" (or TS), meaning that it does not have a sufficient number of acceptable beats, the program 450 moves to block 806, where the too few counter is incremented by 1. The program 450 then moves to block 808. As will be described further below, the too few counter tracks the number of consecutive (processed/categorized) segments that are "too short" for the purpose of generating an alarm in the case where there are so many consecutive TS segments that a medical or device problem is possible.

Returning to block 804, if the segment exhibits an ST shift or a high heart rate (HI, EL-S, N-S, LO-S or IR-S), an alarm counter (alm cntr) is incremented in block 810. Also in block 810, low heart rate (lo rate cntr) and irregular (irreg cntr) counters are set to 0. These counters track the number of consecutive segments characterized by low heart rates and irregular rhythms, respectively. (Even though one of the categories that results in a movement to block 810, LO-S, is associated with a low heart rate, the low rate counter is nonetheless set to 0 because that counter tracks the number of low heart rate segments that are not ST shifted.)

From block 810, the program 450 moves to block 816, where the toofew cntr and flat cntr counters are set to 0 because the current segment is not TS ("too short"). These counters work in tandem to determine the number of consecutively acquired "too short" segments. Thus, any segment that is acquired that is not "too short" will result in setting these counters back to 0.

Again returning to block 804, if the segment has been categorized as non-ST shifted and either elevated or normal heart rate (EL-NS or N-NS), the program 450 moves to block 812 and sets the rate cntr and irreg cntr to 0. From block 812, the program 450 moves to block 818, where the alm cntr is set to 0. The alm cntr variable tracks the number of consecutive segments that exhibit an ST shift or a high heart rate. Thus, this counter is reset to 0 when any segment is acquired that is not of that type. Similarly, the EL-S counter (EL-S cntr), which tracks the number of consecutive segments characterized by an elevated heart rate and ST shift, is reset to 0.

Again returning to block 804, if the segment is categorized as low heart rate with no ST shift (LO-NS), control is transferred to block 814, where the lo rate cntr is incremented and the irregular rhythm counter (irreg cntr) is reset to 0. From block 514, control is transferred to block 818.

Again returning to block 804, if the segment is characterized as having an irregular rhythm with too many short beats with no ST shift (IR-NS>P), control is transferred to block 820, where the rate cntr is reset to 0, and the irreg cntr is incremented. From block 820, control is transferred to block 818.

Again returning to block 804, if the segment is characterized as having an irregular rhythm with few short beats and not having an ST shift (IR-NS<P), control is transferred to block 822, where the lo rate cntr is reset to 0. From block 822, control is transferred to block 818.

All of the characterization and counter setting steps mentioned above eventually proceed to block 808, which checks whether the alarm counter (alm cntr) has reached the threshold ($ALM_{TH}$) needed for detection. $ALM_{TH}$ is preferably set to 3, which means that 3 consecutively processed/categorized segments must have been characterized as exhibiting an ST shift or a high heart rate before an event to said to be detected. Thus, an ST shift or a high heart rate condition must be somewhat persistent to trigger an event detection, which helps to avoid false positive detections.

$ALM_{TH}$ is a programmable parameter that could be increased to avoid false positive detections. With current average times from onset of a heart attack to arrival at a treatment center of 3 hours, a few minutes delay for a device that should enable the patient to easily reach a treatment center within 30 minutes is valuable if it improves the reliability of detection.

If the alm cntr has reached $ALM_{TH}$, the type of alarm to issue is determined, as will be further described below.

If alm cntr is less than $ALM_{TH}$, control passes to block 824, which checks whether the low rate counter (lo rate cntr) has reached the threshold ($LORATE_{TH}$) for detecting a low heart rate condition. If lo rate cntr has reached the threshold ($LORATE_{TH}$), then control passes to block 826, which adjusts the threshold ($LO_{TH}$) for detecting low heart rates (as will be further described with reference to FIG. 8) so that $LO_{TH}=LO_{TH}+LO_{INC}$ or 512, whichever is smaller. (Temporal quantities such as $LO_{TH}$ are expressed as a number of samples at a sampling rate of 200 Hz.)

Thus, for future segments, a lower heart rate is required to characterize a segment as a low heart rate segment. Both the initial $LO_{TH}$ (i.e. the $LO_{TH}$ that applies before the first segment is acquired after implantation) and $LO_{INC}$ are programmable. An initial $LO_{TH}$ value corresponding to approximately 50 beats/min (200*60/50 at a 200 Hz sampling rate) is preferred. A $LO_{INC}$ corresponding to approximately 5 beats/min (at 50 beats/min) is preferred.

The low rate counter (lo rate cntr) is reset and a low rate condition is detected. Control then passes to the baseline checking routine (block 832), which will be further described below.

Returning to block 824, if the low rate counter (lo rate cntr) is not less than $LORATE_{TH}$, control passes to block 828, which checks whether the "too few" beats counter (too few cntr) has reached the threshold ($TOOFEW_{TH}$) for detecting too few good beats. If so, the "too few" beat routine is invoked, starting at block 864, as will be further described below. If not, control passes to block 830, which checks whether the "irregular rhythm" segment counter (irreg cntr) has reached the threshold ($IRREG_{TH}$) for triggering an event for irregular beats. If so, control passes to block 833, which resets irreg cntr to 0 and sets a flag indicating that an irregular condition has been detected.

Control then passes to the baseline checking routine beginning at block 832. Control also passes to block 832 directly from block 830. Block 832 checks whether a baseline is desired by examining a look for baseline flag. Whether a baseline is desired, in turn, depends upon a number of factors. First, whether a baseline is desired depends on whether baselining is enabled, which is externally programmable. If baselining is not enabled, the look for baseline flag is set to 0 and does not change (unless and until baselining is reenabled.) If baselining is enabled, then the heart signal processing program 450 will try to find a baseline for each hourly period, starting at the beginning of the hourly period. If the heart signal processing program 450 has already found a baseline for the current hourly period, or if it has tried and failed to find a baseline for the current hourly period, then the look for baseline flag will have been set to 0 (as will be further described with reference to FIG. 12) and control will be passed to block 834. Otherwise, the present segment will be checked to determine whether it is a proper baseline segment according to the routine indicated by block 835 that is described further in FIG. 12. Control will then be passed to block 834.

Block 834 checks whether any condition has been detected with this segment. If not, control passes to block 837, which waits a certain amount of time before the next data segment is acquired in block 802. Specifically, if the current segment is normal and not ST shifted, then the program 450 waits for a relatively longer amount of time ($P_{COLLECT}+P_{COLLECT2}$) before acquiring the next segment, based on the assumption that when the patient is normal and has a normal heart rate, segments need not be taken as frequently to determine if the patient has or may develop a problem. In any other case, the program 450 waits for a relatively shorter amount of time ($P_{COLLECT}$) before acquiring the next segment. Preferred times for $P_{COLLECT}$ and $P_{COLLECT2}$ are 30 seconds and 60 seconds, respectively.

In an alternate embodiment, some other criteria apart from (or in addition to) time may determine the baseline acquisition time. Whether a baseline is desired depends on whether a baseline for the current period has already been found, or whether too many attempts have been made to find a baseline for the current period, as will be further described with reference to FIG. 12.

Returning to block 834, if a condition has been detected, control passes to block 836. In block 836, the routine checks what type of action should be taken when a particular condition has been detected. There are four possible actions which may generally be mapped by a medical practitioner to a particular condition: (1) generate an emergency alarm (and store data); (2) generate a "See Doctor" alert (and store data); (3) store data only; and (4) do nothing.

In block 836, if the condition is mapped to an emergency alarm, then the contents of the recent electrogram data storage 472, preferably 8 electrogram segments, is stored in the emergency alarm memory that is part of the event memory 476. This allows the patient's physician to review the electrogram segments collected during a period of time that occurred before the alarm, unless the data is overwritten by subsequent emergency alarm data. Also, a subset of the long term electrogram data in the long term electrogram memory 477 and the baseline electrogram memory 474 are written into the emergency alarm memory.

Data corresponding to the first emergency alarm is stored in the "emergency alarm memory-1" area of memory. If it is not the first emergency alarm, the data is stored in the "emergency alarm memory-2" area of memory. This approach means that if more than 2 emergency alarms are detected before a 'release memory' command is received, then the segments for the first (oldest) and the most recent (newest) are kept.

Because there is a possibility that segments from one or more emergency alarms may be lost with this approach, a counter of the number of emergency alarms since the last 'release memory' command was received, not shown in the figures, TOTEMER, is maintained.

After data is written to memory, if a counter ALARMDLY is 0, an emergency alarm is generated according to the alarm subroutine 490, which is described with reference to. FIG. 8. ALARMDLY, which is programmable, controls the duration that the device will not issue any alarms, regardless of whether it detects a condition. This counter is decremented every hour, as will be described with reference to FIG. 7.

In block 836, if the condition is mapped to "See Doctor Alert", a subset (preferably the most recent 3 segments) of the recent electrogram data 472 is stored in the appropriate place in "see doctor" memory. Also, the baseline electrogram memory 474 is written into the "see doctor" memory. There are 6 areas of "see doctor" memory that are used in a circular buffer. That is, if 7 see doctor alerts occur before a 'release memory' command is received, segments for the 2nd through the 7th are kept. If both ALARMDLY is 0 and see doctor holdoff are 0, then a "See Doctor Alert" vibration is generated by the alarm subroutine 490 described with reference to FIG. 8. The see doctor holdoff controls the amount of time after generation of a first "See Doctor Alert" that the next "See Doctor Alert" may be generated (if another "See Doctor Alert" type of condition is detected). This counter is decremented every hour, as will be described with reference to FIG. 7. It is reset to a default value of 24 (hours) after a "See Doctor Alert" is generated, which means that any "See Doctor Alert" type conditions that occur in the subsequent 24 hours will not result in the generation of a "See Doctor Alert."

If the condition is not mapped to an alarm but to only storing data, then the data is stored in the circular buffer "See Doctor" memory. However, no vibration is initiated. Finally, if the condition is mapped to nothing at all, it is simply ignored.

Returning to block 808, if the alarm counter=$ALM_{TH}$, a routine is invoked to classify the type of condition that caused the alarm counter to reach threshold. In block 840, the alarm counter (aim cntr) is reset to 0 and control passes to block 842, which checks whether the current electrogram segment is characterized by a high heart rate. If so, a high heart rate flag is set in block 844 and control then passes to block 832. If the segment is not associated with a high heart rate, block 842 transfers control to block 846, which checks whether the current electrogram segment is characterized as an elevated heart rate with an ST shift (EL-S). If not, control passes to block 848, which checks the polarity of the ST shift (i.e. greater than or less than 0). If so, a positive ST shift flag is set in block 850 and control is then transferred to block 832.

If the ST shift is negative, block 848 transfers control to block 851, which checks whether there has been a recent, substantial decrease in heart rate. The inventors have discovered that a delayed recovery of the ST segment, as measured by an intracardiac lead, may be indicative of chronic coronary ischemia as opposed to acute ischemia. (The delayed recovery of surface ST segments upon heart rate recovery is known to be a marker of chronic ischemia. Okin P M, Ameisen O, Kligfield P. *Identification of coronary artery disease by the rate-recovery loop. Circulation.* 1989 September; 80(3):53341.) Therefore, if a negative ST shift occurs (in a can-to-tip polarity), block 851 checks whether there has been a recent heart rate recovery. If so, a delayed recovery from exercise event (likely caused by chronic ischemia) is indicated in block 853 but otherwise a normal ST shift event (likely caused by acute ischemia) is indicated in block 852. (More generally, the ST shifts are categorized in blocks 852 and 853 according to whether a heart rate recovery has occurred.)

Block 851 assesses heart rate recovery according to the difference between the average heart rates in a recent group of segments (e.g. the last 4 segments) with a preceding group of segments (e.g. the $5^{th}$ through $8^{th}$ prior segments). This difference is compared to a threshold ($RECOVERY_{TH}$). Alternative schemes for handling heart rate recovery will be discussed in connection with FIGS. 18-20.

Returning to block 846, if the most recent segment is characterized as an elevated heart rate with an ST shift (EL-S), control basses to block 854. An elevated heart rate with an ST shift (EL-S) may be a result of exercise. To help avoid false positives, there are two conditions for ST shift with elevated heart rates: "initial ischemia" and "persistent ischemia". "Initial ischemia" is detected much like other conditions described above: a set of characteristics for a number of consecutive segments. "Persistent ischemia" is detected by detecting "initial ischemia" a number of consecutive times. For a particular example, in a preferred embodiment, 3 consecutive EL-S segments will generally be required to detect an "initial ischemia", while 21 consecutive EL-S segments will generally be required to detect a "persistent ischemia".

The 21 segment criterion is implemented by an EL-S counter (EL-S cntr), which is set to 7 after the "initial ischemia" is detected (first 3 EL-S segments), and decrementing this counter (in block 856) each time another consecutive "initial ischemia" is detected. (It is theoretically possible that 7 consecutive groups of 3 segments could give rise to "persistent ischemia" even though not all segments within each group is an EL-S. For example, if the pattern of N-S, N-S, EL-S were to repeat seven times, "persistent ischemia" would be detected. This would seem to be quite unlikely from a physiological standpoint.)

The above mentioned EL-S scheme is implemented by checking the value of the EL-S counter in block 854. If the counter is 0, then the current segment indicates the detection of "initial ischemia". If so, control is passed to block 858, where the EL-S counter is set to (preferably) 7. If the EL-S counter is not equal to 0, which indicates that a run of EL-S segments has been detected, the EL-S counter is decremented in block 856. Control then passes to block 860, which checks whether the EL-S counter is 0, which would signify a run of (preferably) 7 consecutive groups of 3 EL-S segments ("initial ischemia" detections). If so, then a "persistent ischemia" flag is set in block 862. Otherwise, no alarm for this segment is signified, and control passes to block 832.

Returning to block 828, if the too few cntr has reached the threshold for detecting a problem pertaining to a lack of detected heart beats, control passes from block 828 to block 864, where the flat line counter flat cntr) is incremented. As previously mentioned, this counter, along with too few cntr, keeps track of the number of consecutive segments with too few beats. Specifically, the number of consecutive segments with too few beats is equal to TOOFEW$_{TH}$*flat cntr+too few cntr. TOOFEW$_{TH}$ is preferably set to 4.

In block 866, the flat counter is compared to a threshold (FlatLine$_{TH}$), which is preferably equal to 3. If so, there has been a sufficient number of consecutive segments with too few beats to signify a flat line condition, and control passes to block, where flat cntr and too few cntr are reset, and a "flat line" flag is set to indicate a flat line condition. If flat cntr is less than FlatLine$_{TH}$, control passes to block 870, which resets too few cntr and sets a flag that signifies a "too few beats" condition.

Figure 6:
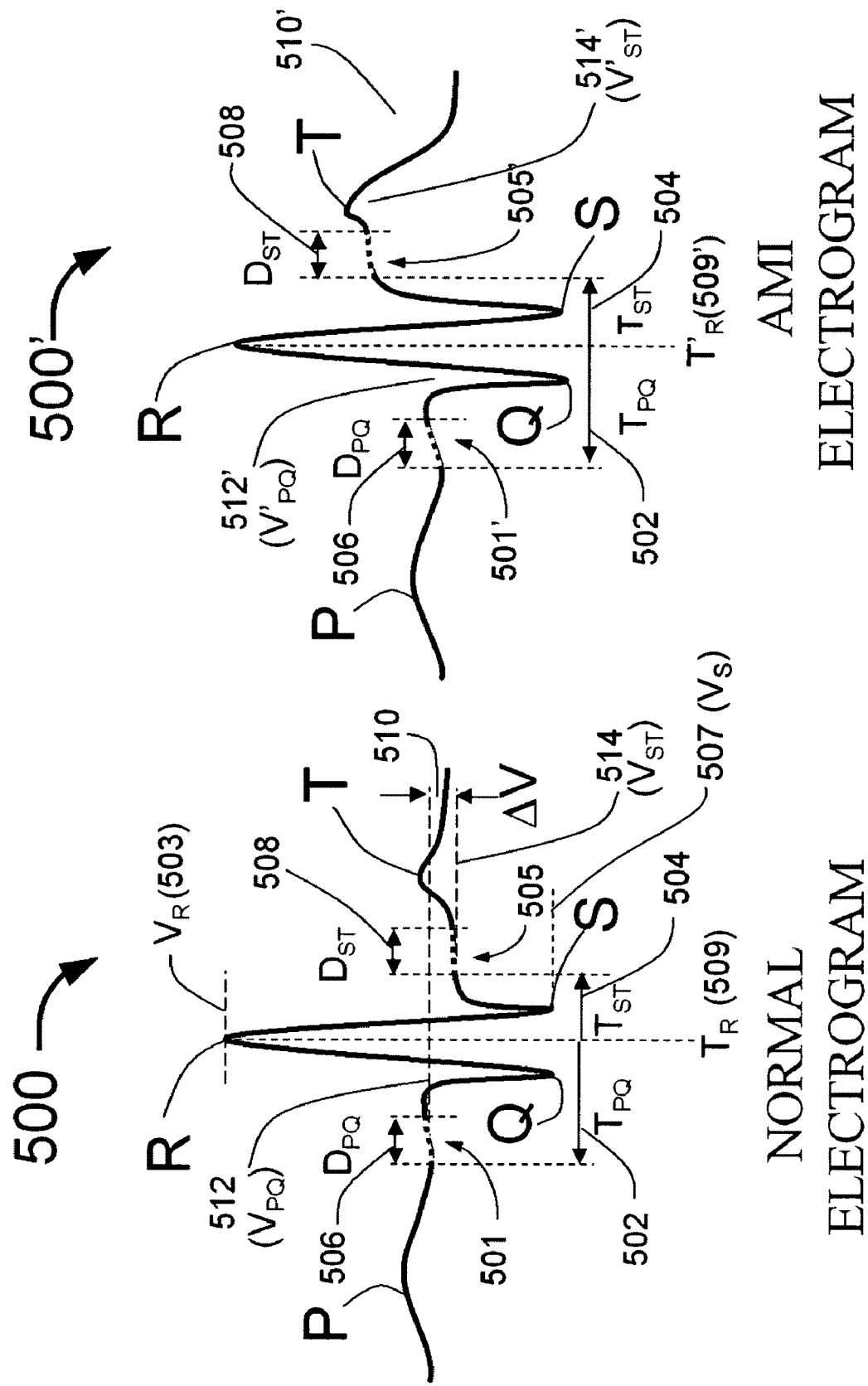
FIG. 6 illustrates the extracted electrogram segment features used to calculate ST shift.

FIG. 6 illustrates the features of a single normal beat 500 of an electrogram segment and a single beat 500' of an AMI electrogram segment that has a significant ST segment shifting as compared with the normal beat 500. Such ST segment shifting occurs within minutes following the occlusion of a coronary artery during an AMI. The beats 500 and 500' show typical heart beat wave elements labeled P, Q, R, S, and T. The definition of a beat such as the beat 500 is a sub-segment of an electrogram segment containing exactly one R wave and including the P and Q elements before the R wave and the S and T elements following the R wave.

For the purposes of detection algorithms, different sub-segments, elements and calculated values related to the beats 500 and 500' are hereby specified. The peak of the R wave of the beat 500 occurs at the time T$_R$ (509). The PQ segment 501 and ST segment 505 are sub-segments of the normal beat 500 and are located in time with respect to the time T$_R$ (509) as follows:

a. The PQ segment 501 has a time duration D$_{PQ}$ (506) and starts T$_{PQ}$ (502) milliseconds before the time T$_R$ (509).
b. The ST segment 505 has a time duration D$_{ST}$ (508) and starts T$_{ST}$ (502) milliseconds after the time T$_R$ (509).

The PQ segment 501' and ST segment 505' are sub-segments of the beat 500' and are located in time with respect to the time T'R (509') as follows:

c. The PQ segment 501' has a time duration D$_{PQ}$ (506) and starts T$_{PQ}$ (502) milliseconds before the time T'R (509').
d. The ST segment 505' has a time duration D$_{ST}$ (508) and starts T$_{ST}$ (502) milliseconds after the time T'R (509').

The ST segments 505 and 505' and the PQ segments 501 and 501' are examples of sub-segments of the electrical signals from a patient's heart. The R wave and T wave are also sub-segments. The dashed lines V$_{PQ}$ (512) and V$_{ST}$ (514) illustrate the average voltage amplitudes of the PQ and ST segments 501 and 505 respectively for the normal beat 500. Similarly the dashed lines V'PQ (512') and V'ST (514') illustrate the average amplitudes of the PQ and ST segments 501' and 505' respectively for the beat 500'. The "ST deviation" ΔV (510) of the normal beat 500 and the ST deviation ΔV$_{AMI}$ (510') of the AMI electrogram beat 500' are defined as:

$$\Delta V(510) = V_{ST}(514) - V_{PQ}(512)$$

$$\Delta V_{AMI}(510') = V'_{ST}(514') - V'_{PQ}(512')$$

Note that the both beats 500 and 500' are analyzed using the same time offsets T$_{PQ}$ and T$_{ST}$ from the peak of the R wave and the same durations D$_{PQ}$ and D$_{ST}$. In this example, the beats 500 and 500' are of the same time duration (i.e. the same heart rate). The parameters T$_{PQ}$, T$_{ST}$, D$_{PQ}$ and D$_{ST}$ would typically be set with the programmer 68 of FIG. 1 by the patient's doctor at the time the cardiosaver 5 is implanted so as to best match the morphology of the patient's electrogram signal and normal heart rate. V$_{PQ}$ (512), V$_{ST}$ (514), V$_R$ (503) and ΔV (510) are examples of per-beat heart signal parameters for the beat 500.

Figure 7:
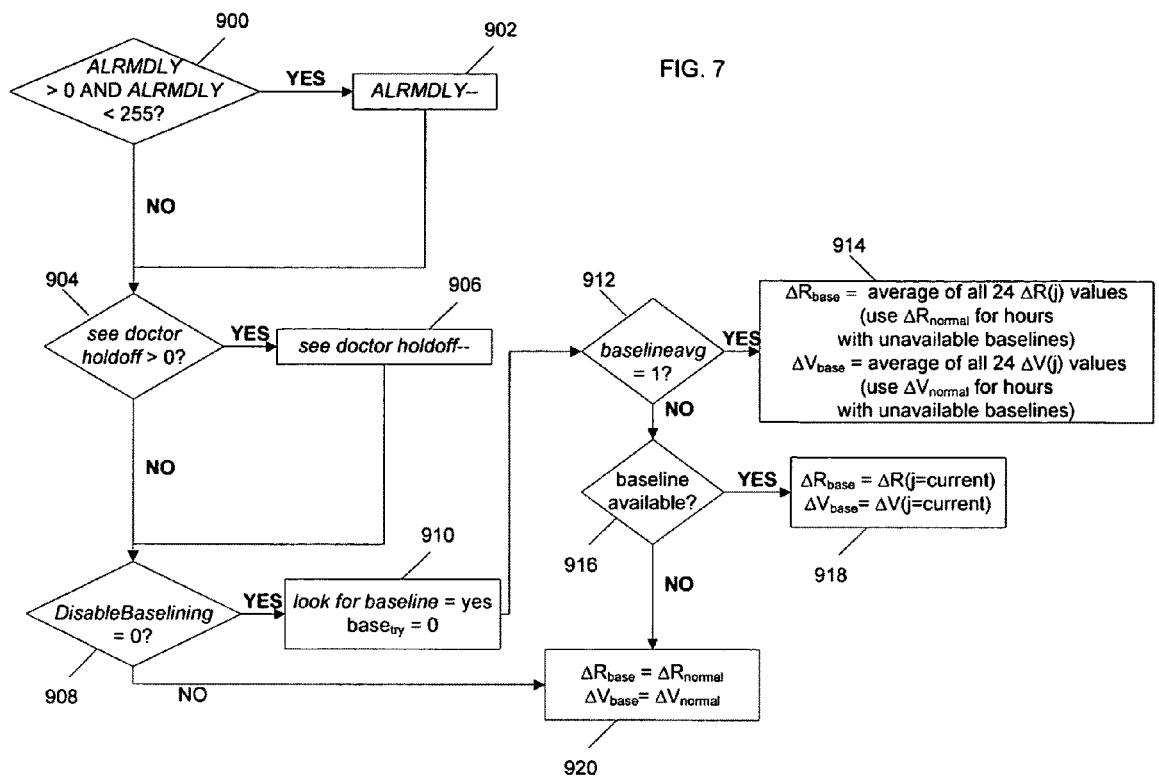
FIG. 7. is a block diagram of the hourly routine of the cardiosaver event detection program.
Figure 8:
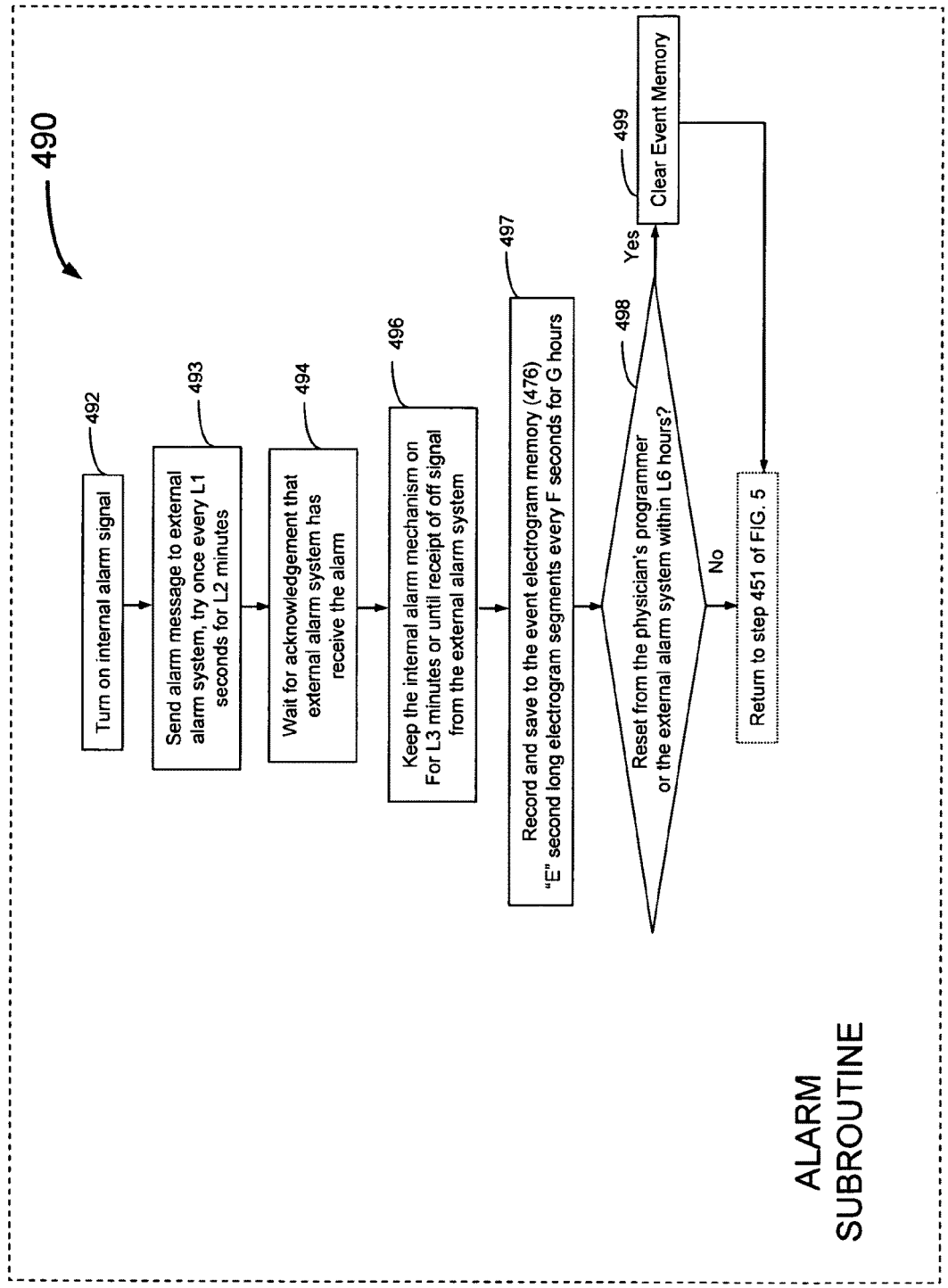
FIG. 8 is a block diagram of the alarm subroutine of the cardiosaver event detection program.

FIG. 7 illustrates a preferred embodiment of a periodically performed routine that is part of the program 450. The routine is run every Y minutes, with Y preferably set to 60 so that the routine is run once per hour. In block 900, the program 450 checks whether a timer, ALRMDLY, is between 0 and 255. This programmable timer allows alarms to be suppressed. If 0<ALRMDLY<255, then control passes to block 902, where ALRMDLY is decremented, such ALRMDLY keeps track of the number of hours before a detected condition should be allow to generate an alarm or alert vibration. (Vibrations are allowed only with ALRMDLY set equal to 0. Note that if ALRMDLY is 0 it is not changed: i.e. it remains at 0. However, also note that if ALRMDLY is equal to 255, it also is not changed, i.e. it remains at 255. ALRMDLY is set to 255 at the factory, preventing any vibrations while on the shelf prior to implantation.

From either block 900 or block 902, control passes to block 904, which checks whether the "see doctor holdoff" counter (see doctor holdoff) is greater than 0. This counter provides a means for preventing multiple "See Doctor" alerts within a 24 hour period. It is set to 24 (hours) after any "See Doctor" alert occurs, thus ensuring that any subsequent conditions mapped to a "See Doctor" alert will have their vibrations suppressed. If see doctor holdoff is greater than 0, control passes to block 906, where see doctor holdoff counter is decremented (by one hour).

The time that a "See Doctor" event occurs may also be examined to determine whether the event occurs during a preferably user programmable period (e.g. at night) during which the patient does not want to be disturbed by an alarm. The alarm may be delayed for an appropriate period of time.

From either block 904 or 906, control passes to block 908, which checks whether baselining is enabled. In some cases, it may be desirable to turn off baselining, which is accomplished by setting a flag, DisableBaselining, to 1. If baselining is not disabled, (i.e. DisableBaselining=0), control passes to block 910, which sets the look for baseline flag to "yes". As previously mentioned, this flag is checked in block 832 of FIG. 5 to determine whether a current segment should be checked as a candidate for a baseline. Also in block 910, the counter bases is set to 0. This counter tracks the number of unsuccessful attempts to obtain a baseline. If it reaches a certain threshold, as will be further described with reference to FIG. 12, then no further attempts are made to find a baseline for the current hourly period.

Control passes to block 912, where the baselineavg variable is examined. This variable, which is externally programmable, dictates whether the values that will be used for determining ST shifts are composed of an average of baseline values or a single baseline value. If baseline averaging is enabled, control passes to block 914, which averages the baseline heart signal parameters that are used to determine ST shifts. As will be described with reference to FIG. 10, a baseline ST-PQ value, shown as $\Delta V$ (510) in FIG. 6, is used to determine ST shifts. Also, a baseline R to PQ amplitude $\Delta R = V_R - V_{PQ}$ (see FIG. 6 for examples of $V_R$ and $V_{PQ}$) is used to determine ST shifts. In block 914, the baseline $\Delta V$ value that will be used to determine ST shifts, $\Delta V_{BASE}$, is set equal to the average $\Delta V$ of the most recent U baselines, $(1/U) \sum \Delta V(j)$, where U is preferably 24 and $\Delta V(j)$ is the $\Delta V$ of the j'th baseline. (When U is 24 and baselines are collected hourly, as is preferable, $\Delta V_{BASE}$ is the average over one day, or 24 hours.) Similarly, the baseline $\Delta R$ value that will be used to determine ST shifts, $\Delta R_{BASE}$, is set equal to $(1/U) \Sigma \Delta R(j)$, where U is again preferably equal to 24 and $\Delta R(j)$ is the $\Delta R$ of the j'th baseline.

It is possible that baselines for some time slots are non-existent or have become too old, in which case, as will be further described with reference to FIG. 12, default values $\Delta V_{normal}$ and $\Delta R_{normal}$ may be used as the $\Delta V(j)$ and $\Delta R(j)$ for those time slots j for which a baseline was found to be non-existant or too old. Conversely, if all baselines exist and are valid, so that no default values are used for any $\Delta V(j)$ or $\Delta R(j)$, then the default values $\Delta V_{normal}$ and $\Delta R_{normal}$ are preferably updated with the newly computed $\Delta V_{BASE}$ and $\Delta R_{BASE}$ values.

Instead of an average of the $\Delta V(j)$, some other statistical measure may be generated to compare against the current $\Delta V$. For example, a weighted average could be used whereby baselines corresponding to earlier time slots (e.g. >12 hours ago) are weighted more heavily than baselines corresponding to more recent time slots (e.g. <=12 hours ago). The exact nature of the averaging would depend on the expected normal rate of the change of $\Delta V$. Another alternative could involve taking the average of those $\Delta V(j)$ that fall within a standard deviation of the $\Delta V(j)$ distribution.

Returning to block 912, if baseline averaging is not enabled, control passes to block 916, which determines whether a baseline was collected U hours ago for the current hourly period. For example, if U is 24, and the hourly routine is run every hour on the hour, and it is currently 1:00 p.m., block 912 checks whether baseline values $\Delta V$ and AR for the 1:00 p.m. time slot are available, meaning that a baseline for that time slot was found fairly recently, preferably within the last three days (see FIG. 12 for more details). If so, in block 918, $\Delta V_{BASE}$ and $\Delta R_{BASE}$ are set equal to the $\Delta V$ and $\Delta R$ baseline values for the pertinent time slot (i.e. U hours ago). Otherwise, if baseline values $\Delta V$ and AR for that time slot are not available, default parameters $\Delta V_{normal}$ and $\Delta R_{normal}$ are used in block 620 for $\Delta V_{BASE}$ and $\Delta R_{BASE}$.

$\Delta V\_BASE$ and $\Delta R_{BASE}$, computed in blocks 914, 918 or 920, are stored in the calculated baseline data memory 475 of FIG. 4.

FIG. 8. illustrates a preferred embodiment of the alarm subroutine 490. The alarm subroutine 490 is run when there have been a sufficient number of events detected to warrant a major event cardiac alarm to the patient. The alarm subroutine 490 begins with step 491

Next; in step 492 the internal alarm signal is turned on by having the CPU 44 of FIG. 4 cause the alarm sub-system 48 to activate a major event alarm signal.

Next in step 493 the alarm subroutine instructs the CPU 44 to send a major event alarm message to the external alarm system 60 of FIG. 1 through the telemetry sub-system 46 and antenna 35 of the cardiosaver 5 of FIG. 4. The alarm message is sent once every L1 seconds for L2 minutes. During this time step 494 waits for an acknowledgement that the external alarm has received the alarm message. After L2 minutes, if no acknowledgement is received, the cardiosaver 5 of FIG. 1 gives up trying to contact the external alarm system 60. If an acknowledgement is received before L2 minutes, step 495 transmits alarm related data to the external alarm system. This alarm related data would typically include the cause of the alarm, baseline and last event electrogram segments and the time at which the cardiac event was detected.

Next in step 496, the cardiosaver 5 transmits to the external alarm system 60 of FIG. 1 other data selected by the patient's physician using the programmer 69 during programming of the cardiosaver. These data may include the detection thresholds $H_{ST}(i)$, $H_T(i)$ and other parameters and electrogram segments stored in the cardiosaver memory 47.

Once the internal alarm signal has been activated by step 492, it will stay on until the clock/timing sub-system 49 of FIG. 4 indicates that a preset time interval of L3 minutes has elapsed or the cardiosaver 5 receives a signal from the external alarm system 60 of FIG. 1 requesting the alarm be turned off.

To save power in the implantable cardiosaver 5, step 496 might check once every minute for the turn off signal from the external alarm system 60 while the external alarm system 60 would transmit the signal continuously for slightly more than a minute so that it will not be missed. It is also envisioned that when the alarm is sent to the external alarm system 60, the internal clock 49 of the cardiosaver 5 and the external alarm system 60 can be synchronized so that the programming in the external alarm system 60 will know when to the second, that the cardiosaver will be looking for the turn off signal.

At this point in the alarm subroutine 490 step 497 begins to record and save to event memory 476 of FIG. 4, an E second long electrogram segment every F seconds for G hours, to allow the patient's physician and/or emergency room medical professional to read out the patient's electrogram over time following the events that triggered the alarm. This is of particular significance if the patient, his caregiver or paramedic injects a thrombolytic or anti-platelet drug to attempt to relieve the blood clot causing the acute myocardial infarction. By examining the data following the injection, the effect on the patient can be noted and appropriate further treatment prescribed.

In step 498 the alarm subroutine will then wait until a reset signal is received from the physician's programmer 68 or the patient operated initiator 55 of the external alarm system 60 of FIG. 1. The reset signal would typically be given after the event memory 476 of FIG. 4 has been transferred to a component of the external equipment 7 of FIG. 1. The reset signal will clear the event memory 476 (step 499) and restart the main program 450 at step 800.

If no reset signal is received in L6 hours, then the alarm subroutine 490 returns to step 800 of FIG. 5 and the cardiosaver 5 will once again begin processing electrogram segments to detect a cardiac event. If another event is then detected, the section of event memory 476 used for saving post-event electrogram data would be overwritten with the pre-event electrogram data from the new event. This process will continue until all event memory is used. I.e. it is more important to see the electrogram data leading up to an event than the data following detection.

Figure 9:
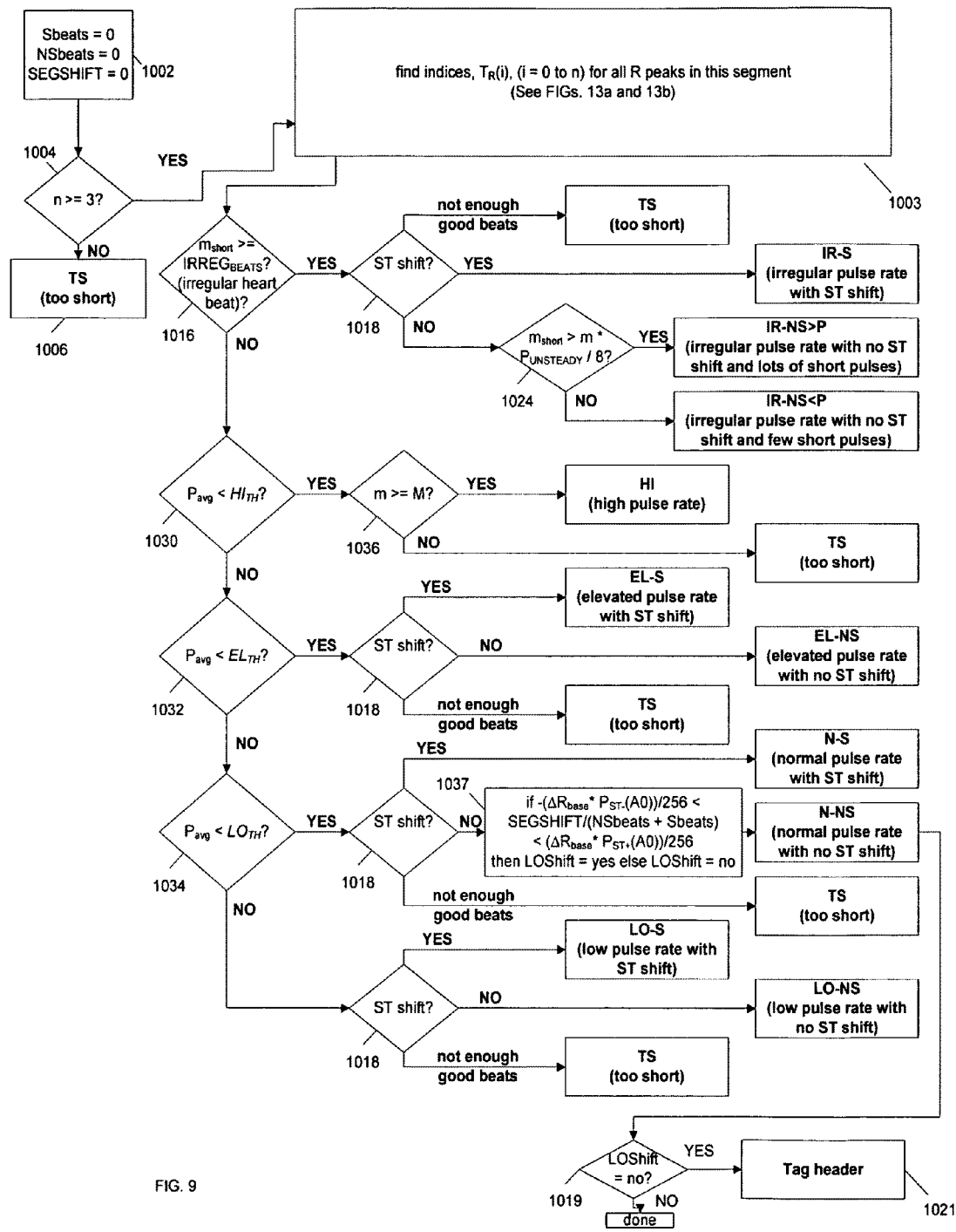
FIG. 9 is a block diagram of the data segment characterization subroutine of the cardiosaver event detection program.

FIG. 9 is a flow chart of the segment categorization routine of block 804 (FIG. 5). In block 1002, various variables (Sbeats, NSbeats and SEGSHIFT) are reset to 0. Sbeats and NSbeats track the number of ST shifted and non-ST shifted beats during a segment or run of segments. SEGSHFFT tracks the total sum of ST shifts during a segment or run of segments. These variables are reset to 0 in block 1002 because the previous segment was not too short.

Control transfers to block 1004, which checks whether the number of beats (n) in the segment is greater than or equal to 3. If not, the segment is too short, and is categorized as such in block 1006. As will be discussed below, the segment may be categorized as too short even if n>=3.

If n is greater than or equal to 3, as determined in block 1004, then control passes to block 1003, which assigns an index, ranging from 0 to n, to each R wave peak in the segment. The routine for locating R wave peaks is described with reference to FIGS. 13a and 13b. The R wave peak detection routine determines the number of irregular beats $m_{short}$ in the segment.

In block 1016, the number of irregular beats $m_{short}$ is compared to a threshold $IRREG_{BEATS}$. If $m_{short} > IRREG_{BEATS}$, the segment is either irregular or too short. To determine whether the segment too short, and also to determine whether the segment is ST shifted, control passes to the ST shift routine denoted by block 1018. This routine will be described further below with reference to FIG. 10. The ST shift routine 1018 may categorize the segment as too short or ST shifted, in which case the segment is too short (TS) or irregular with an ST shift (IR-S), respectively. If the ST shift routine 1018 determines that the segment is sufficiently long and not ST shifted, control passes to block 1024, which determines whether the segment has a relatively large number or relatively small number of "short" beats by comparing the number of short beats ($m_{short}$) with a programmable fraction $P_{UNSTEADY}/8$ of the total number of beats in the segment m. An exemplary value of $P_{UNSTEADY}$ is 2 (resulting in a fraction of 25%). If $m_{short} > m* P_{UNSTEADY}/8$, then the segment is categorized as irregular, non-ST shifted with a relatively large number of short beats (IR-NS>P). Otherwise, the segment is categorized as irregular, non-ST shifted with a relatively small number of short beats (IR-NS<P).

Returning to block 1016, if the number of irregular beats $m_{short}$ is less than $IRREG_{BEATS}$, so that the segment is not irregular, control passes to block 1030, which, along with blocks 1032 and 1034, categorizes the heart rate of the segment. These three blocks, 1030, 1032 and 1034, compare the average RR interval $P_{avg}$ to programmable thresholds $HI_{TH}$, $EL_{TH}$ and $LO_{TH}$, corresponding to high, elevated and low heart rates, respectively.

If the average RR interval suggests a high heart rate, block 1030 transfers control to block 1036, which determines if there are a sufficient number of beats in the segment by comparing the number of beats (m) with a programmable threshold M, which is preferably set to 6. This check is done to avoid characterizing a segment as a high heart rate segment based on only a few beats.

A segment with a low $P_{avg}$ may have only a few beats when for example, some actual heart beats are not detected and thus not included within the m beats. If m>=M, then the segment is characterized as a high heart rate segment (HI). Otherwise, it is categorized as too short (TS).

All other heart rate ranges (estimated by $P_{avg}$) are checked for ST shifts by the routine indicated by block 1018. In all of these heart rate types, elevated, normal, and low, the segment is placed into one of three categories depending upon whether the segment is ST shifted, and whether it is too short.

If the heart rate is normal, and the ST shift routine determines that the segment is not shifted and is not too short (i.e. the segment is N-NS), then an additional check is made in block 1037 to determine whether the segment might qualify as an acceptable baseline. (As will be described with reference to the baseline routine outlined in FIG. 12, only N-NS segments may serve as baselines.) Specifically, block 1037 checks whether the average ST shift of the segment is less than half of the positive and negative thresholds. If so, a flag, LOShift, which is used in the baseline routine as will be further described with reference to FIG. 12 and also examined in block 1019, is set to 1. If LOShift is set to 1, then block 1019 transfers control to block 1021, which tags the header to indicate that the segment is characterized by a LOShift condition. If LOShift is set to 0, then block 1019 ends the routine.

The gain of amplifier 36 and $LO_{TH}$ are preferably also stored with each segment so when segments before and after a gain change or automatic low threshold adjustment are in the same dataset, that fact can be noted.

Figure 10:
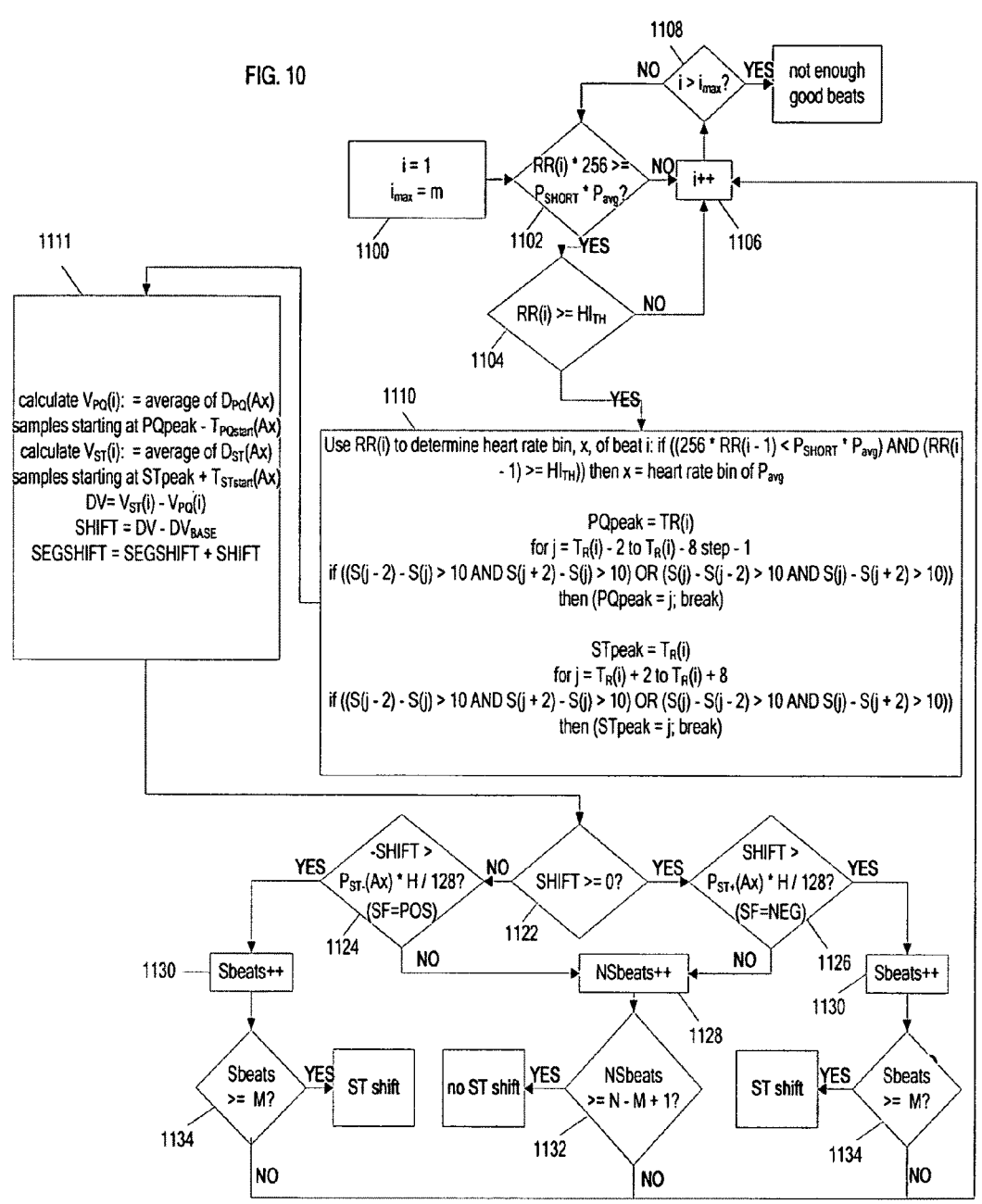
FIG. 10 is a block diagram of the ST shift subroutine of the cardiosaver event detection program.

FIG. 10 is a flow chart of the ST shift routine 1018. The ST shift detection routine checks beats that meet certain criteria for an ST shift ("ST analyzable beat"). The criteria a beat must meet in order to be checked for ST shift (i.e. to be an ST analyzable beat) are that the beat's period is not "too short" and not characterized by a high heart rate. The segment (which may be a compound segment) is declared to have an ST shift if M out of N "good" beats have an ST shift. The routine is structured to keep a running count of the number of beats with and without an ST shift. There are 3 possible outcomes: M beats with an ST shift are found before N−M+1 beats without an ST shift, N−M+1 beats without an ST shift are found before M beats with an ST shift, or the segment doesn't have ST analyzable beats for either of the previous conditions to be met. For example, the default values of M and N are 6 and 8, respectively. That means if 6 shifted beats are found before 3 non-shifted beats are found, the segment is declared to have an ST shift. Conversely, if 3 non-shifted beats are found before 6 shifted beats are found, the segment is declared to not have an ST shift. Note that this means (using these default values for M and N) that a determination can be made in as few as 3 ST analyzable beats and no more than 8 ST analyzable beats. This means that a segment with fewer than 8 ST analyzable beats may be TS (and a segment with 8 or more ST analyzable beats will never be TS).

Turning to FIG. 10, in block 1100, an index i is set equal to 1 to indicate processing will start with the first beat, and $i_{max}$, which the index can not exceed, is set equal to m, the number of beats to be analyzed.

In block 1102, the beat i is examined to determine whether its RR interval (i.e. the duration between beat i−1 and beat i) is too short. Beats associated with abnormal rhythms, as indicated by some heart rhythm parameter such as RR interval, may not represent a normal ST shift, and therefore it is preferable to exclude such beats from the segment for the purposes of analyzing ST shift. In addition, if a beat's RR interval is indicative of an abnormally high heart rate, it is also desirable to exclude the beat from ST shift determinations. If the RR interval (RR(i)) is too small according to a comparison with other beats in the segment ($P_{SHORT}*P_{avg}/256$), then block 1102 will exclude the beat from ST shift detection by passing control to block 1106, which increments i so that it points to the next beat. Control then transfers to block 1108, which checks if the last beat has been reached. If so, there are not enough good beats in the segment. (For segments with enough good beats, the logic of the ST shift routine 1018 is configured such that the routine exits before i reaches $i_{max}$.)

If the RR interval (RR(i)) is greater than or equal to ($P_{SHORT}*P_{avg}/256$) control passes to block 1104, which checks whether RR(i) is greater than or equal to the RR threshold $HI_{TH}$ used to detect a high heart rate condition (see block 1030 of FIG. 9). If RR(i) is less than this threshold, the beat is not analyzed and control passes to block 1106. Otherwise, control passes to block 1110, which performs a number of steps.

First, block 1110 selects the appropriate heart rate bin based on the RR interval. In the preferred embodiment, there are 5 different heart rate ranges that have corresponding ST shift thresholds and other parameters that govern the analysis of various portions of a beat. In particular, the start of the PQ segment, the duration of the PQ segment ($D_{PQ}$, in units of samples), the start of the ST segment, the duration of the ST segment ($D_{ST}$, in units of samples), and the fraction of baseline R to PQ amplitude ($\Delta R_{BASE} = V_{R,BASE} - V_{PQ,BASE}$) to use as positive and negative ST shift thresholds, respectively. These programmable parameters are listed in the table below.

| heart rate bin | min # of samples between peaks | max # of samples between peaks | start of PQ (samples before PQ peak) | duration of PQ (samples after start of PQ) | start of ST (samples after ST peak) | duration of ST (samples after start of ST) | fraction of average ($V_R - V_{PQ}$) for baseline to use as positive ST threshold | fraction of average ($V_R - V_{PQ}$) for baseline to use as negative ST threshold |
|---|---|---|---|---|---|---|---|---|
| A4 | $HI_{TH}$ | $A3_{TH} - 1$ | $T_{PQstart}(A4)$ | $D_{PQ}(A4)$ | $T_{STstart}(A4)$ | $D_{ST}(A4)$ | $P_{ST+}(A4)$ | $P_{ST-}(A4)$ |
| A3 | $A3_{TH}$ | $A2_{TH} - 1$ | $T_{PQstart}(A3)$ | $D_{PQ}(A3)$ | $T_{STstart}(A3)$ | $D_{ST}(A3)$ | $P_{ST+}(A3)$ | $P_{ST-}(A3)$ |
| A2 | $A2_{TH}$ | $A1_{TH} - 1$ | $T_{PQstart}(A2)$ | $D_{PQ}(A2)$ | $T_{STstart}(A2)$ | $D_{ST}(A2)$ | $P_{ST+}(A2)$ | $P_{ST-}(A2)$ |
| A1 | $A1_{TH}$ | $EL_{TH} - 1$ | $T_{PQstart}(A1)$ | $D_{PQ}(A1)$ | $T_{STstart}(A1)$ | $D_{ST}(A1)$ | $P_{ST+}(A1)$ | $P_{ST-}(A1)$ |
| A0 | $EL_{TH}$ | — | $T_{PQstart}(A0)$ | $D_{PQ}(A0)$ | $T_{STstart}(A0)$ | $D_{ST}(A0)$ | $P_{ST+}(A0)$ | $P_{ST-}(A0)$ |

In case a beat follows an ecoptic beat, in which case the RR(i) interval may be longer than expected, then the bin for the beat is selected as the average heart rate of the segment Pavg. A beat is determined to follow an ectopic beat the previous RR interval (RR(i−1)) was short but not too short, i.e., if ((256*RR(i−1)<PSHORT*Pavg) and (RR(i−1)>=$HI_{TH}$)).

To determine the starting point of the PQ segment, $T_{PQstart}$ (X) samples are counted back from the "PQ peak", where X is the heart rate bin (A0-A4). The PQ peak (labeled PQ peak in block 1110) is defined as the point nearest and before the R wave peak (which occurs at TR(i)) that is an inflection point, as determined by examining the slopes on either side of the point. If these slopes are both large and have the same sign, the point is the PQ peak. The search is started 2 samples to the left/before TR(i). If no sample that satisfies the inflection point criteria is found within 8 samples of TR(i), the search terminates and PQ peak is the R wave peak.

Analogously, the ST segment is referenced to the last major peak (STpeak) of the QRS complex, which is located in the same manner as the PQ peak, except that the search direction is to the right/after the R wave peak TR(i).

In an alternate embodiment, the heart rate bins for PQ/ST start and duration may be different, and preferably more granular, than the bins for determining ST shift.

In the discussion below, Ax refers to the heart rate bin corresponding to x. For example, $D_{PQ}(Ax)$ is the duration of the PQ segment, where Ax can be A0, A1, A2, A3 or A4.

Control passes from block 1110 to block 1111. In block 1111, the PQ segment voltage is calculated as $V_{PQ}(i)$=average value of $DpQ(Ax)$ samples starting at the sample defined by $T_R(i-(m-(n_p-1)))-T_{PQstart}(Ax)$. ($T_R$ is the number of the sample at which the peak of the R wave occurs.) Similarly, in block 1114, the ST segment voltage is calculated as $V_{ST}(i)$=average value of $D_{ST}(Ax)$ samples starting at the sample defined by $T_R(i-(m-(n_p-1)))+T_{STstart}(Ax)$.

Also in block 1111, the ST deviation ($\Delta V$ in FIG. 6) of the beat is calculated as $\Delta V = V_{ST}(i) - V_{PQ}(i)$. The ST shift, which compares the current ST deviation with the baseline ST deviation ($\Delta V_{BASE}$) is calculated as SHIFT=$\Delta V - \Delta V_{BASE}$. The cumulative ST shift for the entire segment is calculated by adding the current SHIFT to SEGSHIFT. (As mentioned, SEGSHIFT is used to compute the average ST shift for the beats in a segment that were analyzed for ST shift, as mentioned with reference to block 1037 in FIG. 9).

In block 1122, the polarity of the ST shift, positive or negative, is determined, so that different threshold tests can be applied depending on polarity, where the threshold tests indicate whether a beat is sufficiently shifted to be considered shifted. Beats with a shift greater than or equal to 0 are tested in block 1124 while negative shifted beats are tested in block 1126. In each case, the SHIFT is compared with a heart rate dependent fraction ($P_{ST+}(Ax)/128$ or $P_{ST-}(Ax)/128$) of the baseline R to PQ amplitude ($\Delta R_{BASE}$). $\Delta R_{BASE}$ serves as a proxy for signal strength, so a fraction of $\Delta R_{BASE}$ (i.e. $\Delta R_{BASE}*f$, where f is $P_{ST+}(AX)/128$ or $P_{ST-}(Ax)/128$) is the amplitude of ST shift that is considered above threshold given the current signal strength.

In an alternate embodiment, the segment is tagged with a variable SF as having either a positive shift (block 1124) or a negative shift (block 1126).

If the beat is below the ST shift threshold, the count of non-shifted beats (NSbeats) is incremented in block 1128. In block 1132, a test is performed to determine if the segment already has enough non-shifted beats to avoid being categorized as a shifted segment, regardless of whether any additional beats in the segment are shifted. Recalling that M out of N beats are required to categorize a segment as shifted, N−M+1 beats without an ST shift mean that the segment can not have M shifted beats and is thus not shifted. Thus, in block 1132, if NSbeats>=N−M+1, then the segment is not shifted, and the ST shift routine exits. Otherwise, the next beat is analyzed starting with block 1106.

If the shift of the beat is above the ST shift threshold as determined by blocks 1124 or 1126, the count of shifted beats (Sbeats) is incremented in block 1130. In block 1134, the number of shifted beats Sbeats is compared with M, the number of beats required to categorize a segment as shifted. If Sbeats>=M, then the segment is shifted and the ST shift routine exits. Otherwise, the next beat is analyzed starting with block 1106.

The above described structure of the ST shift routine ensures that segments with less than M beats, and having less than N−M+1 good beats, are categorized as too short. For example, if a segment consists of 5 shifted beats, it is not considered shifted because it has less than M (=6) shifted beats. When the routine reaches block 1108 after processing the fifth beat, it will categorize the segment as too short and exit. A subsequent segment (or segments) will be appended to the segment to create a compound segment that is long enough to categorize as shifted or non-shifted. The number of shifted and non-shifted beats (Sbeats and NSbeats) for the current segment as well as SEGSHIFT are stored and may be incremented while processing the subsequent segment. In this manner, the total number of shifted and non-shifted beats (and SEGSHIFT) in a compound segment are tracked as consecutive TS segments are processed sequentially. As mentioned, once a segment is sufficiently long to categorize for ST shift, the Sbeats, NSbeats and SEGSHIFT are reset to 0 in block 1002 (FIG. 9) for the next segment.

Figure 11:
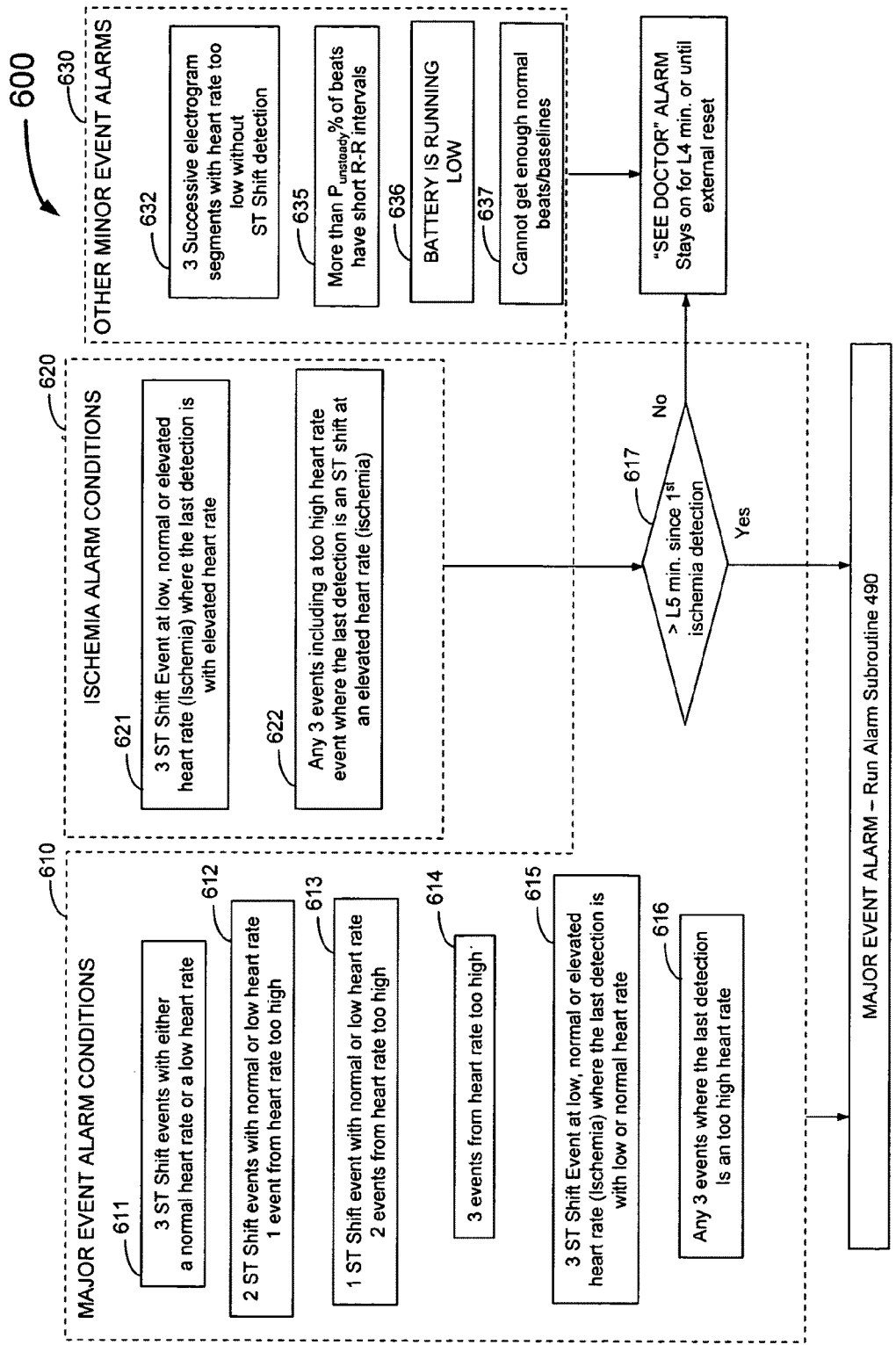
FIG. 11 diagrams the alarm conditions that are examples of the combinations of major and minor events that can trigger an internal alarm signal (and/or external alarm signal) for the system of FIG. 1.

FIG. 11 diagrams the alarm conditions 600 that are examples of the combinations of major and minor events that can trigger an internal alarm signal (and/or external alarm signal for the system of FIG. 1. Box 610 shows the combinations 611 through 617 of major cardiac events that can cause the alarm subroutine 490 to be run. These include the following:

611. 3 ST shift events (detections of excessive ST shift) with either a normal heart rate or a low heart rate.
612. 2 ST shift events with a normal or low heart rate and 1 event from heart rate too high.
613. 1 ST shift event with a normal or low heart rate and 2 events from heart rate too high.
614. 3 events from heart rate too high.
615. 3 ST shift events with either a normal; low or elevated heart rate (ischemia) where the last detection is at a normal or low heart rate.
616. 3 events (excessive ST shift or high heart rate) where the last event is high heart rate.
617. An ischemia alarm indication from conditions in box 620 that remains for more than L5 minutes after the first detection of ischemia.

The ischemia alarm conditions 620 include:

621. 3 ST shift events with either a normal, low or elevated heart rate (ischemia) where the last detection is at an elevated heart rate.
622. Any 3 events including a too high heart rate event where the last detection is an excessive ST shift at an elevated heart rate.

If either of the ischemia alarm conditions 620 is met and it is less than L5 minutes since the exercise induced ischemia was first detected, then the SEE DOCTOR ALERT signal will be turned on by step 682 of the ischemia subroutine 480 if it has not already been activated.

Box 630 shows the other minor event alarm conditions including the bradycardia alarm condition 632 that is three successive electrogram segments collected with heart rate too low and the unsteady heart rate alarm condition 635 that is caused by more than $P_{unsteady}$ % of beats having a too short R-R interval.

These will trigger the SEE DOCTOR alert signal initiated by step 427 of the hi/low heart rate subroutine 420 for the bradycardia alarm condition 632 and step 416 of the unsteady hart rate subroutine 410 for the unsteady heart rate alarm condition 635. Also triggering the SEE DOCTOR alert signal is a low battery condition 636.

Figure 12:
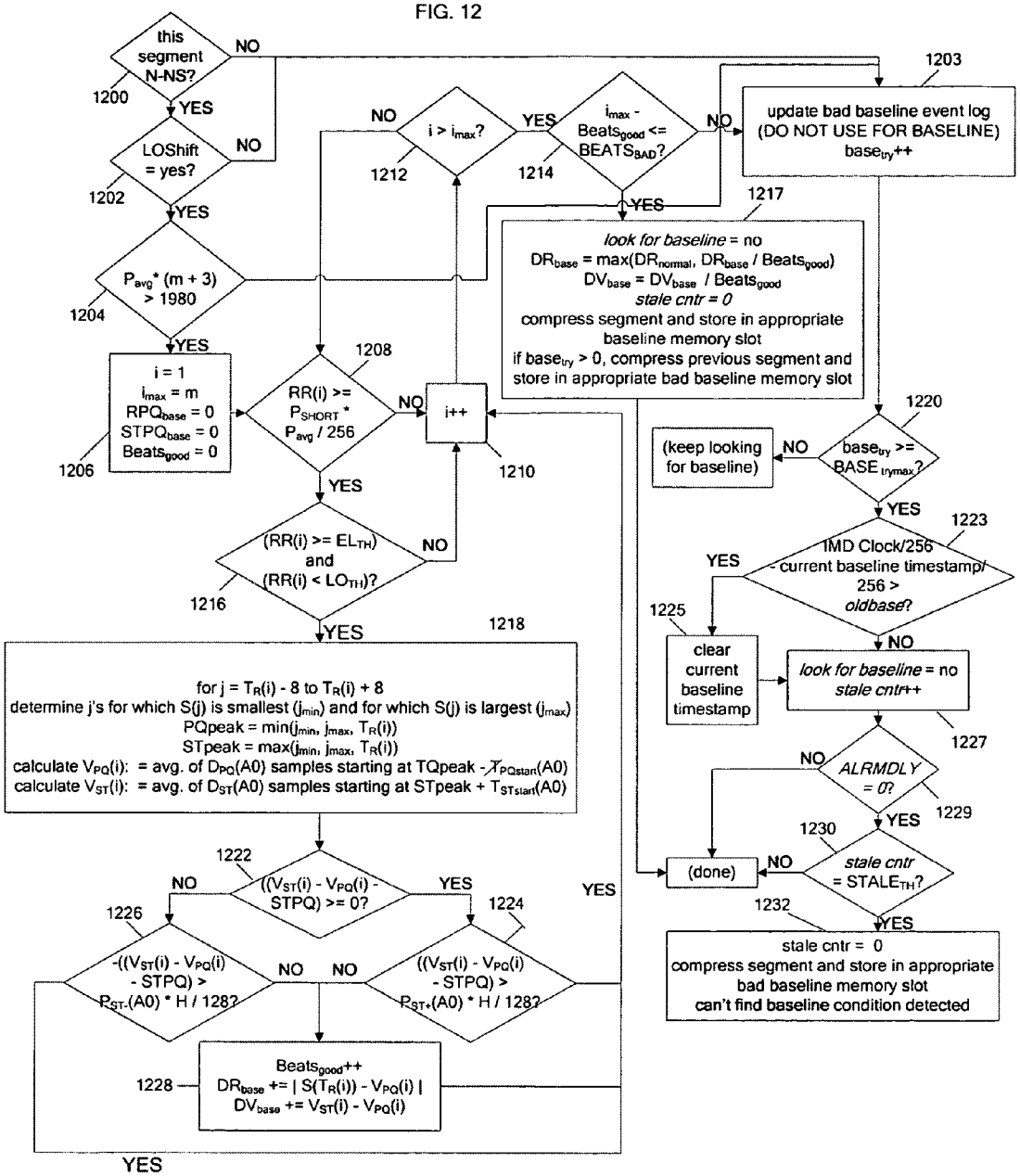
FIG. 12 is a block diagram of the baseline parameter extraction subroutine of the cardiosaver event detection program.

FIG. 12 is a flow chart of procedure that checks whether a segment qualifies as a baseline and, if so, calculates the baseline quantities $\Delta R(j)$ and $\Delta V(j)$, where j indexes the current time slot (i.e. one of 24 hours if baselines are acquired hourly)

In block 1200 the program 450 checks whether the segment was classified as having a normal heart rate and no ST shift (N-NS). If not, the segment can not be a baseline and, as will be further described below, various checks are made to determine if too many unsuccessful attempts have been made to find a baseline, which may indicate an alarmable condition.

Otherwise, if the segment is N-NS, additional preliminary checks are made to determine whether the segment may qualify as a baseline. In block 1202, if the LOSHIFT variable has been set in block 1037 of FIG. 9), which indicates that the segment is somewhat ST shifted but not enough to be considered a physiological problem, the segment can not qualify as a baseline. If LOSHIFT has not been set, control passes to block 1204. There a check is made to make sure that segment being examined has beats through out the segment. (That is, a segment with 5 beats in the first 5 seconds of the segment and no beats in the second 5 seconds of the segment should not be used as a baseline segment. Formally, this check is performed by comparing($P_{avg}$*(m+3)>1980).

If the segment is not disqualified by the preliminary tests in blocks 1200, 1202 and 1204, each beat in the segment is checked in a manner similar to the ST shift routine, the major difference being that N-M+1 beats good, non-shifted beats does not necessarily qualify a segment as a baseline. Instead, a more stringent test, which requires that the total number of "bad beats" be below a threshold ($BEATS_{BAD}$) is applied. Also, in the baseline routine, running totals of the R to PQ height ($V_R$-$V_{PQ}$) and ST deviation are kept so that the $\Delta R(j)$ and $\Delta V(j)$ quantities can be calculated for the segment if it qualifies as a baseline.

In block 1206, as in the ST shift routine, the beat index i is set to 1, $i_{max}$ is set to m. In addition, $RPQ_{base}$, $STPQ_{base}$ and $Beats_{good}$ variables are set to 0. $RPQ_{base}$ and $STPQ_{base}$ are running totals of the R to PQ height ($V_R$-$V_{PQ}$ in FIG. 6) and ST deviation ($\Delta V$ in FIG. 6). $Beats_{good}$ is the total number of good, non-shifted beats. In block 1208, the beat referenced by i is checked to determine whether it is too short by comparing its RR interval with $P_{SHORT}$/256*$P_{avg}$. If the RR interval (RR(i)) is too small according to a comparison with other beats in the segment ($P_{SHORT}$*$P_{avg}$/256), thereby indicating a short beat, the beat is not analyzed for an ST shift. Control passes to block 1210, which increments i so that it points to the next beat. Control then transfers to block 1212, which checks if the last beat has been reached. If so, control transfers to block 1214, which will be further described below. Otherwise, control returns to block 1208.

Returning to block 1208, if the RR interval (RR(i)) is greater than or equal to $P_{SHORT}$/256*$P_{avg}$, the beat is then checked to see if it is in the normal heart rate bin. In block 1216, RR(i) is compared to the threshold RR intervals for low heart rate ($EL_{TH}$) and elevated heart rate ($LO_{TH}$), respectively, to ensure that the beat (i) is in the normal range. If the RR interval is too short or too long (i.e. the instantaneous heart rate is too high or too low, respectively), the beat is not analyzed for ST shift and control transfers to block 1210.

Otherwise, in block 1218, the PQ segment voltage is calculated as $V_{PQ}(i)$=average value of $D_{PQ}(A0)$ samples starting at the sample defined by TQpeak-$T_{PQstart}(A0)$. (The value of TQpeak was described with reference to block 1110 of FIG. 10.) Similarly, the ST segment voltage is calculated as $V_{ST}(i)$=average value of $D_{ST}(A0)$ samples starting at the sample defined by STpeak+$T_{STstart}(A0)$. (The value of STpeak was described with reference to block 1110 of FIG. 10.)

In block 1222, the polarity of the beat i's ST shift, positive or negative, is determined, so that different threshold tests can be applied depending on polarity. As in the ST shift routine, the ST shift is $V_{ST}(i)$-$V_{PQ}(i)$-$\Delta V_{BASE}$. Positive (or non-shifted) beats are tested in block 1224 while negative shifted beats are tested in block 1226. As in the ST shift routine, the ST shift is compared with a fraction ($P_{ST}$+(A0)/128 or $P_{ST}$-(A0)/128) of the baseline R to PQ amplitude ($\Delta R_{BASE}$).

If the beat's ST shift is below the positive or negative threshold (whichever applies), in block 1228, the beat's R to PQ height ($V_{PQR}$=|$V(T_R(i))$-$V_{PQ}(i)$|) is added to the running total $RPQ_{base}$ and the beat's ST deviation ($V_{ST}(i)$-$V_{PQ}(i)$) is added to $STPQ_{base}$. Also, the $Beats_{good}$ counter, which tracks the number of good, non-ST shifted beats, is incremented. Control then transfers back to block 1210.

Returning to block 1224 or block 1226, whichever applies, if the beat's ST shift is above the positive or negative threshold (whichever applies), the beat is effectively excluded from the segment by skipping block 1228. Specifically, control is transferred to block 1210.

Moving forward to block 1214, if the number of bad beats ($=i_{max}-\text{Beats}_{good}$) is less than or equal to a threshold, ($\text{BEATS}_{BAD}$), preferably set to 1, then the segment qualifies as a baseline and control passes to block 1217. The "look for baseline" flag is set to 0 since the baseline has been found. The average $\Delta R$ for the segment is set equal to $\text{RPQ}_{base}/\text{Beats}_{good}$. However, if this value is too small, it will not be used as $\Delta R(j)$ for the time slot because small values of AR can bias checks for ST shifts. Specifically, in both the ST shift routine and the baseline routine, ST shifts are determined by comparing ST deviations with a threshold defined by a fraction of baseline $\Delta R_{BASE}$. Thus, if $\Delta R_{BASE}$ was very small, then the threshold may be very small. Consequently, small ST shifts could be above threshold, which is not desirable. To avoid this problem, $\Delta R(j)$ for any time slot is never allowed to be smaller than a parameter $\text{RPQ}_{normal}$, which is preferably equal to 100.

The baseline's ST devation $\Delta R(j)$ is set equal to the average ST deviation for the good beats in the segment $S_{TPQ}/\text{Beats}_{good}$. A counter (stale cntr) which keeps track of how many consecutive hours a new baseline has not been found, is reset to 0. The segment is compressed, preferably according to the turning point algorithm, and stored in an appropriate baseline memory slot. If this segment is not the first segment in the hour to be checked, then a counter $\text{base}_{try}$ will be greater than 0, in which case the previous segment is compressed and stored in an appropriate slot for bad baselines. (The operation of the counter $\text{base}_{try}$ will be further described below.) From block 1217, the baseline checking routine exits.

Returning to block 1214, if the number of bad beats ($=i_{max}-\text{Beats}_{good}$) is greater than $\text{BEATS}_{BAD}$, then the segment is disqualified as a baseline and control passes to block 1203, where a bad baseline event log is updated. Also, the counter $\text{base}_{try}$, which tracks the number of unsuccessful attempts made to find a baseline, is incremented. Control passes to block 1220, which checks whether the number of unsuccessful attempts made to find a baseline ($\text{base}_{try}$) exceeds a threshold $\text{BASE}_{trymax}$.

If not, the routine simply exits. Otherwise, control passes to block 1223, which checks how long ago the existing baseline for the current time slot was acquired. Specifically, the time that a good baseline for the current time period was found (current baseline timestamp) is subtracted from the current time kept by the clock 49 (see FIG. 4). If this difference is too large, as measured by a threshold oldbase which is preferably set to 84 hours (3.5 days), then the baseline is considered too old and is discarded. Instead, as mentioned in connection with blocks 914 and 920 in FIG. 7, default parameters $\Delta V_{normal}$ and $\Delta R_{normal}$ will used in block 620 for $\Delta V_{BASE}$ and $\Delta R_{BASE}$ until such time as a baseline segment is found for this time slot. In block 1225, the baseline's time stamp is cleared (effectively discarding it).

From either block 1225 or block 1223, control transfers to block 1227 which sets the look for baseline flag to "no" to indicate that no further attempts should be made to find a baseline for the current time slot. The stale cntr, which keeps track of the number of consecutive time slots which have had unsuccessful attempts to find a baseline, is incremented.

Inability to collect baselines (a "can't find baseline" condition) may arise from a number of causes. For example, if the patient's beta blockers have stopped working or the dose it too low, the patient might have an elevated heart rate for many hours so that the heart is never in the normal heart rate range. In fact, checking for a consistent inability to find baselines is a very useful procedure in that any cause of the patient's heart not having any "normal" segments over the baseline alert time period will trigger the alarm subroutine. Such causes can either be related to the patient's heart or they may be caused misconfigured heart rate bins or by a fault in the software or electrical circuitry of the implant. Inability to collect baselines will typically trigger a "See Doctor" alert using alert routine 639 of the alarm subroutine 490.

However, the alarm may be suppressed, depending on the value of ALRMDLY. (See blocks 900 and 902 in FIG. 7 and corresponding discussion.) In block 1229, if ALRMDLY is not 0, the routine exits. Typically, ALRMDLY is non-zero prior to implantation. This check prevents continuous "can't find baseline" alerts while the device is on the shelf.

If ALRMDLY is 0, control passes to block 1230, which compares stale cntr to $\text{STALE}_{TH}$. If stale cntr is not equal to $\text{STALE}_{TH}$, then the routine exists. Otherwise, control passes to block 1232, which involves compressing the segment and storing it in the appropriate bad baseline memory slot, and setting a flag indicating a "can't find baseline" condition has been detected.

Figure 13A:
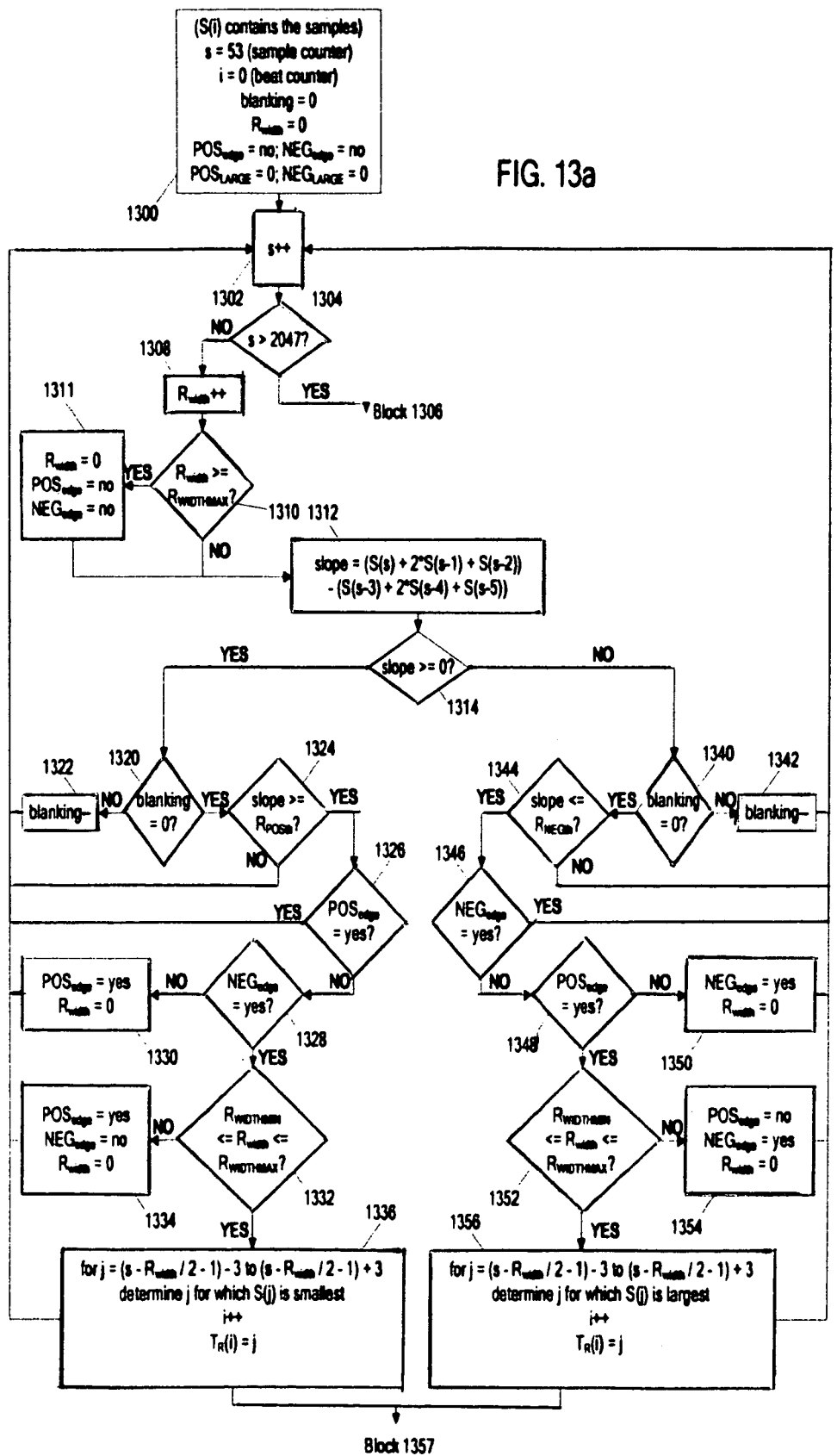

FIG. 13*a* and FIG. 13*a* collectively are a flow chart of the R peak detection routine. Peaks are located by looking for one more large magnitude slopes (positive or negative) followed by some, but not too many, samples with a small magnitude slope, which in turn are followed by a large magnitude slope of the opposite direction. If all of these conditions have been met, a peak has been found somewhere within the set of samples that satisfied the above conditions. Once a peak has been found, the routine does not look for another peak until after the end of the beat's ST segment (if known) or for a blanking interval defined by a certain number of samples (BLANKING), whichever is greater.

Throughout the discussion of this flowchart, S represents an array that contains samples corresponding to the current data segment. The counter s, which represents the current sample, indexes into the array S, so that $S(s)$ is the $s^{th}$ sample. As before, "i" is the beat counter. In block 1300, s is set to 53. The first 48 samples are discarded to avoid start-up transient, to make room in memory for header information, and to get a 10.00 second segment. After these 48 samples, the routine starts on the $6^{th}$ sample, because of the slope calculation, explained below. Also in block 1300, the beat counter "i" is set to 0, as well as the following variables: "blanking", "$R_{width}$", "$\text{POS}_{LARGE}$" and "$\text{NEG}_{LARGE}$". Variables "$\text{POS}_{EDGE}$" and "$\text{NEG}_{EDGE}$" are set to "no". The role of these variables will be described below. Finally, the memory that stores the 8 most positive and negative slopes for the segment is cleared.

In block 1302, the s counter is incremented. In block 1304, the routine checks whether the last sample in the segment, sample 2048, has been reached. If so, final segment processing is performed in block 1306, which will be described below. Otherwise, control passes to block 1308, which increments the $R_{width}$ counter, which tracks the width of the current R wave (i.e. the R wave of the i'th beat.). In block 1310, the R width is compared to a programmable threshold, $R_{WIDTHMAX}$ (preferably set to 10). If $R_{width}>=R_{WIDTHMAX}$, then the current candidate for an R wave (tracked by $R_{width}$) is considered not to be an R wave. This check helps to prevent T waves, which may otherwise appear to be R waves due to sharp upstrokes and downstrokes but are generally wider than R waves, from being considered as R waves. If $R_{width}>=R_{WIDTHMAX}$, control passes to block 1311, which resets $R_{width}$ to 0 and sets "$\text{POS}_{EDGE}$" and "$\text{NEG}_{EDGE}$" each to "no", Control is transferred to block 1312, which also is reached directly from block 1310.

Block 1312 calculates the slope of the electrogram in the neighborhood of the current sample s. In particular, the slope at s is set equal to: (S(s)+2*S(s−1)+S(s−2))−(S(s−3)+2*S(s−4)+S(s−5)). Control passes to block 1314, which checks whether the slope is positive or 0. Positive and negative slope sub-segments are processed in asymmetrical manner by routines starting at blocks 1316 and 1318, respectively. The only difference between these procedures pertains to the polarity of tests (e.g. the positive slope procedure will check if the slope is greater than a threshold while the negative slope procedure will check if the slope is less than a threshold.)

Turning to the positive slope procedure, block 1320 checks whether the variable "blanking" is equal to 0. The value of this variable is the number of samples remaining in the blanking interval. If the blanking interval is not over, the current sample is skipped. The blanking interval is decremented in block 1322 and control returns to block 1302.

If the blanking interval is over, i.e. "blanking"=0, then control passes to block 1324, which checks whether the slope is sufficiently large to be considered an R wave upstroke by comparing the slope with a threshold $R_{POSth}$, which is dynamically adjusted in a manner to be described below. If the slope is less than $R_{POSth}$, control returns to block 1302. Otherwise, control passes to block 1326, which checks whether an upstroke has already been identified for the current beat by checking whether the $POS_{edge}$ variable is set to "yes." If so, control returns to block 1302.

Otherwise, control passes to block 1328, which checks whether a downstroke has already been identified for the current beat by checking whether the $NEG_{edge}$ variable is set to "yes." If not, then a peak has not yet been located. Control passes to block 1330, where the $POS_{edge}$ variable is set to "yes" to indicate that an upstroke has been found, and the $R_{width}$ is reset to 0 to begin tracking the width of what is possibly an R wave. Control again returns to block 1302.

Returning to block 1328, if the $NEG_{edge}$ variable is set to "yes", then the newly located upstroke possibly represents the upstroke of an R wave that consists of a "v" like downstroke followed by an upstroke. However, if the width between the upstroke and downstroke is too large, the data may represent a T wave rather than an R wave. Conversely, if the if the width between the upstroke and downstroke is too small, the data may represent a fluctuation (e.g. noise) that is not an R wave. To test for both of these possibilities, in block 1332, the procedure checks whether $R_{width}$ is greater than or equal to $R_{WIDTHMIN}$, and also less than or equal to $R_{WIDTHMAX}$, where $R_{WIDTHMIN}$ and $R_{WIDTHMAX}$ are programmable thresholds preferably set to 3 and 10, respectively. If $R_{width}$ does not fall within these thresholds, control passes to block 1334, where the $POS_{edge}$ variable is set to "yes" to indicate that an upstroke has been found, the $R_{width}$ is reset to 0 to begin tracking the width of what is possibly an R wave, and the $NEG_{edge}$ variable is set to "no". Control again returns to block 1302.

Returning to block 1332, if $R_{width}$ falls within the range defined by $R_{WIDTHMIN}$ and $R_{WIDTHMAX}$. then an R wave is detected and control transfers to block 1336. To find the peak, the sample with the minimum value (the bottom of the "v" shape) is located by searching through 6 samples centered around the sample that was $R_{width}/2$ samples before the current sample. More formally, for $j=(s-R_{width}/2-1)-3$ to $(s-R_{width}/2-1)+3$, the minimum S(j) is found. The R wave time TR(i) for beat i is set to the j that resulted in the minimum S(j). Next, the beat counter i is incremented to indicate that the $i^{th}$ R wave has been located. The RR(i) interval, defined as the number of samples between the current R wave peak and the previous R wave peak, is used to determine the appropriate heart rate bin (A0-A4) for the beat. The blanking interval is set such that it ends at the estimate of the end of the ST segment, unless the amount of time to the end of the ST segment is less than BLANKING, in which case BLANKING is used as the blanking interval. The end of the ST segment is estimated by the heart rate dependent quantity $(T_{STstart}(Ax)+D_{ST}(Ax))$. If the beat is characterized as a high heart rate beat, or the beat is the first one in the segment, BLANKING is used as the blanking interval, (because the time of end of the ST segment is undefined for high heart rate beats and because the previous beat is not known for the first beat found in a segment, respectively). $POS_{edge}$ and $NEG_{edge}$ are both reset to "no" to indicate that the routine is searching for the next R wave. Control passes to block 1357.

Returning to block 1314, if the slope is negative, control passes to block 1318. The subsequent processing is symmetrical to the processing for positive slopes, except with appropriate polarity changes. Blocks 1340 and 1342 are identical to blocks 1320 and 1322. Block 1344 checks whether the slope is less than or equal to a threshold ($R_{NEGth}$), which is also dynamically adjusted in a manner to be described below. Blocks 1346 and 1348 check whether $NEG_{edge}$ and $POS_{edge}$, respectively, are "yes". In block 1350, the $NEG_{edge}$ variable is set to "yes" to indicate that a downstroke has been found and the $R_{width}$ is reset to 0 to begin tracking the width of what is possibly an R wave. In block 1354, and the $NEG_{edge}$ variable is set to "yes" and the $POS_{edge}$ variable is set to "no" to indicate that a downstroke has been found. Block 1352 is identical to block 1332. Block 1356 is identical to block 1336 except that peak of the carat shaped (^) R wave, i.e. the j for which S(j) is largest, is found rather than the bottom of the v.

From either block 1336 or block 1356, control passes to block 1357, which is shown in FIG. 13*b*. Block 1357 first computes the blanking interval that is counted by the "blanking" variable. The blanking interval is computed as a function of heart rate (RR interval) because the timing of the peak of the T wave is a function of heart rate: at higher heart rates, the T wave peaks occur relatively earlier. To account for this, the blanking interval is preferably shorter at higher heart rates.

To adapt the blanking interval to a fluctuating heart rate, variables oldBlank and newBlank are used. The variable newBlank is the newly calculated blanking interval, which is an exponential average of the previous blanking interval (oldBlank) and the current RR interval. Specifically, newBlank= (7*oldBlank+FACTOR*RR[i]/256)/8, where RR[i] is the current RR interval and FACTOR is a programmable parameter. A good value for FACTOR is 102, corresponding to ~40% (102/256) of the RR interval. The changes in newBlank are limited to +/−5 samples of the value of oldBlank.

Since there is no RR interval information for the first beat in the segment, newBlank is simply set to oldBlank.

The blanking counter "blanking" is reduced by the difference between the current sample (s) and the peak of the R wave ($T_R(i)$) (because the blanking interval starts at the peak of the R wave and the current sample s is past the peak of the R wave.)

Finally, block 1357 resets the $POS_{edge}$ and $NEG_{edge}$ variables to "no".

Returning to block 1304, if the end of the segment has been reached, control passes to block 1306, shown in FIG. 13*b*, which calculates the positive and negative slope thresholds ($R_{POSth}$ and $R_{NEGth}$) to be used for the next segment. In block 1306, the average RR interval for the segment ($P_{avg}$), is calculated as $P_{avg}=(1/m)\Sigma RR(i)$), where RR(i) is the RR interval for a beat, m=n−1 and n is the number of beats in the segment which is calculated in block 1003 (see FIG. 9). A beat counter i is set to 2, a loop limit $i_{max}$ is set to m to indicate a loop starting with block 1309 will process m beats, and a short beat counter $m_{short}$ is set to 0.

Control passes to block 1309, which is the start of a loop, as mentioned. If an RR(i) interval for a particular beat is much shorter than average, then some sort of arrhythmia may be occurring, e.g. that beat may be an ectopic beat. Whether an RR(i) interval is considered to be abnormally short relative to other beats in the segment depends on the programmable parameter $P_{SHORT}$. Specifically, a beat is determined to be too short relative to other beats if its R-R interval is less than $(P_{SHORT}/256)*P_{avg}$. 205 is an exemplary value for PSHORT, (which is results in 80% (205/256) of $P_{avg}$ as the criteria).

If the RR(i) interval is too short, control passes to block 1311, which increments the short beat counter $m_{short}$. Control passes to block 1312, which increments the loop counter i. Control then passes to block 1323, which checks whether the loop is complete.

Returning to block 1309, if the RR(i) interval is not too short, then control passes to block 1313, which updates QRS height histograms. (Such histograms are further described in U.S. patent application Ser. No. 10/950,401, filed Sep. 28, 2004, entitled "Implantable System for Monitoring the Condition of the Heart", assigned to the assignee hereof.) Processing continues in block 1315, which checks whether the RR(i) interval is indicative of a high heart rate by comparing the RR(i) interval with a threshold ($HI_{TH}$). If the RR(i) interval is shorter than $HI_{TH}$, then the beat is not used to determine R wave slopes and control passes to block 1312. Otherwise, control passes from block 1315 to block 1321, in which the most positive and negative R wave slopes within 16 samples on either side of the R wave peak are saved if they are within the top eight most positive and negative R wave slopes, respectively, for the segment. Note that beats whose associated RR intervals were considered too short according to the block 1309 criteria are excluded from the slope storage in block 1321; these beats. These short RR beats may be ectopic beats, in which case their slopes may be artificially too large. Therefore, it is desirable to exclude them from the slope threshold update procedure. From block 1321, control transfers to block 1312 . . . .

When all beats in the segment have been processed, block 1323 transfers control to block 1325, which calculates the positive and negative slope thresholds ($R_{POSth}$ and $R_{NEGth}$) to be used for the next segment. These thresholds are determined by computing a weighted (exponential) average of the current threshold and the average ($POS_{LARGE}, NEG_{LARGE}$) of the largest slopes in the current segment. For example, for the case of $R_{POSth}$, the weighted average is $7*$current $R_{POSth}/8 + x/8$, where x is equal to a programmable fraction ($P_{THRESH}/256$) of $POS_{LARGE}$. The calculated values are checked and adjusted if necessary to make sure they don't change too quickly or get too close to 0. Specifically, for the case of $R_{POSth}$, the computed $R_{POSth}$ is compared to the old $R_{POSth}$ plus MaxAwayFrom0, a programmable parameter that serves as an upper bound to how much $R_{POSth}$ is allowed to increase from segment to segment. If $R_{POSth}$ is larger than the old $R_{POSth}$ plus MaxAwayFrom0, then $R_{POSth}$ is set equal to the old $R_{POSth}$ plus MaxAwayFrom0. Similarly, if the computed $R_{POSth}$ indicates a rapid decrease, $R_{POSth}$ is set equal to the old $R_{POSth}$ minus MaxToward0, a programmable parameter that serves as an upper bound to how much $R_{POSth}$ is allowed to decrease from segment to segment. And finally, $R_{POSth}$ is not allowed to shrink below 32. The procedure for $R_{NEGth}$ is analogous. The preferred value for MaxAwayFrom0 is 10 and the preferred value for MaxToward0 is 255 (effectively disabling this limit).

Block 1323 ensures that there are, at most, eight largest slopes that are used to calculate the average ($POS_{LARGE}$, $NEG_{LARGE}$) of the largest slopes in the current segment. If more than two positive or negative slopes, respectively, were saved in block 1323, than $POS_{LARGE}$ or $NEG_{LARGE}$ are equal to the average of these positive and negative slopes, respectively. If only two or less-positive slopes were saved in block 1323, then the segment is considered not useful for updating $R_{POSth}$. In this case, $POS_{LARGE}$ is set equal to $R_{POSth}/2$, thereby effectively decreasing $R_{POSth}$. Thus, if the small number of detected R peaks was due to an improperly large value of $R_{POSth}$, the decrease in $R_{POSth}$ may remedy the inability to successfully detect R peaks. A typical value of $P_{THRESH}$ is 115 (115/256=45%). An analogous procedure is applied for negative slopes ($NEG_{LARGE}$).

An alternate to ST shift detection is to process just the T wave, which can change its peak or average amplitude rapidly if there is a heart attack. The T wave can, however change its amplitude slowly under normal conditions so a T wave shift detector would need a much shorter time U than that of a detector using the ST segment before the T wave. If the detector is checking for such T wave shift, i.e. a voltage shift of the T wave part of the ST segment, then it may be desirable to check against a baseline where U is 1 to 30 minutes and W is 15 seconds to 15 minutes. For example, U=3 minutes and W=15 seconds is a preferred setting to catch a quickly changing T wave. This would also allow use of recent electrogram segments stored in the recent electrogram memory of FIG. 4 as baseline electrogram segments for T wave shift detection. It is envisioned that the programmer 68 of FIG. 1 would allow the patient's doctor to program the cardiosaver 5 to use ST segment shift or T wave shift detectors by themselves, or together simultaneously. If both were used then the programmer 68 would allow the patient's doctor to choose whether a positive detection will result if either technique detects an event or only if both detect an event.

The parameters Y, $P_{COLLECT}$, $P_{COLLECT2}$, U and W are stored with the programmable parameters 471 in the RAM 47 in FIG. 4. These parameters may be permanently set at the time of manufacturing of the cardiosaver 5 or they may be programmed through the programmer 68 of FIG. 1. The calculated criteria for cardiac event detection extracted from the baseline electrogram segments stored in baseline electrogram memory 474 are stored in the calculated baseline data memory 475 of the RAM 47.

Although it may be effective to fix the values of time offsets $T_{PQ}$ (502) and $T_{ST}$ (504) and the durations $D_{PQ}$ (506) and $D_{ST}$ (508), it is envisioned that the time offsets $T_{PQ}$ and $T_{ST}$ and the durations $D_{PQ}$ and $D_{ST}$ could be automatically adjusted by the cardiosaver 5 to account for changes in the patient's heart rate. If the heart rate increases or decreases, as compared with the patient's normal heart rate, it envisioned that the offsets $T_{PQ}$ (502) and $T_{ST}$ (504) and/or the durations $D_{PQ}$ (506) and $D_{ST}$ (508) could vary depending upon the R-R interval between beats or the average R-R interval for an electrogram segment. A simple technique for doing this would vary the offsets $T_{PQ}$ and $T_{ST}$ and the durations $D_{PQ}$ and $D_{ST}$ in proportion to the change in R-R interval. For example if the patient's normal heart rate is 60 beats per minute, the R-R interval is 1 second; at 80 beats per minute the R-R interval is 0.75 seconds, a 25% decrease. This could automatically produce a 25% decrease in the values of $T_{PQ}$, $T_{ST}$, $D_{PQ}$ and $D_{ST}$. Alternately, the values for $T_{PQ}$, $T_{ST}$, $D_{PQ}$ and $D_{ST}$ could be fixed for each of up to 20 preset heart rate ranges. In either case, it is envisioned that after the device has been implanted, the patient's physician would, through the programmer 68 of FIG. 1, download from the cardiosaver 5 to the programmer

68, a recent electrogram segment from the recent electrogram memory 472. The physician would then use the programmer 68 to select the values of $T_{PQ}$, $T_{ST}$, $D_{PQ}$ and $D_{ST}$ for the heart rate in the downloaded recent electrogram segment. The programmer 68 would then allow the physician to choose to either manually specify the values of $T_{PQ}$, $T_{ST}$, $D_{PQ}$ and $D_{ST}$ for each heart rate range or have the cardiosaver 5 automatically adjust the values of $T_{PQ}$, $T_{ST}$, $D_{PQ}$ and $D_{ST}$ based on the R-R interval for each beat of any electrogram segment collected in the future by the cardiosaver 5. It is also envisioned that only the offset times, $T_{PQ}$ and $T_{ST}$, might be automatically adjusted and the durations $D_{PQ}$ and $D_{ST}$ would be fixed so that the average values of the ST and PQ segments $V_{PQ}$ (512), $V_{ST}$(514), $V'_{PQ}$(512') and $V'_{ST}$(514') would always use the same number of data samples for averaging.

When used in pacemakers or combination pacemaker/ICDs it envisioned that the start time $T_{ST}$ and duration $D_{ST}$ of the ST segment may have different values than during sinus rhythm (when the pacemaker is not pacing) as pacing the heart changes the characteristics of ischemic ST shifts causing them to occur later relative to the start of the R wave. It is also envisioned, that the offset for the start of the ST segment may be better measured from the S Wave instead of the R wave used for sinus rhythm when the pacemaker is not pacing. The technique of using different timing parameters for start and duration when pacing can be applied to analysis of any sub-segment of the electrogram including the sub-segment that includes the T wave peak.

It is also envisioned that the patient would undergo a stress test following implant. The electrogram data collected by the implant 5 would be transmitted to the programmer 68 of FIG. 1, and one or more of the parameters $T_{PQ}$ (502), $T_{ST}$ (504), $D_{PQ}$ (506) and $D_{ST}$ (508) of FIG. 6 would be automatically selected by the Programmer based on the electrogram data from the stress test. The data from the stress test should cover multiple heart rate ranges and would also be used by the programmer 68 to generate the excessive ST shift detection percentage thresholds $P_{ST}$ for each of the heart rate ranges. In each case where the programmer 68 automatically selects parameters for the ST shift detection algorithm, a manual override would also be available to the medical practitioner. Such an override is of particular importance as it allows adjustment of the algorithm parameters to compensate for missed events or false positive detections.

The S wave peak voltage $V_S$ (507) is also shown on the baseline beat 500 in FIG. 6. While the preferred embodiment of the present invention uses an average $\Delta R(avg)$ of the average PQ to R wave amplitudes $\Delta R(i)$ as the normalization voltage for setting the threshold for ST shift detection, it is also envisioned that normalization voltage could be the average of the entire R wave to S wave amplitude $(V_R - V_S)$ or it could be the larger of $\Delta R(i)$ or the PQ to S amplitude $\Delta S(i) = V_S - V_{PQ}$. It is important to note here that the threshold for ST shift detection is set as a percentage of the average of baseline average signal amplitudes. This is important because the baseline signal is only collected if the electrogram is normal and therefore the thresholds would not be affected by transient changes in signal amplitude (e.g. R wave height) that can occur during an ST elevation myocardial infarction. Therefore, for the purposes of the present invention the threshold is calculated as a percentage of an average of the signal amplitude of U baselines. In turn, the signal amplitude of each of the U baselines is the average signal amplitude of at least two beats of the baseline electrogram segment where the average signal amplitude of a baseline segment can be any of the following the average PQ segment to R voltage difference $\Delta R(i)$, the peak-to-peak voltage of the beat (i.e. the R to S wave voltage difference) $(V_R - V_S)$, the average PQ segment to S wave voltage difference $\Delta S(i)$, the larger of $\Delta R(i)$ or $\Delta S(i)$, or any average signal amplitude calculated from at least two beats of the baseline electrogram segment.

One embodiment of ST shift and T wave shift detection might use a baseline for ST shift detection that is an average of the baselines over the 24±½ hour period before and a baseline for T wave shift that is 1 to 4 minutes in the past. This would require that the baseline extraction subroutine 835 be run for T wave shift parameters approximately every 60 seconds and for ST segment parameters every hour.

Figure 14:
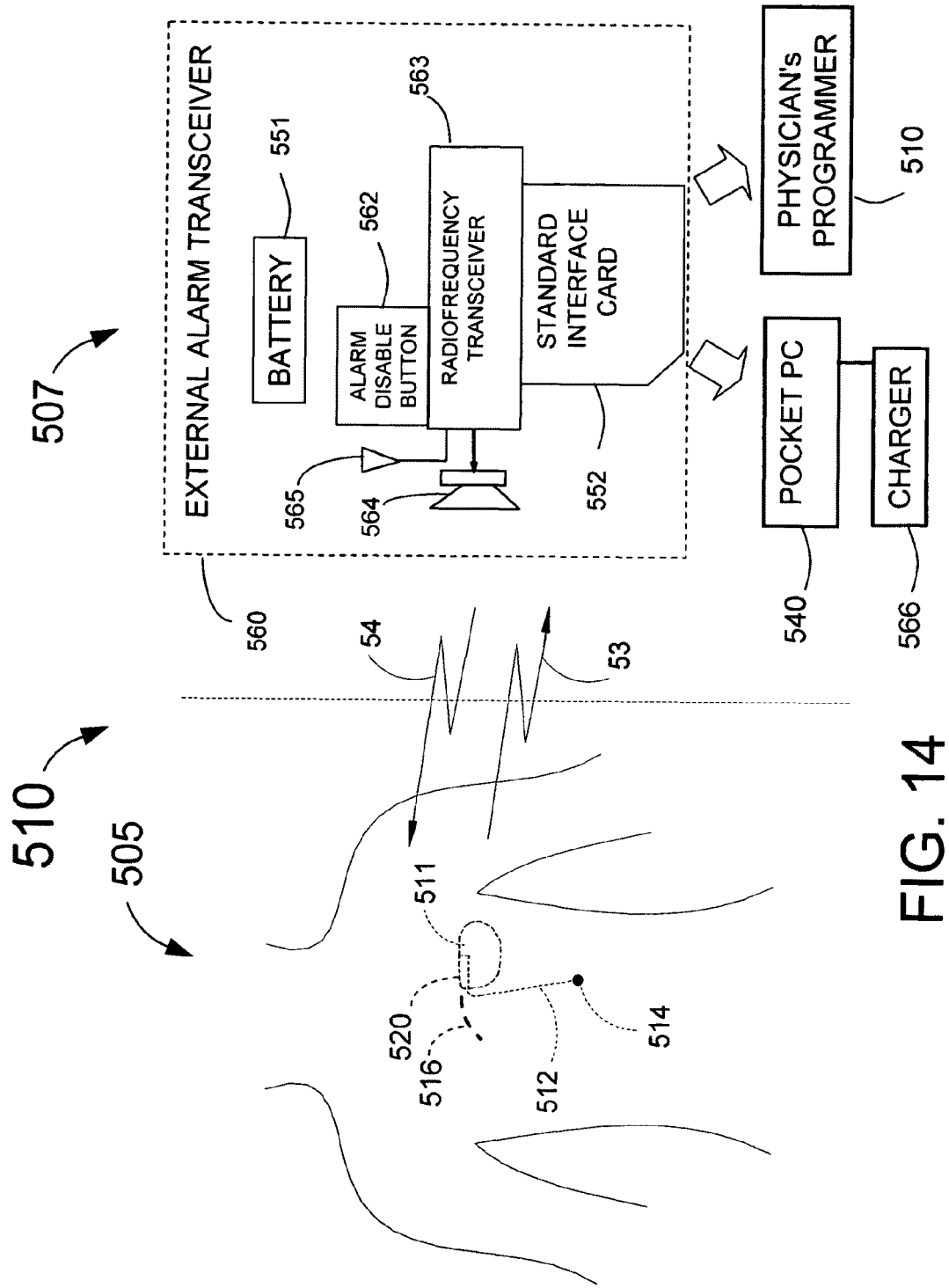
FIG. 14 is an alternate embodiment of the system.

FIG. 14 shows a modified embodiment of the system 510. The cardiosaver implant 505 with lead 512, electrode 514, antenna 516, header 520 and metal case 511 would be implanted subcutaneously in a patient at risk of having a serious cardiac event such as an acute myocardial infarction. The lead 512 could be placed either subcutaneously or into the patient's heart. The case 511 would act as the indifferent electrode. The system 510 also included external equipment that includes a physician's programmer 510 an external alarm transceiver 560 and a pocket PC 540 with charger 566. The external alarm transceiver 560 has its own battery 561 and includes an alarm disable button 562 radiofrequency transceiver 563, speaker 564, antenna 565 and standard interface card 552. The cardiosaver 505 has the same capabilities as the cardiosaver 5 of FIGS. 1 through 4.

The standardized interface card 552 of the external alarm transceiver 510 can be inserted into a standardized interface card slot in a handheld or laptop computer. The pocket PC 540 is such a handheld computer. The physician's programmer 510 is typically a laptop computer. Such standardized card slots include compact flash card slots, PCMCIA adapter (PC adapter) card slots, memory stick card slots, Secure Digital (SD) card slots and Multi-Media card slots. The external alarm transceiver 510 is designed to operate by itself as a self-contained external alarm system, however when inserted into the standardized card slot in the pocket PC 540, the combination forms an external alarm system with enhanced functionality. For example, in stand alone mode without the pocket PC 540, the external alarm transceiver 560 can receive alarm notifications from the cardiosaver implant 505 and can produce an external alarm signal by generating one or more sounds through the speaker 564. These sounds can wake the patient up or provide additional alerting to that provided by the internal alarm signal generated by the cardiosaver 505. The alarm disable button 562 can acknowledge and turn off both external and internal alarm signals. The standalone external alarm transceiver 560 therefore provides key functionality could be small enough to wear on a chain around the neck or on a belt.

When plugged into the pocket PC 540, the external alarm transceiver 560 can facilitate the display of text messages to the patient and electrogram data that is transmitted from the cardiosaver 505. The pocket PC 540 also enables the patient operated initiator 55 and panic button 52 capabilities of the external alarm system 60 of FIG. 1. Being a pocket PC also readily allows connection to wireless communication capabilities such as wireless internet access that will facilitate retransmission of data to a medical practitioner at a geographically remote location. It is also envisioned that the charger 566 could recharge the batter 551 when the external alarm adaptor 560 is plugged into the pocket PC 540.

The external alarm transceiver 560 can also serve as the wireless two-way communications interface between the cardiosaver 505 and the programmer 510. The physician's programmer 510 is typically a laptop computer running some version of the Microsoft Windows operating system. As such, any or the above standardized slot interfaces can be either directly interfaced to such a laptop computer or interfaced using a readily available conversion adaptor. For example, almost all laptop computers have a PCMCIA slot and PCMCIA card adaptors are available for compact flash cards, Secure Digital cards etc. Thus the external alarm adaptor 560 could provide the interface to the physician's programmer 510. This provides additional security as each cardiosaver implant 505 and external alarm adaptor 560 could be uniquely paired with built in security codes so that to program the implant 505, the physician would need the patient's external alarm adaptor 560 that would act both as a wireless transceiver and as a security key.

Although the system 10 as described herein could clearly operate as a stand-alone system, it is clearly conceivable to utilize the system 10 with additional pacemaker or implanted defibrillator circuitry. As shown in FIG. 4, pacemaker circuitry 170 and/or defibrillator circuitry 180 could be made part of any cardiosaver 5 or 505. Furthermore, two separate devices (one pacemaker or one defibrillator plus one cardiosaver 5) could be implanted within the same patient.

Figure 15:
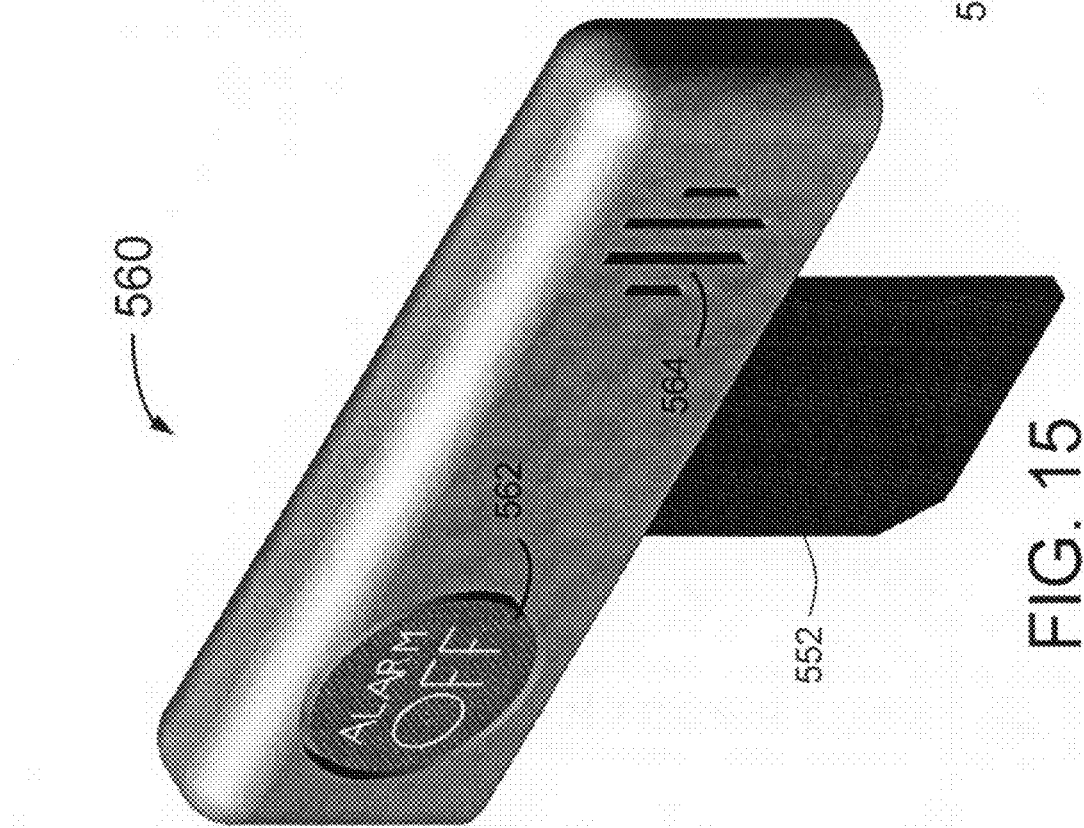
FIG. 15 illustrates the preferred physical embodiment of the external alarm transceiver.

FIG. 15 illustrates a preferred physical embodiment of the external alarm transceiver 560 having standardized interface card 552, alarm disable button 562 labeled "ALARM OFF" and speaker 564. It is also envisioned that by depressing and holding the alarm disable button 562 for a minimum length of time, when there is not an alarm, the external alarm transceiver could verify the operational status of the cardiosaver 505 and emit a confirming sound from the speaker 564.

Figure 16:
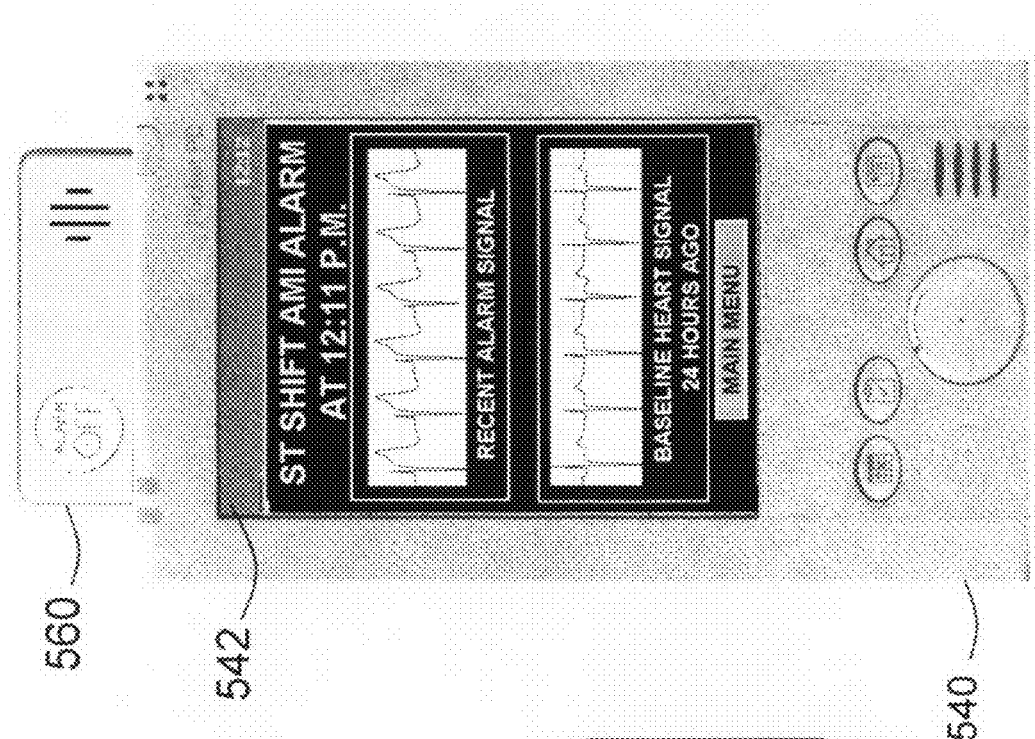
FIG. 16 illustrates the physical embodiment of the combined external alarm transceiver and pocket PC.

FIG. 16 illustrates the physical embodiment of the combined external alarm transceiver 560 and pocket PC 540 where the standardized interface card 552 has been inserted into a matching standardized interface card slot the pocket PC 540. The screen 542 of the pocket PC 540 shows an example of the display produced by an external alarm system following the detection of an acute myocardial infarction by the cardiosaver 505. The screen 542 of FIG. 15 displays the time of the alarm, the recent electrogram segment from which the cardiac event was detected and the baseline electrogram segment used for comparison in the cardiac event detection. Such a display would greatly facilitate diagnosis of the patient's condition upon arrival at an emergency room and could eliminate the need for additional electrocardiogram measurements before the patient is treated.

Figure 17:
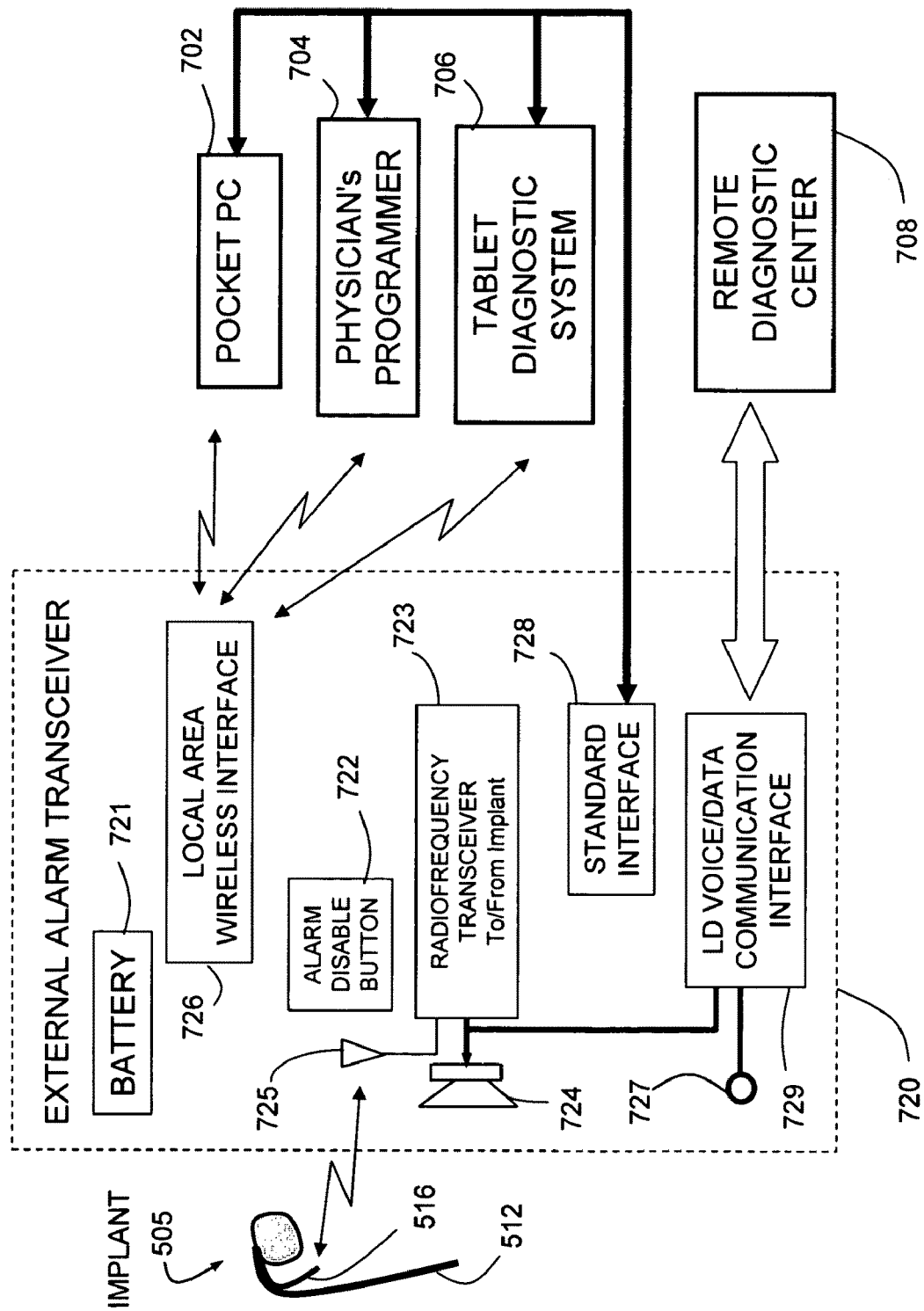
FIG. 17 shows an advanced embodiment of the external alarm transceiver.

FIG. 17 shows an advanced embodiment of the external alarm transceiver 720 having a battery 721, an alarm disable button 722, a RF transceiver for data communication to and from the implanted device, a loudspeaker 724, a microphone 727, a local area wireless interface 723, a standard interface 728 and a long distance (LD) voice/data communication interface 729. The function of the alarm disable button 722 and the radiofrequency transceiver 723 are as described for the similar devices shown in FIG. 13*a* FIG. 13*a*. The local area wireless interface 723 provides wireless communication within a building (e.g. home, doctor's office or hospital) to and from the implant 505 with lead 512 and antenna 516 through the external alarm transceiver 720 from and to assorted external equipment such as Pocket PCs 702, Palm OS PDAs, Notebook PCs, physician's programmers 704 and tablet diagnostic systems 706. The means for transmission from the local area wireless interface 723 may be by radiofrequency or infra-red transmission. A preferred embodiment of the local area wireless interface 723 would use a standardized protocol such as IRDA with infra-red transmission and Bluetooth or WiFi (802.11.a, b, or g) with radiofrequency transmission. The local area wireless interface 723 would allow display of implant data and the sending of commands to the implant 505.

The standard interface 728 provides a physical (wired) connection for data communication with devices nearby to the patient for the purposes of displaying data captured by the implant 505 and for sending commands and programs to the implant 505. The standard interface 728 could be any standard computer interface; for example: USB, RS-232 or parallel data interfaces. The pocket PC 702 and physician's programmer 704 would have functionality similar to the pocket PC 540 and physician's programmer 510 of FIG. 13*a* FIG. 13*a*.

The tablet diagnostic system 706 would provide a level of functionality between that of the pocket PC 702 and physician's programmer 706. For example, the tablet diagnostic system would have the programmer's ability to download complete data sets from the implant 505 while the pocket PC is limited to alarm and baseline electrogram segments or the most recent electrogram segment. The tablet diagnostic system 706 would be ideal for an emergency room to allow emergency room medical professionals to quickly view the electrogram data stored within the implant 505 to assess the patient's condition. The recently introduced Tablet PCs such as the Toshiba Portege 3500 or the Compaq TC1000 have IRDA, WiFi and USB interfaces built into them and so would make an ideal platform for the tablet diagnostic system 706. It is envisioned that such a tablet diagnostic system in an emergency room or medical clinic would preferably be connected to its own external alarm transceiver. The tablet diagnostic system 706 could be hand held or mounted on a wall or patient bed. A unit located near the bed of an incoming patient having an implant 505 would enable display of patient diagnostic data without requiring any attachments to the patient. Such wireless diagnosis is similar to that envisioned for the tricorder and diagnostic beds of the Star Trek science fiction series created by Gene Roddenberry.

The long distance voice/data communication interface 729 with microphone 727 and also attached to the loudspeaker 724 will provide the patient with emergency contact with a remote diagnostic center 708. Such a system could work much like the ONSTAR emergency assistance system now built into may cars. For example, when a major or EMERGENCY alarm is identified by the implant 505, the following steps could be followed:

1. The device will first ascertain if an external alarm transceiver is within range, if not the internal alarm will be initiated.
2. If the external alarm transceiver is within range the system will next see if there is access to the remote diagnostic center 708 through the long distance voice/data communication interface 729. If not the external alarm transceiver 720 and implant 505 will initiate internal and/or external alarm notification of the patient.
3. If there is access to the remote diagnostic center 708 the long distance voice/data communication interface 729, the patient alarm information including alarm and baseline electrogram segments will be transmitted to the remote diagnostic center 708. A medical professional at the remote diagnostic center 708 will view the data and immediately establish voice communication to the external alarm transceiver 720 through the long distance voice/data communication interface 729. If this occurs, the first thing that the patient will hear is a ringing tone and/or a voice announcement followed by the contact with the medical professional who can address the patient by name and facilitate appropriate emergency care for the patient. In this case, the internal and external alarms will not be needed and to the patient it will resemble an incoming telephone call from the medical professional. It is also envisioned that the voice of the medical professional could be the first thing that the patient hears although an initial alerting signal is preferred.

This method of establishing the highest level of communication available to the system with the fall back of just the internal alarm will provide the best possible patient alerting based on what is available at the time of the alarm.

The data communications between the external alarm transceiver 720 and the remote diagnostic center 708 would utilize a standardized (or custom) data communications protocol. For example, the data communications might utilize any or all of the following either within a private network, a VPN, an intranet (e.g. a single provider network such as the Sprint data network) or through the public internet:

1. Basic TCP/IP messaging within a single network or through the internet.
2. Short Messaging Service (SMS)
3. Multimedia Message Service (MMS) used for cell phone transmission
4. Universal Datagram Protocol (UDP)

It is also envisioned that the present invention would take advantage of existing telephone network call center technology including use of Automatic Number Identification (ANI) to identify the incoming call, and Dialed Number Identification Service (DNIS) where different numbers might be dialed by the external alarm transceiver 720 depending on the severity of the detected cardiac event. For example, in the case where the call is placed by the emergency alarm transceiver 720, an EMERGENCY alarm might dial a different number than a SEE DOCTOR alert which might be different from a patient-initiated "panic button" call. DNIS could help get the appropriate help for the patient even if data connectivity is unavailable and might be used to prioritize which call is answered first (e.g., an EMERGENCY alarm would have higher priority than a SEE DOCTOR alert).

It is also envisioned that the remote diagnostic center 708 could facilitate the scheduling of an appointment with the patient's doctor following a SEE DOCTOR alert.

Although throughout this specification all patients have been referred to in the masculine gender, it is of course understood that patients could be male or female. Furthermore, although the only electrogram indications for an acute myocardial infarction that are discussed herein are shifts involving the ST segment and T wave height, it should be understood that other changes in the electrogram (depending on where in the heart the occlusion has occurred and where the electrodes are placed) could also be used to determine that an acute myocardial infarction is occurring. Furthermore, sensors such as heart motion sensors, or devices to measure pressure, $pO_2$ or any other indication of an acute myocardial infarction or cardiac events could be used independently or in conjunction with a ST segment or T wave shift detectors to sense a cardiac event.

It is also envisioned that all of the processing techniques described herein for an implantable cardiosaver are applicable to a system configuration using skin surface electrodes and a non-implanted cardiosaver 5 the term electrogram would be replaced by the term electrocardiogram. Thus the cardiosaver device described in FIGS. 5 through 12 would also function as a monitoring device that is completely external to the patient.

Figure 18:
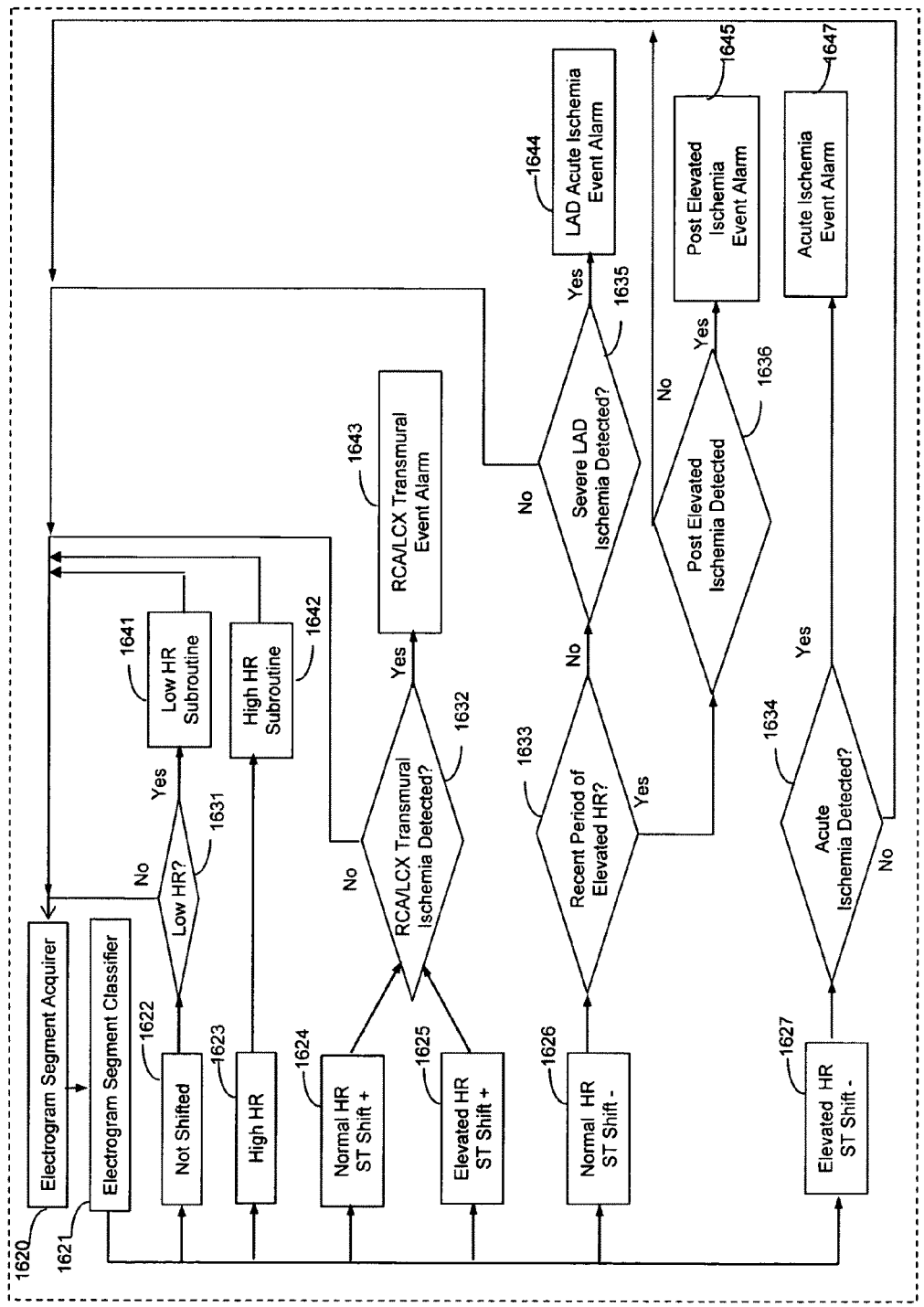
FIG. 18 is an alternate scheme for detecting ST shift related conditions that may be used in conjunction the cardiosaver event detection program shown in FIG. 5. The routine in FIG. 18 examines the polarity of ST shifts and also selectively determines whether an ST shift is associated with a recovery from high heart rates.

FIG. 18 is a flowchart of an alternate scheme for detecting ST shift related conditions that takes the polarity of ST shifts into account and that may be used in conjunction with the cardiosaver event detection program shown in FIG. 5. The meaning of the polarity of the ST shifts depends on lead orientation. If other leads are used, the teachings of the present invention may be used to implement a cardiac event detection routine analogous to that shown in FIG. 18.

In block 1620, an electrogram segment is acquired in the manner described with reference to FIG. 5. In block 1621, electrogram segments are classified in terms of heart rate (e.g. low, normal, elevated or high) and ST shift (not shifted, positive shift, negative shift) in the manner described with reference to FIG. 9 with ST shift polarity information retained. Different segment categorizations are shown in blocks 1622, 1623, 1624, 1625, 1626 and 1627. Block 1622 corresponds to a segment that is not ST shifted and not characterized by a high heart rate. Block 1623 corresponds to a segment that is not ST shifted and is characterized by a high heart rate. Blocks 1624 and 1625 correspond to positive ST shifts at normal and elevated heart rates, respectively. Blocks 1626 and 1627 correspond to negative ST shifts at normal and elevated heart rates, respectively.

If a segment is not ST shifted and not characterized by a high heart rate, block 1622 passes control to block 1631, which checks whether the heart rate is beneath a threshold. If so, a low heart rate subroutine 1641 is invoked that checks whether a specified number of consecutive previous segments were also characterized by a low heart rate. This subroutine represents block 826 and related blocks of FIG. 5. Returning to block 1631, if the segment is not characterized by a low heart rate, control returns to block 1620, which acquires the next electrogram segment.

If a segment is characterized by a high heart rate, block 1623 passes control to a high heart rate subroutine 1642. Analogous to the low heart rate subroutine 1641, the high heart rate subroutine 1642 checks whether a specified number of consecutive previous segments were also characterized by a high heart rate. (See block 842 and related blocks of FIG. 5) If so, the system generates an appropriate response such as generating an alarm.

If a segment is characterized by a positive ST shift, whether at a normal heart rate (block 1624) or at a high heart rate (block 1624), it is likely that there is a severe acute blockage of the LCX or the RCA, although some types of severe acute blockages of the LAD may cause a positive shift. The rationale for the relationship between ST shift polarity and occluded artery will be discussed below. In any event, both blocks 1624 and 1625 pass control to block 1632, which determines whether RCA/LCX transmural ischemia is present by checking whether a certain number of consecutive previous segments were also categorized by a positive ST shift. The operation of block 1232 will be further described with reference to FIG. 19. If block 1632 determines that transmural RCA/LCX ischemia is present, control passes to block 1643, which generates an appropriate alarm (that is conveyed to the patient and/or a central station). If transmural ischemia is not detected in block 1632, control again passes back to block 1620.

If a segment is characterized by a negative ST shift, the segment's heart rate is also examined to determine the causitive event. If the segment's heart rate was normal, block 1626 passes control to block 1633, which checks whether the current normal heart rate follows a recent period of elevated heart rate. This check is necessary because many individuals, in particular those with chronic ischemia, tend to develop ST depression at high heart rates that persists even after the heart has returned to a lower rate. More particularly, for a given heart rate, many people exhibit a negative ST vs. heart rate curve, whereby the ST level is lower during the recovery from high heart rates compared to the ST level associated with increases in heart rate. Healthy persons may exhibit a positive ST vs. heart rate curve. As mentioned in the Background section, the hysteresis phenomenon is well known with respect to electrocardiograms associated with surface electrodes.

The operation of block 1633 will be described in more detail below In any event, if block 1633 determines that there has not been a recent recovery from a high heart rate, control passes to block 1635, which applies a persistence criterion (i.e. multiple shifted segments) analogous to that applied by block 1632. If the persistence criterion is met, then a severe LAD ischemia has been detected and appropriate action is taken in block 1644. Otherwise, control passes back to block 1620.

If block 1633 determines that there has been a recent recovery from a high heart rate, control passes to block 1636, which applies a relatively more stringent persistence criteria, as will be further described below.

If a segment is characterized by a negative ST shift at an elevated heart rate, block 1627 passes control to block 1634, which applies a persistence criterion. If the persistence criterion is met, control passes to block 1647, which generates an appropriate response such as a high heart rate ischemia event alarm. Another possible response is to save the event in memory, without generating an alarm, for later review.

The relationship between ST segment polarity, heart rate, and the location of the ischemia will now be discussed. During the ST segment, an ischemic patch of tissue will be characterized by a negative potential (in a can-to-tip orientation). The non-ischemic remaining tissue will be characterized by a reciprocal positive potential.

However, transmural potential gradients (i.e. potential gradients across the heart wall), complicate the potential at the non-ischemic tissue. In particular, assume that the ischemia is subendocardial. Due to electrical coupling and possible ventricular pressure (as will be discussed below), the ischemic subendocardial tissue will tend to cause the non-ischemic subendocardial tissue to behave as if it is somewhat ischemic. This results in a sort of global subendocardial ischemia, which renders the entire subendocardium negative with respect to the epicardium. The global ischemia effect is enhanced at higher heart rates. (For a possible explanation, see Hopenfeld, *Biomed Eng Online.* 2007; 6:6.)

The global transmural potential gradient tends to make the non-ischemic subendocardium negative while the ischemic to non-ischemic tissue gradient tends to make the non-ischemic subendocardium positive. The balance between these two gradients determines the ST shift polarity when the RV apex is outside of the ischemic region, which is generally the case when an occlusion occurs in the RCA or LCX. Data from Angel Medical System's Guardian device suggests that the global transmural potential gradient tends to dominate, so that the can-to-RV apex lead tends to record a negative ST deviation in the case of chronic subendocardial ischemia of tissue perfused by the RCA or LCX.

When the ischemia becomes sufficiently transmural to begin affecting the epicaridum, the epicardium beings to repolarize earlier, which tends to reduce the transmural potential gradient. Thus, the ischemic to non-ischemic tissue gradient dominates, resulting in ST segment elevation (can-to-RV apex lead) for LCX or RCA occlusions.

If the RV apical electrode is in the ischemic patch, which is often the case with LAD occlusions, then the can-to-RV apex lead will tend to record ST segment depression, regardless of heart rate or the extent that the ischemia extends through the heart wall.

Other factors could also cause the non-ischemic tissue to behave ischemically. One important factor is ventricular diastolic pressure. It is known that ischemia causes an increase in ventricular diastolic pressure. Since heart cells tend to behave ischemically with increases in pressure, the diastolic pressure increase associated with ischemia could cause the entire subendocardium to behave as if it were ischemic, as has been proposed by Kubota et al. (*Am Heart J;* 110: 949-955, 1985). It is thus possible that chronic ST segment monitoring by an endocardial electrode may serve as a proxy for increased diastolic pressure; this may be useful in the monitoring of congestive heart failure patients. Body surface leads that sense current flow aligned with the long axis of the heart (e.g. limb lead II) may similarly prove useful for such monitoring; such leads are sensitive to endocardial-epicardial potential gradients.

Figure 19:
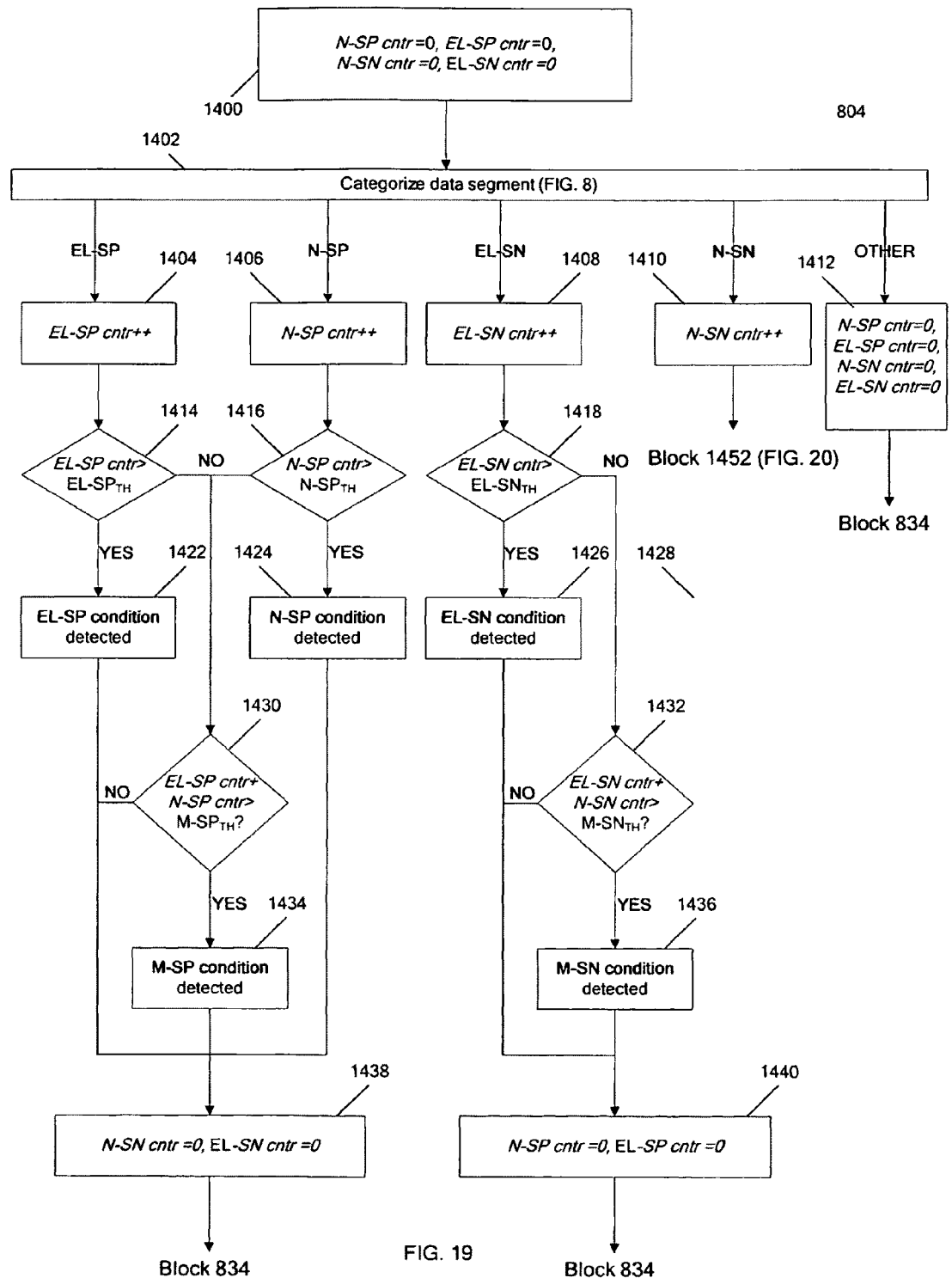
FIGS. 19 and 20 are a flow chart of implementation of the method described with reference to FIG. 18.
Figure 20:
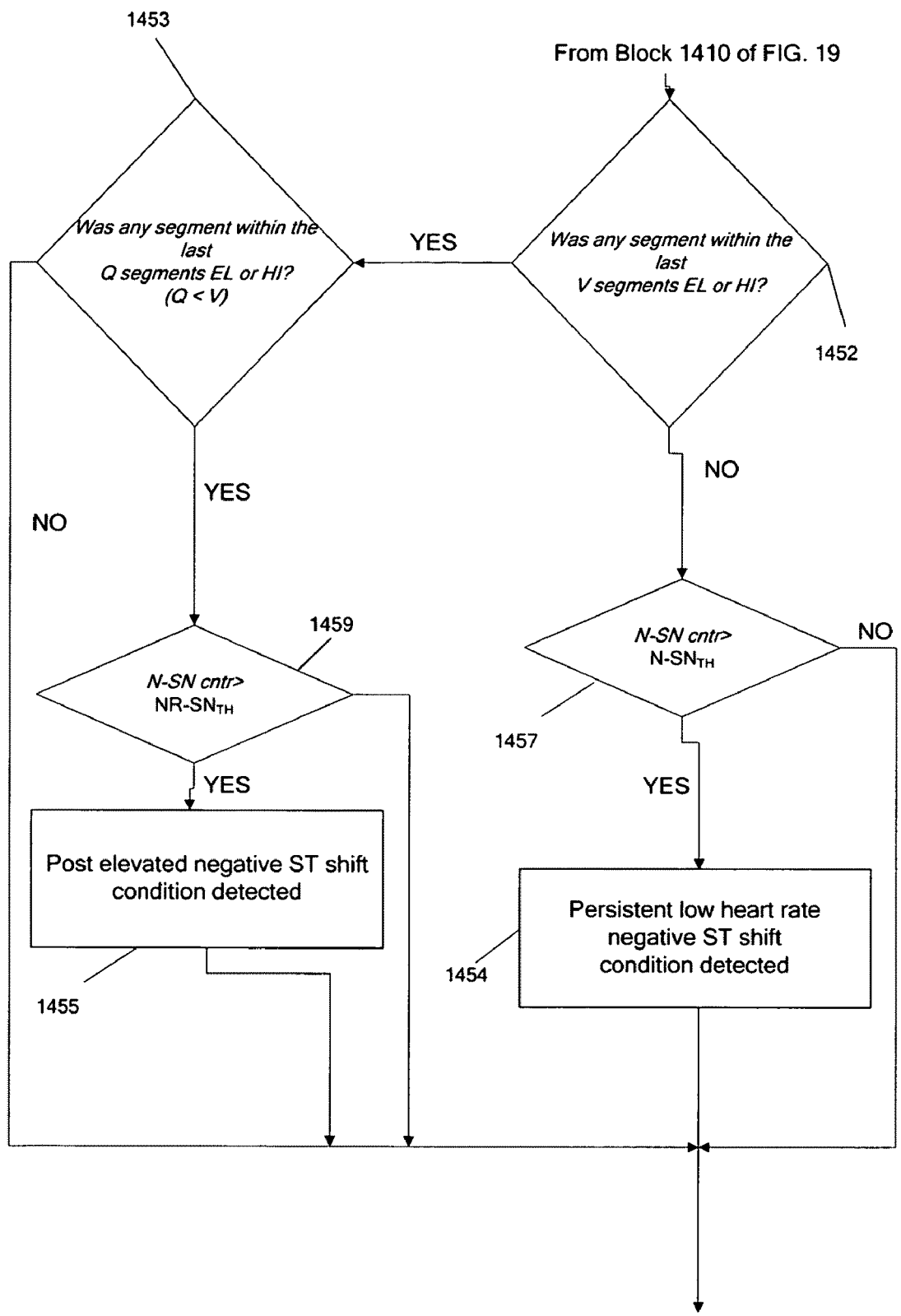

FIG. 19 is an implementation of blocks 1632, 1633, 1634, 1635 and 1636 of FIG. 18. To track both the polarity of ST shifts and heart rate, as required by the flowchart in FIG. 18, the program shown in FIG. 19 includes four counters, N-SP, EL-SP, N-SN and EL-SN. N-SP and EL-SP count the number of segments with positive ST shifts at normal and elevated heart rates, respectively. N-SN and EL-SN count the number of segments with negative ST shifts at normal and elevated heart rates, respectively. All of these counters are initialized to 0 in block 1400, which may be added to the initialization block 800 in FIG. 5.

After a segment is acquired (see block 802 of FIG. 5 and block 1620 of FIG. 18), it is categorized in block 1402 (analogous to block 804 of FIG. 5 and block 1621 of FIG. 18). If the segment is characterized by a positive shift, control is transferred to block 1404 or block 1406 according to whether the segment is N-SP or EL-SP. If the segment is characterized by a negative shift (N-SN or EL-SN), control is transferred to block 1408 or block 1410 according to whether the segment is N-SN or EL-SN. If the segment is not ST shifted, control is transferred to block 1412.

In blocks 1404 and 1406 the EL-SP cntr and the N-SP cntr are incremented respectively. In blocks 1414 and 1416, respectively, the EL-SP cntr and the N-SP cntr are checked against programmable thresholds EL-SP$_{TH}$ and N-SP$_{TH}$ respectively. N-SP$_{TH}$ is preferably set to 3, which means that positive shifts at normal heart rates will trigger an N-SP detectable condition within 90 segments at the normal 30 second acquisition interval. A longer amount of time, preferably five minutes (EL-SP$_{TH}$, =300 s/30 s=10), may be required to trigger a detectable condition at higher rates. Blocks 1422 and 1424 respectively set flags indicating the detection of a positive shift for elevated and normal heart rates, respectively.

It is possible for a positive ST shift to persist during a transition of the heart rate between normal and elevated. In this case, it may be desirable to detect a positive shift condition, even if neither the N-SP cntr nor the EL-SP cntr have reached threshold. To effect such a detection, block 1430 compares the number of consecutive positive ST shifted segments, the sum of the N-SP cntr and the EL-SP cntr, is compared to a threshold M-SP$_{TH}$ for mixed heart rate positive ST shifts, and a mixed heart rate shift condition is flagged in block 1434 if the sum exceeds the threshold. If N-SP$_{TH}$ is set at a small value, such as its preferred value of 3, step 1430 is not important.

In block 1438, the negative shift counters N-SN cntr or EL-SN cntr are reset to 0. This step ensures that the system can keep track of the number of consecutive negative ST shifted segments.

After block 1438, control passes to block 834 of FIG. 5. It will be appreciated that the additional condition detection described with reference to FIG. 5 may be performed in conjunction with the ST polarity and heart rate routine shown in FIG. 18.

The steps for processing negative ST shifts are analogous to the steps for processing positive ST shifts except that an additional check is made to determine if a normal heart closely followed a recovery from a high heart rate (block 1633 of FIG. 18). In blocks 1408 and 1410, respectively, the EL-SN cntr and N-SN cntr, respectively, are incremented. In block 1418, the EL-SN cntr is compared to programmable elevated threshold EL-SN$_{TH}$. At higher heart rates, a longer threshold may be desirable, a preferred value for .EL-SN$_{TH}$ being approximately, 15 minutes (the effective length of time required to trigger a persistent ischemia condition in block 862 of FIG. 5).

EL-SN and N-SN flags are set in block 1426. The mixed heart rate condition is checked for a negative shift in block 1432 and a flag is set as appropriate in block 1436. Analogously to block 1438, in block 1440, the positive shift counters N-SP cntr or EL-SP cntr are reset to 0. Processing continues with block 834 of FIG. 5.

In the case of a negative shift at a normal heart rate (block 1410), as described with reference to block 1633 of FIG. 18, it is desirable to determine whether the heart has recently recovered from a period of high heart rate. This recovery checking starts at block 1452 of FIG. 20 and will be described below.

Returning to block 1402, if the current segment is not shifted, in block 1412, the four ST counters are reset to 0. Processing continues with block 834 of FIG. 5.

Turning to the handling of negative shifts at a normal heart rate, in block 1452 (FIG. 20), the routine checks whether any of the last V segments was characterized by an elevated or high heart rate. If not, then a persistent low heart rate ST shift condition is possible, and control transfers to block 1457. V may be set according to the time after cessation of exercise/high heart rate that exercise induced ST shifts resolve, the interval between segment acquisition, and the number of consecutive segments required to trigger detection of a low heart rate with ST shift condition. If there is a 90 second interval between the last sample at a high heart rate and the first sample at a normal heart rate, 30 seconds between subsequent acquisitions, then (V−1)*30+90 seconds will have elapsed between the last high heart rate segment and the current segment, assuming the first low heart rate segment and all subsequent segments are above the threshold for detecting ST shifts at normal heart rates. If it is desired to have at 5 minute window after a high heart rate before triggering detection of a persistent low heart rate ST shift condition, then V should be set to 8.

If it has been at least V segments since a high heart rate, block 1457 checks whether the N-SN cntr (normal, negative shift counter) is greater than a threshold N-SN$_{TH}$, which is preferably equal to 3 (see generally FIG. 5). If so, a persistent, negative shift at low heart rate is detected in block 1454 (block 1634 of FIG. 18). Otherwise, block 1454 is skipped.

If one of the last V segments has been high, the routine must determine if the high heart rate was very recent, in which case it is not desirable to detect any condition, or if the high heart rate occurred long enough ago to warrant an alarm. Thus, in block 1453, the routine determines whether any of the last Q segments was high, where Q is less than V and is preferably equal to 4. (It should be emphasized that both V and Q are preferably patient dependent and may be determined either after a stress test or after days or weeks worth of data are acquired with alarms either turned off or V and Q set very high.) If any segment within the last Q was elevated, then it is too soon after recovery to check for ischemia and no condition is detected.

If any segment within the last Q segments was elevated, then an ischemia check is performed in block 1459. Block 1459 checks whether the N-SN cntr (normal, negative shift counter) is greater than a threshold NR-SN$_{TH}$, which is preferably set to 4. If so, a post-elevated negative ST shift condition is detected in block 1455 (block 1636 of FIG. 18). Otherwise, no condition is detected.

In the embodiment described above, the difference between a first ischemia test (block 1457) and a second ischemia test (block 1459) is the persistence criteria applied to an ST shift, i.e., a longer period of abnormal ST shifts is required if the heart has not completely recovered from high heart rates (block 1459) compared to the case when the heart has completely recovered from high heart rates (block 1457). In an alternative embodiment, the second ischemia test involves an analysis of the trajectory of the ST (or other parameter) vs. heart rate curve.

There are other methods apart from tracking heart rate segment classifications for determining whether a heart rate recovery is occurring. For example, the average heart rate for a number of consecutive segments (e.g. V segments) may be stored. For the current segment under consideration, if any of these V segments are greater than the current heart rate by a specified amount, then recovery is assumed to be ongoing. A variant of this method is to calculate the change in heart rate between successive segments, and track this change, by, for example, generating an exponential average: dHR(i)=α*dHR(i−1)+(1−α)*(current change in heart rate). If dHR is less than a threshold, the heart is in recovery mode.

In the embodiment described above, ST shifts are determined regardless of whether there has been a recent change in heart rate because ST shift polarity determines whether a check is performed for a change in heart rate. In an alternative embodiment, changes in heart rate alone, regardless of ST shift polarity, could both disable detection and eliminate the need to calculate ST (or other parameter) shifts. In a variant of this alternate embodiment, event detection may be disabled for a period of time after a change in heart rate regardless of ST polarity but ST shifts may nonetheless be computed because it may be desirable to store ST vs. heart rate data.

Healthy persons often exhibit a positive ST vs. heart rate hysteresis. In this case, the method described above would be modified to check for heart rate changes in the case of a positive ST shift, not a negative ST shift. Furthermore, it may be desirable to perform heart rate checks, analogous to those described above, when the heart rate is increasing.

Figure 21A:
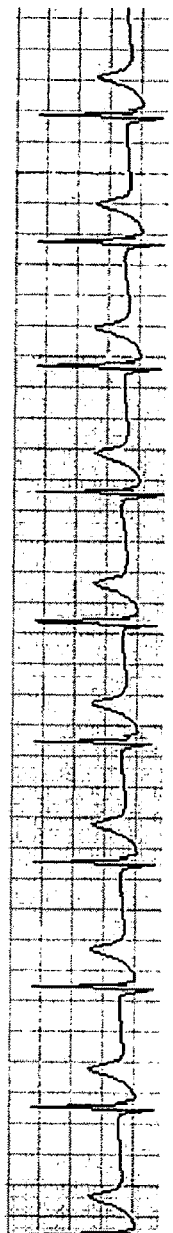
FIGS. 21a and 21b show an example of the progressive ST shift recorded by a lead with a "can to tip" polarity following total obstruction of a left anterior descending coronary artery.
Figure 21B:

In an alternative embodiment, an ischemic event may be detected during the recovery from a period of high heart rate but reclassified reclassified following the return to normal heart rate from elevated heart rate, FIGS. 21*a* and 21*b* show an example of the progressive ST shift that is seen from the can-to-tip vector by the Guardian following total obstruction of a left anterior descending coronary artery.

FIG. 21*a* shows a baseline tracing while FIG. 21*b* shows a tracing during the ischemic event. As is clear from a comparison of FIG. 21*b* with FIG. 21*a*, the LAD occlusion causes ST segment depression and significant reduction in T wave amplitude.

Figure 22A:
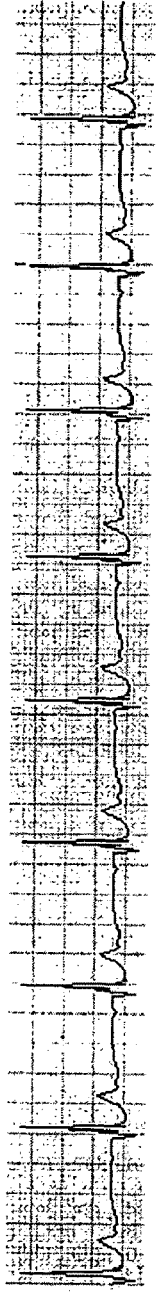
FIGS. 22a and 22b show an example of the progressive ST shift recorded by a lead with a "can to tip" polarity following total obstruction of an LCX coronary artery.
Figure 22B:
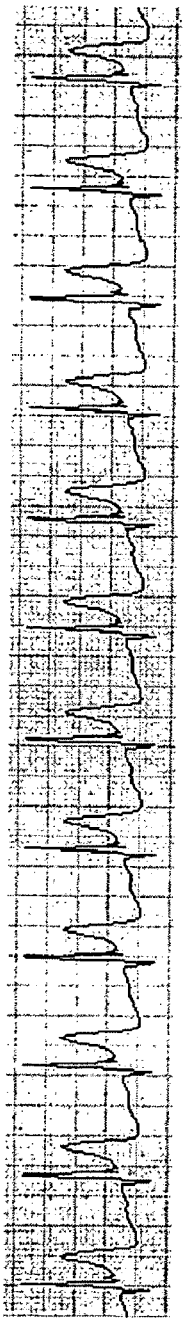

FIGS. 22a and 22b show an example of the progressive ST shift that is seen from the can-to-tip vector by the Guardian following total obstruction of an LCX coronary artery. FIG. 22a shows a baseline tracing while FIG. 22b shows a tracing during the ischemic event. As is clear from a comparison of FIG. 22b with FIG. 22a, the LCX occlusion causes ST segment elevation and significant increase in T wave amplitude.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A cardiac event detection system for detecting a cardiac event in a patient comprising:
   (a) at least two sensors for sensing an analog signal from said patient's heart;
   (b) a device coupled to said sensors, said device having an analog-to-digital circuit system contained therein for digitizing said analog signal to produce a digitized waveform;
   (c) a processor contained in said device and electrically coupled to said analog-to-digital circuit system, said processor configured to:
      (i) compute from the digitized waveform heart rate information;
      (ii) based on the heart rate information, determine whether a change in heart rate has occurred;
      (iii) responsive to a determination that a change in heart rate has occurred, determine the relative time the change in heart rate occurred;
      (iv) responsive to the determination that a change in heart rate has occurred, based on the relative timing of the change in heart rate, selectively apply a first test to detect a cardiac event.

2. The system of claim 1 wherein the first test is selectively applied based on a single change in heart rate.

3. The system of claim 1 wherein the processor is further configured to process waveform segments and to classify waveform segments according to heart rate, and wherein the determination of a change in heart rate is performed by comparing the heart rate classifications of two segments.

4. The system of claim 1 wherein the relative time the change in heart rate occurred is explicitly determined.

5. The system of claim 1 wherein the processor is further configured to compute a function that is correlated with changes in heart rate, and wherein the relative time the change in heart rate occurred is implicitly determined according to the function.

6. The system of claim 5 wherein the function is based on a filtered heart rate slope curve.

7. The system of claim 5 wherein the first test is not applied when the function exceeds a threshold.

8. The system of claim 1 wherein the first test is not applied when the change in heart rate occurred within a predetermined time before a present time, and wherein the first test is applied when the change in heart rate occurred more than a predetermined time before the present time.

9. The system of claim 1 wherein the processor is further configured to compute values of a heart signal parameter, and wherein the first test to detect a cardiac event is based on a comparison of the values of the heart signal parameter with a threshold.

10. The system of claim 1 wherein the processor is further configured to selectively apply a second test to detect a cardiac event based on the relative timing of the change in heart rate, and wherein the first test is applied when the patient's heart rate is determined to have completely recovered from a higher heart rate, and wherein the second test is applied when the patient's heart is determined to still be recovering from a higher heart rate.

11. The system of claim 10 wherein the first and second tests involve the application of persistence criteria, and wherein the second test involves the application of a stricter persistence criterion than the first test.

12. The system of claim 1 wherein the first test is selectively applied based both the change in heart rate and the magnitude of the heart rate when the change occurred.

13. A cardiac event detection system for detecting a cardiac event in a patient comprising:
   (a) at least two sensors for sensing an analog signal from said patient's heart;
   (b) a device coupled to said sensors, said device having an analog-to-digital circuit system contained therein for digitizing said analog signal to produce a digitized waveform; and,
   (c) a processor contained in said device and electrically coupled to said analog-to-digital circuit system, said processor configured to:
      (i) compute from the digitized waveform heart rate information;
      (ii) based on the heart rate information, determine whether a change in heart rate has occurred;
      (iii) responsive to a determination that a change in heart rate has occurred, determine the relative time the change in heart rate occurred;
      (iv) responsive to the determination that a change in heart rate has occurred, based on the relative timing of the change in heart rate, determine a type of response to generate; and
      (v) selectively applying a test based on the relative timing of the change in heart rate, and wherein the generation of a response that indicates a cardiac event has occurred is based on the outcome of the test.

* * * * *